US007196061B2

(12) United States Patent
Doherty et al.

(10) Patent No.: US 7,196,061 B2
(45) Date of Patent: Mar. 27, 2007

(54) COMPOUNDS THAT MODULATE NEURONAL GROWTH AND THEIR USES

(75) Inventors: Patrick Doherty, Twickenham Middlesex (GB); Gareth Williams, Ilford (GB)

(73) Assignees: Wyeth, Madison, NJ (US); King's College London, London (GB)

( * ) Notice: Subject to any disclaimer, the term of this patent is extended or adjusted under 35 U.S.C. 154(b) by 0 days.

(21) Appl. No.: 10/938,409

(22) Filed: Sep. 9, 2004

(65) Prior Publication Data
US 2005/0164920 A1 Jul. 28, 2005

Related U.S. Application Data

(60) Provisional application No. 60/603,187, filed on Aug. 20, 2004, provisional application No. 60/559,898, filed on Apr. 5, 2004, provisional application No. 60/501,864, filed on Sep. 10, 2003.

(51) Int. Cl.
*A61K 38/12* (2006.01)
(52) U.S. Cl. .......................................... 514/11; 530/317
(58) Field of Classification Search ...................... None
See application file for complete search history.

(56) References Cited

U.S. PATENT DOCUMENTS 5,981,478 A * 11/1999 Ruoslahti et al. ............. 514/10

FOREIGN PATENT DOCUMENTS

WO    WO-99/02551    *   1/1999

OTHER PUBLICATIONS

Su, et al., Bioconjugate Chem., 2002, 13, 561-570.*
Cardarelli, et al., The Journal of Biological Chemistry, 1992, 32, 23159-23164.*
Postigo, et al., Genes and Development, 2002, 16, 633-645.*
Memberg, et al., Molecular and Cellular Neuroscience, 1995, 6, 323-335.*
Saragovi et al., "Small Molecule Peptidomimetic Ligands of Neurotrophin Receptors, Identifying Binding Cites, Activation Sites and Regulatory Sites," Current Pharmaceutical Design, 2002, vol. 8, pp. 2201-2216.
Williams et al., "Overcoming the Inhibitors of Myelin with a Novel Neurotrophin Strategy," The Journal of Biological Chemistry, Feb. 18, 2005, vol. 280, No. 7, pp. 5862-5869.
Banfield, Mark J., et al. 2001. Specificity in Trk Receptor: Neurotrophin Interactions: The Crystal Structure of TrkB -d5 in Complex with Neurotrophin-4/5. *Structure* 9:1191-1199.
Binder, Devin K., et al. 2001. BDNF and epilepsy: too much of a good thing? *Trends in Neurosciences* 24(1):47-53.
Cai, Dongming, et al. 1999. Prior Exposure to Neurotrophins Blocks Inhibition of Axonal Regeneration by MAG and Myelin via a Camp-Dependent Mechanism. *Neuron* 22:89-101.

Domeniconi, Marco, et al. 2002. Myelin-Associated Glycoprotein Interacts with the Nogo66 Receptor to Inhibit Neurite Outgrowth. *Neuron* 35:283-290.
He, Xiao-Lin, and Garcia, K. Christopher. 2004. Structure of Nerve Growth Factor Complexed with the Shared Neurotrophin Receptor p75. *Science* 304:870-875.
Ibanez, Carlos F., et al: 1992. Disruption of the Low Affinity Receptor-Binding Site in NGF Allows Neuronal Survival and Differentiation by Binding to the *trk* Gene Product. *Cell* 69:329-341.
Kaplan, David R. and Miller, Freda D. 2000. Neurotrophin signal transduction in the nervous system. *Current Opinion in Neurobiology* 10:381-391.
Kobayashi, Nao R., et al. 1994. BDNF and NT-4/5 Prevent Atrophy of Rat Rubrospinal Neurons after Cervical Axotomy, Stimulate GAP-43 and Tα1-Tubulin mRNA Expression, and Promote Axonal Regeneration. *The Journal of Neuroscience* 17(24)9583-9595.
Lee, Francis S., et al. 2001. The uniqueness of being a neurotrophin receptor. *Current Opinion in Neurobiology* 11:281-286.
LeSauteur, Lynne, et al. 1995. Small Peptide Mimics of Nerve Growth Factor Bind TrkA Receptors and Affect Biological Responses. *The Journal of Biological Chemistry* 270(12):6564-6569.
Lindsay, Ronald M., et al. 1993. The Therapeutic Potential of Neurotrophic Factors in the Treatment of Parkinson's Disease. *Experimental Neurology* 124:103-118.
Liu, Yi, et al. 1999. Transplants of Fibroblasts Genetically Modified to Express BDNF Promote Regeneration of Adult Rat Rubrospinal Axons and Recovery of Forelimb Function. *The Journal of Neuroscience* 19(11)4370-4387.
Longo, Frank M., et al. 1997. Synthetic NGF Peptide Derivatives Prevent Neuronal Death via a p75 Receptor-Dependent Mechanism. *Journal of Neuroscience Research* 43:1-17.
Maliartchouk, Sergei, et al. 2000. Genuine Monovalent Ligands of TrkA Nerve Growth Factor Receptors Reveal a Novel Pharmacological Mechanism of Action. *The Journal of Biological Chemistry* 275(14):9946-9956.

(Continued)

*Primary Examiner*—Anish Gupta
*Assistant Examiner*—Satyanarayana R. Gudibande
(74) *Attorney, Agent, or Firm*—Darby & Darby

(57) ABSTRACT

Cyclic peptides and peptidomimetics are provided that bind to and/or modulate activities associated with Trk receptors, including processes associated with the growth and repair of the central nervous system (e.g., neuronal growth and survival, axonal growth, neurite outgrowth and synaptic plasticity). Cyclic peptides and peptidomimetics are also provided that block or reduce the effect of other factors that inhibit growth and/or repair of the central nervous system. Pharmaceutical compositions and other formulations comprising these compounds are provided. In addition, the invention provides methods for using the cyclic peptides and peptidomimetics to modulate Trk mediated activities, including processes such as neuronal growth, survival and recover, axonal growth, neurite outgrowth, and synaptic plasticity. Further, the invention provides methods for promoting central nervous system (CNS) neuron growth by administering a p75 receptor binding agent.

9 Claims, 22 Drawing Sheets

OTHER PUBLICATIONS

McDonald, Neil Q., et al. 1991. New protein fold revealed by a 2.3-Å resolution crystal structure of nerve growth factor. *Nature* 354(5):411-414.

McInnes, Campbell, and Sykes, Brian D. 1998. Growth Factor Receptors: Structure, Mechanism, and Drug Discovery. Growth Factor Receptors, John Wiley & Sons, Inc.:339-366.

Menei, Philippe, et al. 1998. Schwann cells genetically modified to secrete human BDNF promote enhanced axonal regrowth across transected adult rat spinal cord. *European Journal of Neuroscience* 10:607-621.

Monnier, Philippe P., et al. 2003. The Rho/ROCK pathway mediates neurite growth-inhibitory activity associated with the chondroitin sulfate proteoglycans of the CNS glial scar. *Molecular and Cellular Neuroscience* 22:319-330.

O'Leary, Paul D., and Hughes, Richard A. 2003. Design of Potent Peptide Mimetics of Brain-derived Neurotrophic Factor. *The Journal of Biological Chemistry* 278(28):25738-25744.

Olson, Lars. 1994. Neurotrophins in Neurodegenerative Disease: Theoretical Issues and Clinical Trials. *Neurochem. Int.* 25(1):1-3.

Snider, William. D. 1994. Functions of the Neurotrophins during Nervous System Development: What the Knockouts Are Teaching Us. *Cell* 77:627-238.

Urfer, Roman, et al. 1994. The binding epitopes of neurotrophin-3 to its receptors trkC and gp75 and the desisgn of a multifunctional human neurotrophin. *The EMBO Journal* 13(24):5896-5909.

Wang, Kevin C., et al. 2002. Oligodendrocyte-myelin glycoprotein is a Nogo receptor ligand that inhibits neurite growth. *Nature* 417:941-944.

Wiesmann, Christian, et al. 1999. Crystal structure of nerve growth factor in the complex with the ligand-binding domain of the TrkA receptor. *Nature* 401:184-.

Xie, Youmei, et al. 2000. Nerve Growth Factor (NGF) Loop 4 Dimeric Mimetics Activate ERK and AKT and Promote NGF-like Neurotrophic Effects. *The Journal of Biological Chemistry* 275(38):29868-29874.

* cited by examiner

```
BDNF      ------------------APMKEANIRG---QGGLAYPGVRTHGTLESVNGPKAGSRGL   38
NT4       -----------------------------QP---PPSTLPPFLAP-------           13
NT3       QGNNMDQRSLPEDSLNSLIIKLIQADILKNKLSKQMVDVKENYQSTLPKAEAPREPERGG   60
NGF       ----------EPHSESNVPAGHTIPQVHWTKLQHSLDTALRRARSAPAAAIAARVAG---   47

BDNF      TSLADTFEHVIEELLDEDQKVRPNEENNKDADLYTSRVMLSSQVPLEPPLLFLLEE--YK   96
NT4       ----------------------------EWDLLSPRVVLSRGAPAGPPLLFLLEAGAFR   44
NT3       PAKS----------AFQPVIAMDTELLRQQRRYNSPRVLLSDSTPLEPPPLYLMED--YV  108
NGF       ---------------QTRNITVDPRLFKKRRLRSPRVLFSTQPPREAA---DTQDLDFE   88

BDNF      NYLDA-ANMSMR-VRRHSDPA-RRGELSVCDSISEWVTAADKKTAVDMSGGTVTVLEKVP  153
NT4       ESAGAPANRSRRGVSETAPAS-RRGELAVCDAVSGWVT--DRRTAVDLRGREVEVLGEVP  101
NT3       GSPVV-ANRTSRRKRYAEHKS-HRGEYSVCDSESLWVT--DKSSAIDIRGHQVTVLGEIK  164
NGF       VGGAAPFNRTHRSKRSSSHPIFHRGEFSVCDSVSVWVG--DKTTATDIKGKEVMVLGEVN  146

BDNF      VSKGQ-LKQYFYETKCNPMGYTKEG-------CRGIDKRHWNSQCRTTQSYVRALTMDSK  205
NT4       AAGGSPLRQYFFETRCKADNAEEGGPGAGGGGCRGVDRRHWVSECKAKQSYVRALTADAQ  161
NT3       TGNSP-VKQYFYETRCKEARPVKNG-------CRGIDDKHWNSQCKTSQTYVRALTSENN  216
NGF       INNSV-FKQYFFETKCRDPNPVDSG-------CRGIDSKHWNSYCTTTHTFVKALTMDG-  197

BDNF      KRIGWRFIRIDTSCVCTLTIKRGR--  229
NT4       GRVGWRWIRIDTACVCTLLSRTGRA-  186
NT3       KLVGWRWIRIDTSCVCALSRKIGRT-  241
NGF       KQAAWRFIRIDTACVCVLSRKAVRRA  223
```

```
trkA  271  VGRAEVSVQVNVSFPASVQ-LHTAVEMHHWCIPFSVDGQPAPSLRWL
trkB  272  VGEDDQDSYNLTVHFAPTITFLESPTSDHHWCIPFTVKGNPKPALQWF
trkC  290  VGMSNASVALTVYYPPRVVSLEEPELRLEHCIEFVVRGNPPPTLHWL
                            |—————Immunoglobulin II—————| trkA  370  FNGSVLNETSFIFTEFLEPAANETVRHGCLRLNQPTHVNNGNYTLLAANPFGQ
trkB  370  YNGAILNESKYICTKIH--VTNHTEYHGCLQLDNPTHMNNGDYTLIAKNEYGK
trkC  387  HNGQPLRESKIIHVEYY--QEGEIS-EGCLLFNKPTHYNNGNYTLIAKNPLGT trkA       ASASIMAAFM-----DNPF----EF-NPEDPIPDTNS----
trkB       DEKQISAHFMGWPGIDDGANPNYPDVIYEDYGTAANDIGDTTNRSNE
trkC       ANQTIHGHFL------KEPFPEST-DNF-ILFDEVSPT----
                                                |—Transmembrane trkA       -TSGDPVEKKDET---PFGVSVAVGLAVFACLFLSTLLLVLNKCGRRNKFGIN
trkB       IPSTDVTDKTGREHLSYYAVVVIASVVGF-C--LLVMLFLL--KLARHSKFGMK
trkC       -PPITVTHKPEED---TFGVSIAVGLAAFACVLLVVLFVMINKYGRRSKFGMK
                                                         |Juxtamembrane| trkA  446  RP-AVLAPEDGLAMSLHFMTLGGSSLSPTE-GKGSGLQG---HIIE      SDACVHHIKRRDIVLKWELGEGAFGKVFLAECHNLLPEQD
trkB  466  GPASVISNDDDDSASPLHHISNGSNTPSSSEGGPDAVIIGMTKIPVIE    NPOYFGITNSQLKPDTFVQHIKRHNIVLKRELGEGAFGKVFLAECYNLCPEQD
trkC  466  GPVAVISGE̲E̲DSASPLHHINHGIITPSSLDAGPDTVVIGMTRIPVIE    NPOYFRQGHNCHKPDTYVQHIKRRDIVLKRELGEGAFGKVFLAECYNLSPTKD
```

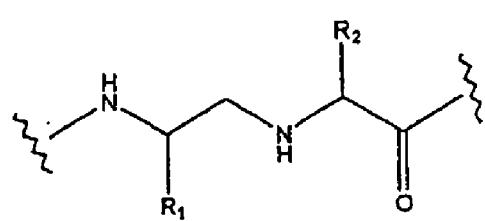
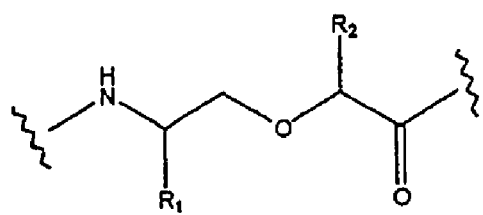
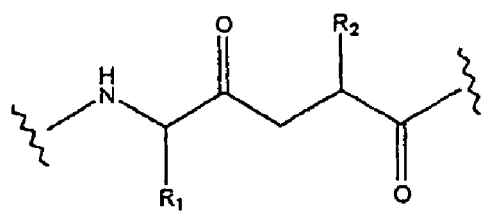
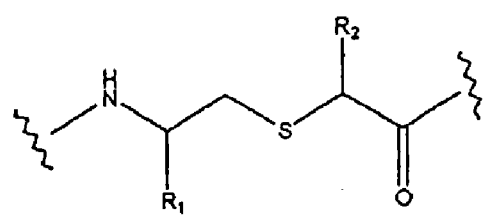
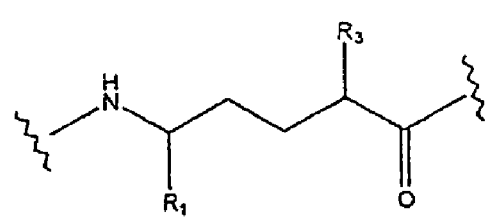
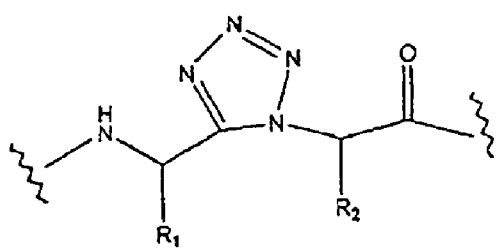
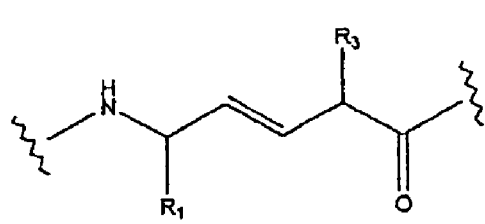
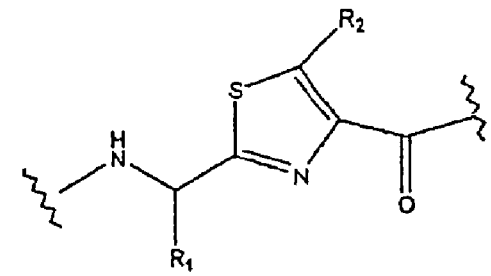
Figure 3B

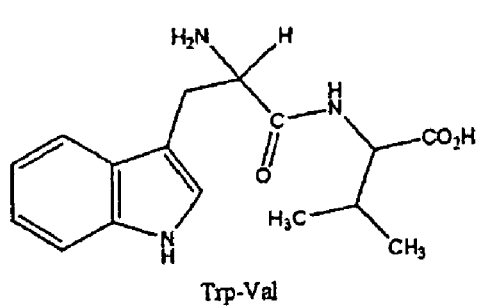
Trp-Val
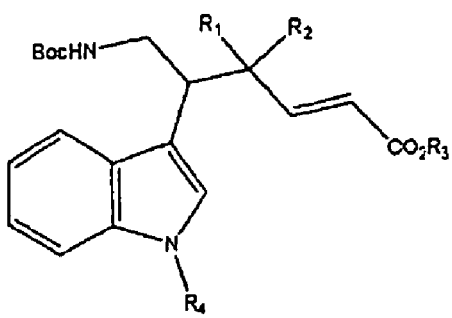
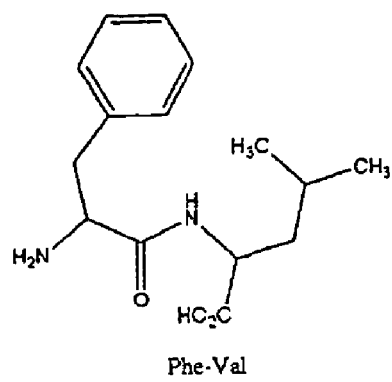
Phe-Val
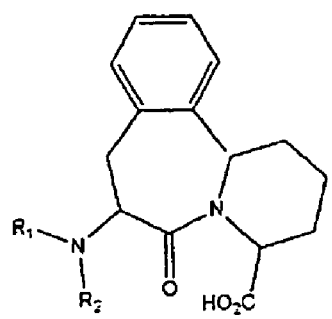
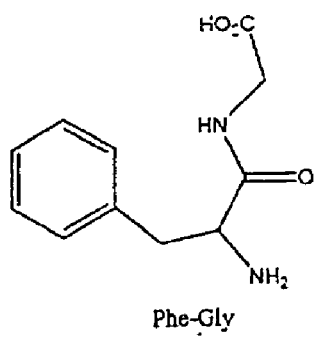
Phe-Gly
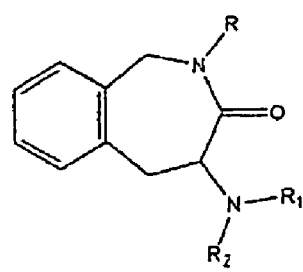
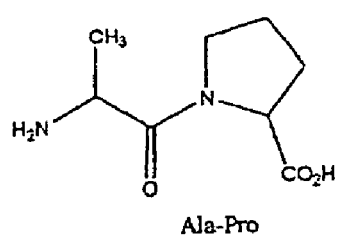
Ala-Pro
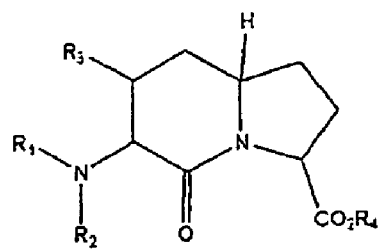
Figure 4

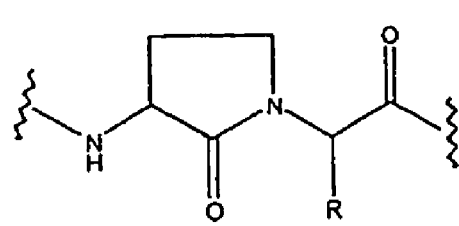
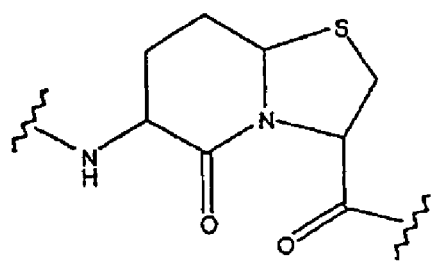
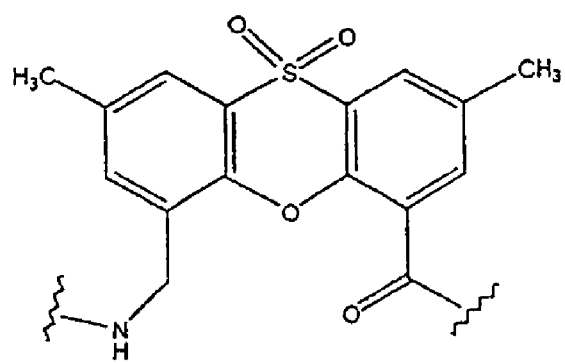
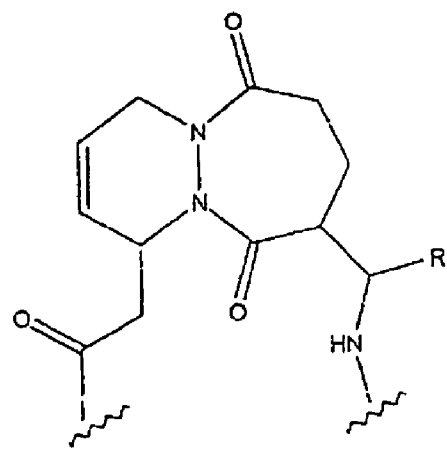
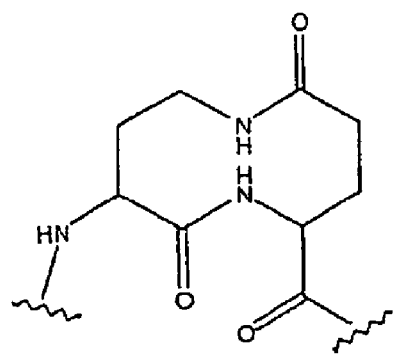
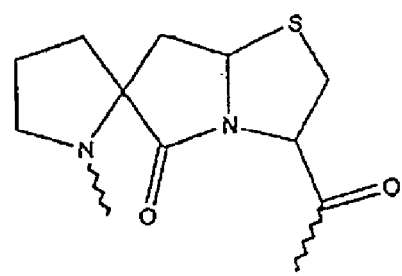
Figure 5

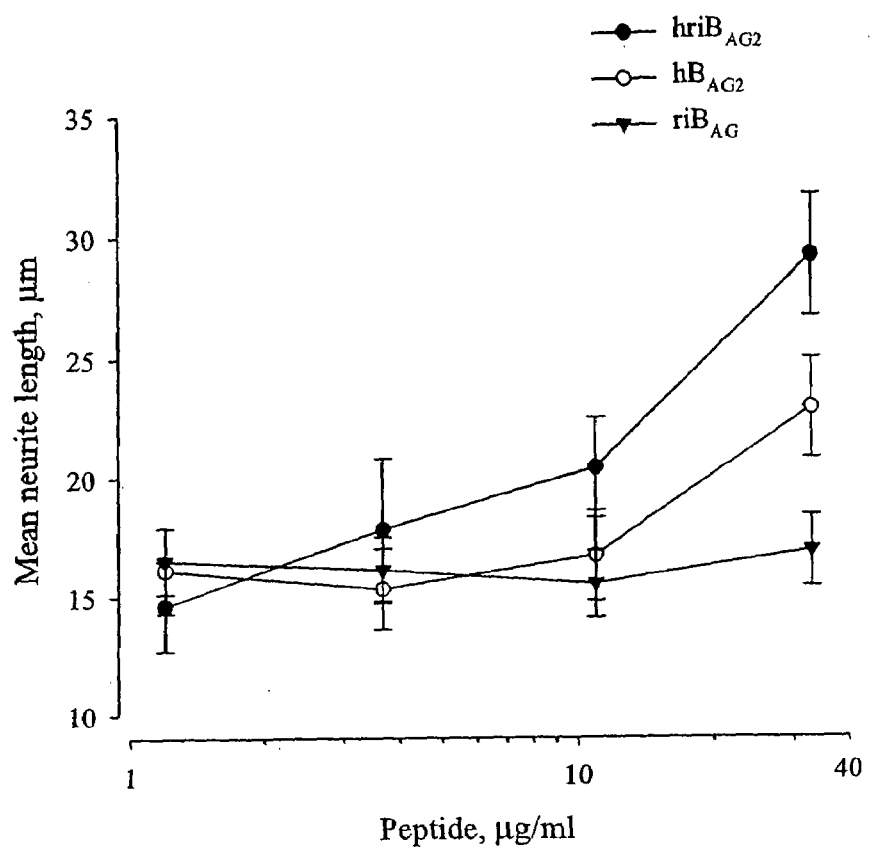
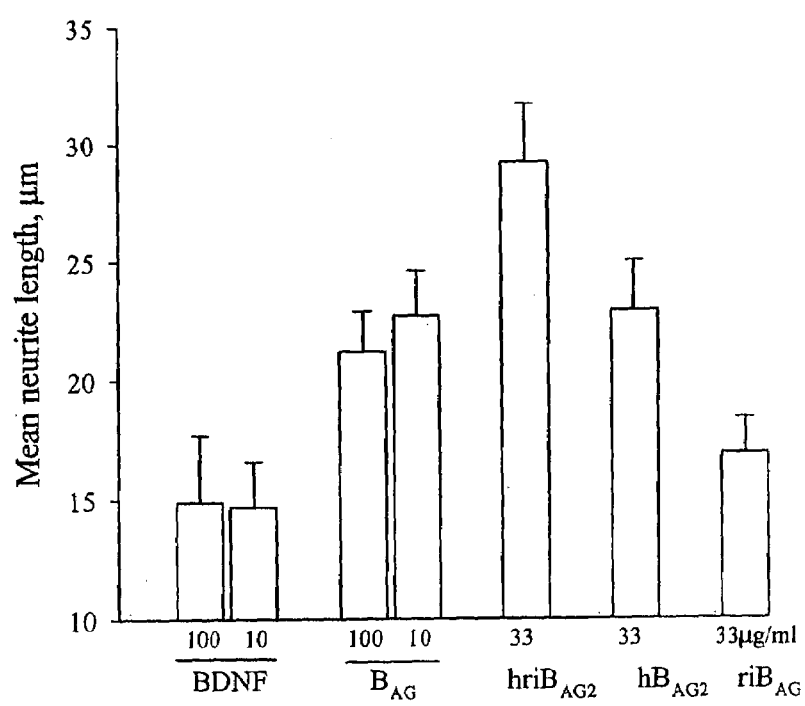
Figure 18 A & B

```
BDNF    ------------------APMKEANIRG---QGGLAYPGVRTHGTLESVNGPKAGSRGL  38
NT4     --------------------------------QP---PPSTLPPFLAP-------      13
NT3     QGNNMDQRSLPEDSLNSLIIKLIQADILKNKLSKQMVDVKENYQSTLPKAEAPREPERGG  60
NGF     ----------EPHSESNVPAGHTIPQVHWTKLQHSLDTALRRARSAPAAAIAARVAG---  47

BDNF    TSLADTFEHVIEELLDEDQKVRPNEENNKDADLYTSRVMLSSQVPLEPPLLFLLEE--YK  96
NT4     ------------------------------EWDLLSPRVVLSRGAPAGPPLLFLLEAGAFR  44
NT3     PAKS----------AFQPVIAMDTELLRQQRRYNSPRVLLSDSTPLEPPPLYLMED--YV 108
NGF     ----------------QTRNITVDPRLFKKRRLRSPRVLFSTQPPREAA---DTQDLDFE  88

BDNF    NYLDA-ANMSMR-VRRHSDPA-RRGELSVCDSISEWVTAADKKTAVDMSGGTVTVLEKVP 153
NT4     ESAGAPANRSRRGVSETAPAS-RRGELAVCDAVSGWVT--DRRTAVDLRGREVEVLGEVP 101
NT3     GSPVV-ANRTSRRKRYAEHKS-HRGEYSVCDSESLWVT--DKSSAIDIRGHQVTVLGEIK 164
NGF     VGGAAPFNRTHRSKRSSSHPIFHRGEFSVCDSVSVWVG--DKTTATDIKGKEVMVLGEVN 146

BDNF    VSKGQ-LKQYFYETKCNPMGYTKEG-------CRGIDKRHWNSQCRTTQSYVRALTMDSK 205
NT4     AAGGSPLRQYFFETRCKADNAEEGGPGAGGGGCRGVDRRHWVSECKAKQSYVRALTADAQ 161
NT3     TGNSP-VKQYFYETRCKEARPVKNG------CRGIDDKHWNSQCKTSQTYVRALTSENN 216
NGF     INNSV-FKQYFFETKCRDPNPVDSG------CRGIDSKHWNSYCTTTHTFVKALTMDG- 197

BDNF    KRIGWRFIRIDTSCVCTLTIKRGR-- 229
NT4     GRVGWRWIRIDTACVCTLLSRTGRA- 186
NT3     KLVGWRWIRIDTSCVCALSRKIGRT- 241
NGF     KQAAWRFIRIDTACVCVLSRKAVRRA 223
```

Figure 19

COMPOUNDS THAT MODULATE NEURONAL GROWTH AND THEIR USES

1. CROSS-REFERENCE TO RELATED APPLICATIONS

Priority is claimed under 35 U.S.C. 119(e) to U.S. provisional patent application Ser. No. 60/501,864, filed on Sep. 10, 2003; Ser. No. 60/559,898, filed Apr. 5, 2004; and Ser. No. 60/603,187, filed Aug. 20, 2004. The contents of these provisional applications are hereby incorporated by reference, in their entireties.

2. FIELD OF THE INVENTION

The present invention relates to compositions and methods for modulating the growth and repair of the central nervous system (CNS), including processes such as neuronal survival, axonal growth and synaptic plasticity. More specifically, the invention relates to compounds (including cyclic peptides and peptidomimetic compounds) that are either agonists or antagonists of a family of receptors, known as Trk receptors, that are expressed on the surface of neuronal cells and which regulate such processes of CNS growth and repair. Further, the invention relates to methods for promoting CNS growth and repair using a p75 binding agent.

3. BACKGROUND OF THE INVENTION

Injury to the central nervous system (CNS) can have devastating consequences due to the poor regenerative capacity of neurons in that environment. This contrasts markedly with the comparatively good regenerative capacity of neurons in the peripheral nervous system. See, for example, Homer & Gage, *Nature* 2000, 407:963–970. Numerous diseases, such as Alzheimer's disease, Parkinson's disease, stroke, head and spinal cord trauma to name a few, are all associated with damage to the CNS that is often severe, even debilitating, long lasting or even permanent. No cure is presently available for these conditions, and even palliative treatments are lacking.

3.1. Neurotrophins

It is now understood that the growth and regeneration of neurons is regulated at least in part by certain polypeptide growth factors, known as neuroptrophins or "NTs," which bind to and activate cell surface receptors having an intrinsic tyrosine kinase activity. Upon neurotrophin binding, these receptors are believed become autophosphorylated on one or more amino acid residues and subsequently associate with intracellular molecules important for signal transduction. For a review, see Ulrich & Schlessinger, *Cell* 1990, 61:203–212.

The first identified neurotrophin is known in the art as nerve growth factor (NGF) and has a prominent effect on developing sensory and sympathetic neurons of the peripheral nervous system. See, Levi-Montalcini & Angeletti, *Physiol. Rev.* 1968, 48:534–569; Thoenen et al., *Rev. Physiol. Biochem. Pharmacol.* 1987, 109:145–178; Thoenen & Barde, *Physiol. Rev.* 1980, 60:1284–1325; Whittemore & Seiger, *Brain Res.* 1987, 434:439–464; Angeletti & Bradshaw, *Proc. Natl. Acad. Sci. U.S.A.* 1971, 68:2417–2420; Angeletti et al., *Biochemistry* 1973, 12:100–115. NGF orthologs have also been isolated and characterized in a number of other species, including mice, birds, reptiles and fishes (Scott et al., *Nature* 1983, 302:538–540; Schwartz et al., *J. Neurochem.* 1989, 52:1203–1209; and Hallböök et al., *Neuron* 1991, 6:845–858.

A number of other NTs are also known in the art. These include brain-derived neurotrophic factor (BDNF), which is also known as neurotrophin-2 (NT-2). See, Leibrock et al., *Nature* 1989, 341:149–152. Still other NTs include a factor originally called neuronal factor (NF) and now commonly referred to as neurotrophin-3 or "NT-3" (Emfors et al., *Proc. Natl. Acad. Sci. U.S.A.* 1990, 87:5454–5458; Höhn et al., *Nature* 1990, 344:339; Maisonpierre et al., *Science* 1990, 247:1446; Rosenthal et al., *Neuron* 1990, 4:767; Jones & Reichardt, *Proc. Natl. Acad. Sci. U.S.A.* 1990, 87:8060–8064; and Kaisho et al., *FEBS Lett.* 1990, 266:187). Neurotrophins-4 and -5 (NT-4 and NT-5) are also known. See, Hallbook et al., *Neuron* 1991, 6:845–858; Berkmeier et al., *Neuron* 1991, 7:857–866; Ip et al., *Proc. Natl. Acad. Sci. U.S.A.* 1992, 89:3060–3064. See also, U.S. Pat. No. 5,364,769 issued Nov. 15, 1994 to Rosenthal. Because it was subsequently seen to be a mammalian ortholog of the *Xenopus* NT-4 described by Hallbrook et al., supra, the mammalian NT-5 molecule described by Berkmeier et al., supra, is also commonly referred to as NT-4/5. An alignment of NT's BDNF, NT4, NT3, and NGF is provided in FIG. 1.

3.2. Trk Receptors

Neurotrophins mediate their effect through a family of receptor tyrosine kinases that are expressed on the surface of neuronal cells and referred to collectively as Trk-receptors. At least three different Trk-receptors are known and have been described in the art: TrkA, TrkB and TrkC. For a review, see U.S. Pat. Nos. 5,844,092; 5,877,016; 6,025,166; 6,027,927; and 6,153,189 all by Presta et al. Although the structure and sequences of the different Trk-receptors are similar, alternate splicing increases the complexity of this family giving rise to several different isoforms of each receptor. An alignment of the different Trk-receptor amino acid sequences is provided here at FIG. 2A–2C setting forth the consensus sequences and boundaries for the various domains of each receptor. See also, FIGS. 16A–16C in U.S. Pat. No. 5,877,016.

Each of the different Trk-receptors exhibits particular binding affinity for the different neurotrophins, although there is some overlap. Hence, TrkA is believed to bind not only NGF, but also NT-3 and NT-4/5 (but not BDNF). TrkB is believed to bind BDNF, NT-3, NT-4 and NT-4/5, but not NGF. By contrast, TrkC is believed to bind only NT-3 and not any of the other neurotrophins.

A number of studies have validated the Trk-receptors as therapeutic targets for brain repair. See, for example, Liu et al., *J. Neurosci.* 1999, 19:4370–4387; Menei et al., *Eur. J. Neurosci.* 1998, 10:607–621; and Kobayashi et al., *J. Neurosci.* 1997, 17:9583–9595. The Trk-receptors and their ligands have also been studied using X-ray crystallography to obtain three-dimensional structures of the ligand-receptor binding complexes. Wiesmann et al., *Nature* 1999, 401:184–188; Banfield et al., *Structure (Camb)* 2001, 9:1191–1199. These and other studies suggest that neurotrophin binding to the Trk-receptors induces dimerization of receptor monomers, resulting in an increase of the receptors' intrinsic tyrosine kinase activity. This increased activity triggers, in turn, signaling cascades that are believed to be beneficial to neurons by promoting neuronal survival, axonal growth, and synaptic plasticity. Snider, *Cell* 1994, 77:627–638; Kaplan & Miller, *Curr. Opin. Neurobiol.* 2000, 10:381–391.

There has therefore been considerable recognition that therapeutic compounds which target and activate Trk-receptors (i.e., Trk-receptor "agonists") would be beneficial and desirable. See, for example, Lindsay et al., *Exp. Neurol.*

1993, 124:103–118; Olson, *Neurochem. Int.* 1994, 25:1–3. Moreover, increased levels of certain neurotrophins (e.g., BDNF) are also associated with medical conditions such as epilepsy (Binder et al., *Trends Neurosci.* 2001, 24:47–53). Hence, even compounds that inhibit Trk-receptor activity (i.e., Trk-receptor "antagonists") would be beneficial. Despite this long felt need, such compounds have been elusive at best. As large-molecules, the therapeutic delivery of effective levels of neurotrophins themselves presents considerable, possibly insurmountable, challenges. Moreover, natural neurotrophins may interact with other receptors, such as the p75 receptor in neurons, which is associated with neuronal apoptosis and growth cone collapse. Lee et al., *Curr. Opin. Neurobiol.* 2001, 11:281–286.

However, previous efforts to design peptidomimetic agonists and/or antagonists of Trk-receptors have also been unsuccessful. For example, cyclic peptides derived from loop 1 of the neurotrophin NGF have been reported to moderately mimic the survival activity of NGF. However, these peptides appear to function in a p75, rather Trk-receptor, dependent manner. Long et al., *J. Neurosci. Res.* 1997, 48:1–17. Some NGF loop 4 cyclic peptides are said to show NGF-like survival activity that is blocked by a Trk antagonist. However, the maximal survival response induced by those peptides is reported to be only 10–15% of the maximal response promoted by the NGF neurotrophin itself. See, Xie et al., *J. Biol. Chem.* 2000, 275:29868–29874; and Maliartchouk et al., *J. Biol. Chem.* 2000, 275:9946–9956. Bicyclic and tricyclic dimeric versions of BDNF loop 2 peptides have been shown to have BDNF-like activity. Again, however, the maximal survival response they induce is reported to be only 30% of the maximal response promoted by the natural neurotrophin. O'Leary et al., *J. Biol. Chem.* 2003, 278:25738–25744 (Electronic publication May 2, 2003).

There continues to exist, therefore, a long felt need for compositions that can modulate (i.e., increase or inhibit) neuronal growth and recovery. There also exists a need for processes and methods (including therapeutic methods) that effectively modulate neuronal growth and recovery.

3.21. The p75 Receptor Neurotrophin Receptor

The p75 receptor is known to play roles in signaling complexes for neuronal apoptosis and growth inhibition. Barker, *Neuron* 2004, 42:529–533. The p75 receptor is a member of the tumor necrosis factor (TNR) superfamily and is characterized by cysteine-rich domains (CRDs) in its extracellular portion. These CRDs are required for neurotrophin binding, and p75 receptor serves as a low affinity receptor for neurotrophins such as NGF, BDNF, NT-3, and NT-4. Huang and Reichardt, *Annu. Rev. Biochem.* 2003, 72:609–642. NGF, BDNF, NT-3 and NT-4 can effectively compete with each other for binding to p75 receptor. In inhibitory environments, these neurotrophins can be used to compete out each other's binding to p75 receptor in order to reveal responses that depend solely on Trk signaling. Barker and Shooter, *Neuron* 1994, 13:203–215.

3.22. The p75 Receptor and the NGF TDIKGKE Motif

It is known that the TDIKGKE (SEQ ID NO:42) motif that constitutes the first β hairpin loop of NGF plays a crucial role in the binding of NGF to the p75 receptor. He and Garcia, *Science* 2004, 304:870–875; Ibanez et al., *Cell* 1992, 69:329–341. Furthermore, constrained TDIKGKE (SEQ ID NO:42) motifs interact with the p75 receptor and are expected to compete for neurotrophin binding to this receptor. Longo et al., *J. Neurosci. Res.* 1997, 48:1–17.

The cyclic peptides and peptidomimetic compounds derived from loop 1 of NGF have been reported to moderately mimic NGF's neuron growth-promoting activity (see U.S. Pat. No. 6,017,878 to Saragovi et al.), and these peptides appear to function in a p75 receptor-dependent manner (Longo et al., *J. Neurosci. Res.* 1997, 48:1–17). Some NGF loop 4 cyclic peptides are said to show NGF-like neuron growth promotion that is blocked by a Trk antagonist. However, the maximal response induced by those peptides is reported to be only 10–15% of the maximal response promoted by the NGF neurotrophin itself. See Xie et al., *J. Biol. Chem.* 2000, 275:29868–29874; and Maliartchouk et al., *J. Biol. Chem.* 2000, 275:9946–9956. Bicyclic and tricyclic dimeric versions of BDNF loop 2 peptides have been shown to have BDNF-like activity. Again, however, the maximal response they induce is reported to be only 30% of the maximal response promoted by the natural neurotrophin. O'Leary et al., *J. Biol. Chem.* 2003, 278:25738–25744 (Electronic publication May 2, 2003).

3.3. Inhibitory Signals

The central nervous system's limited ability to repair injuries is thought to be at least partly due to the presence of inhibitory products that prevent axonal regeneration—including inhibitors associated with damaged myelin (Berry, *Bibl. Anat.* 1982, 23:1–11). Indeed, biochemical studies on central myelin have identified two protein fractions that contain inhibitory activity for cell spreading (Caroni & Schwab, *J. Cell Biol.* 1988, 106:1281–1288) and monoclonal antibodies that bind to those fractions enhance the growth of cultured sensory and sympathetic neurons in what are otherwise non-permissive substrates for neurite growth (Caroni & Schwab, *Neuron* 1988, 1:85–96). Studies with these same antibodies in lesioned animals have also shown that functional recovery can be obtained by blocking the function of inhibitory molecules associated with myelin (Bregman et al., *Nature* 1995, 378:498–501; Schnell & Schwab, *Nature* 1990, 343:269–272). A much more robust regeneration response has been obtained in mice immunized with whole myelin (Huang et al., 1999) further demonstrating that CNS recovery and repair can be enhanced in vivo, by blocking inhibitory factors.

At least three myelin derived molecules are known that are potent inhibitors of axonal growth: the myelin-associated glycoprotein, which is also referred to as "MAG" (described by McKerracher et al., *Neuron* 1994, 13:805–811; and by Mukhopadhyay et al., *Neuron* 1994, 13:757–767); Nogo-A (see, Chen et al., *Nature* 2000, 403:434–439; GrandPre et al., *Nature* 2000, 403:439–444; and Prinjha et al., *Nature* 2000, 403:383–384) and the oligodendrocyte myelin glycoprotein (Wang et al., *Nature* 2002, 417:941–944). The Nogo receptor (also referred to as "NgR"), the ganglioside GT1b and the p75 neurotrophin receptor (also referred to as "p75$^{NTR}$" or "p75NTR") have been implicated in mediating responses to all three of these inhibitory molecules. Specifically, binding to NgR is said to be required for inhibitory activity by all three inhibitors MAG, Nogo-A and oligodendrocyte glycoprotein (Domeniconi et al., 2002; Liu et al., 2002; Wang et al., 2002b). However, MAG can also bind directly to the GT1b receptor (Vyas & Schnaar, *Biochimie* 2001, 83:677–682). Moreover, antibody induced clustering of GT1b receptor can mimic the inhibitory response produced by MAG (see, Vinson et al, *J. Biol. Chem.* 2001, 276:20280–20285; and Vyas et al., *Proc. Natl. Acad. Sci. U.S.A.* 2002, 99:8412–8417).

The p75 receptor is the signaling component of a multimeric receptor complex than can bind all three myelin receptors. See Domeniconi et al., *Neuron* 2002, 35:283–290; Liu et al., *Science* 2002, 297:1190–1993; Wang et al., *Nature* 2002, 417:941–944. Interactions between the GT1b and p75$^{NTR}$ receptors have been reported (Yamashita et al., 2002), as have interactions between the NgR and p75$^{NTR}$ receptors (see, Wang et al., 2002a; and Wong et al., 2002). Such interactions with p75$^{NTR}$ are thought to be important in the transmission of inhibitory signals (e.g., from MAG, Nogo-A and/or oligodendrocyte glycoprotein) across the cell membrane. For example, interactions of MAG or a Nogo-A peptide with cells that express NgR increases association of p75$^{NTR}$ with Rho-GDI, and induces the release of RhoA from that complex (Yamashita & Tohyma, Nat. Neurosci. 2003, 6:461–471). This step is a pre-requisite for activation of RhoA and inhibition of growth (Id), and the inhibition of RhoA and/or Rho kinase (a downstream effector of RhoA) effectively circumvents inhibitory activity, e.g., of myelin in cultured neurons (see, for example, Dergham et al., J. Neurosci. 2002, 22:6570–6577; Fournier et al., J. Neurosci. 2003, 23:1416–1423; and Lehmann et al., J. Neurosci. 1999, 19:7537–7547).

As noted above, the various neurotrophins (e.g., NGF, BDNF, NT-3 and NT-4/5) do have dramatic effects on neuronal survival and axonal growth during development. It has been recently suggested that neurotrophins and inhibitory molecules (for example, MAG, Nogo-A and oligodendrocyte glycoprotein) may have an opposing effect on the coupling of p75$^{NTR}$ receptor to Rho-GDI (see, Yamashita & Tohyama, Nat. Neurosci. 2003, 6:461–467). Nevertheless, it has not as of yet been possible to promote robust, long range axonal regeneration using neurotrophins. This is believed to be at least partly due to the inability of neurotrophins to effectively counteract inhibitory signals such as those described above. For example, the treatment of cultured neurons with neurotrophins such as NGF, BDNF or GDNF (glial derived neurotrophic factor) does not normally counteract the inhibitory activity of myelin unless the neurons are first "primed" by exposure to the neurotrophin for several hours before exposure to the inhibitory signal (Cai et al., Neuron 1999, 22:89–101). Such priming, however, is of limited effect, time consuming, cumbersome to apply, and impractical for clinical and other in vivo applications. Moreover (and as noted above), the therapeutic delivery of neurotrophins themselves, which are large molecules, presents considerable and possibly insurmountable technical challenges. Furthermore, neurotrophins may be compromised in their ability to promote regeneration because they bind to the inhibitory complex through their interaction with the p75 receptor. Neurotrophins, which are bound to p75 receptor, cannot activate Trk receptors to overcome inhibitory signaling and to promote neuronal growth.

Hence, there additionally exists a need for compounds that can effectively modulate the effects of inhibitory signals on neuronal growth and recovery—including compounds that effectively modulate effects of inhibitory signals such as those produced by MAG, Nogo-A, oligodendrocyte glycoprotein, NgR, GT1b, p75$^{NTR}$ and/or downstream effectors of these signaling molecules. In particular, there exists a need for compounds that can effectively counteract such inhibitory signals, and/or stimulate neuronal growth and recovery. There also exists a need for processes and methods (including therapeutic methods) that modulate effects of such inhibitory signals and, in particular, for processes and methods that counteract such inhibitory signals and/or stimulate neuronal growth and recovery.

The citation and/or discussion of a reference in this section and throughout the specification is provided merely to clarify the description of the present invention and is not an admission that any such reference is "prior art" to the invention described herein.

4. SUMMARY OF THE INVENTION

The present invention provides at least a partial solution to the above-mentioned problems in the art by providing compounds and formulations thereof which modulate (e.g., enhance or inhibit) activity mediated by a Trk receptor such as TrkA, TrkB or TrkC. For example, in one embodiment the invention provides compounds that are Trk antagonists and, as such, inhibit Trk mediated activity. In other embodiments, the invention provides compounds that are Trk agonists and, as such, enhance or increase Trk mediated activity.

As noted above, Trk receptors and their ligands (i.e., neurotrophins such as NGF, BDNF, NT-3, NT-4, NT-5 and NT-4/5) are associated with the growth and repair of the central nervous system (CNS). As such, Trk modulator compounds of the present invention can be used to modulate such processes, including processes of neuronal growth and survival, axonal growth, neurite outgrowth, and synaptic plasticity. In one aspect, therefore, the present invention provides methods (including therapeutic methods) that use Trk modulator compounds of the invention to modulate (e.g., enhance or inhibit) such processes.

In one particular embodiment, the invention provides cyclic peptide compounds that modulates Trk receptor mediated activity. These cyclic peptides preferably comprise, within a cyclic peptide ring, the amino acid sequence: Arg-Gly-Glu. In a more particular embodiment, the cyclic peptide comprises the formula:

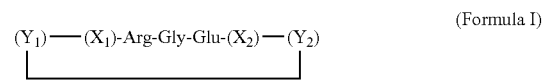

(Formula I)

In Formula I, the elements $Y_1$ and $Y_2$ are independently selected amino acids with a covalent bond formed between $Y_1$ and $Y_2$. The element $X_1$ and $X_2$ are optional and, if present, are independently selected amino acids or sequences of amino acids joined by peptide bonds. Preferably $X_1$ and/or $X_2$ are each between zero and about 10 amino acids in length, and are more preferably about 1, 2, 3, 4 or 5 amino acids in length. Moreover, $X_1$ and $X_2$ are also preferably selected so that the size of the cyclic peptide ring ranges from about 5 to about 15 amino acids in length, and is more preferably between about 5–10 amino acids in length.

The invention further provides, in particular embodiments, cyclic peptides having the formula:

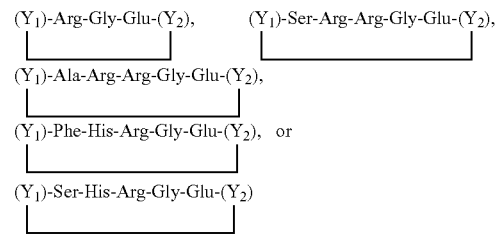

where $Y_1$ and $Y_2$ are as described above, for Formula I. Particularly preferred cyclic peptides of the invention are ones comprising the amino acid sequence: CSRRGEC (SEQ ID NO:1), N-Ac-CSRRGEC-NH$_2$ (SEQ ID NO:2), CARRGEC (SEQ ID NO:3), N-Ac-CARRGEC-NH$_2$ (SEQ ID NO:4), CFHRGEC (SEQ ID NO:5), N-Ac- CFHRGEC-NH$_2$ (SEQ ID NO:6), CSHRGEC (SEQ ID NO:7), N-Ac-CFHRGE-NH$_2$ (SEQ ID NO:8), CRGEC (SEQ ID NO:9), N-Ac-CRGEC-NH$_2$ (SEQ ID NO:10), N-Ac-KRGED-NH$_2$ (SEQ ID NO:11), H—C(O)-CRGEC-NH$_2$ (SEQ ID NO:12), CH$_3$—SO2-NH-CRGEC-NH$_2$ (SEQ ID NO:13), N-Ac-CRGEC-Y-NH$_2$ (SEQ ID NO:14), H—C(O)-CRGEC-Y-NH$_2$ (SEQ ID NO:15) and CH$_3$—SO$_2$— NH-CRGEC-Y-NH$_2$ (SEQ ID NO:16), (where the underlined portion of each amino acid sequence indicates that portion of the peptide that is cyclized).

Preferred cyclic peptides of the above formulas and sequences are Trk antagonists. However, the invention also provides, in other embodiments, cyclic peptides that are Trk agonists. Such cyclic peptides preferably have the formula:

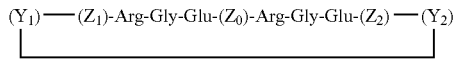

(Formula II)

In Formula II, above, the elements $Y_1$ and $Y_2$ are independently selected amino acids with a covalent bond formed between $Y_1$ and $Y_2$. The elements $Z_1$, $Z_2$ and $Z_0$ are optional and, if present, are independently selected amino acids or sequences of amino acids joined by peptide bonds. Preferably, $Z_1$, $Z_2$ and/or $Z_0$ are each no more than about ten amino acids in length, and are more preferably only about 1, 2, 3, 4, 5 or 10 amino acids in length. Moreover, the lengths of $Z_1$, $Z_2$ and/or $Z_0$ are preferably selected so that the size of the cyclic peptide ring ranges from about 10–50 amino acids in length, and more preferably from about 10–25 or from about 15–20 amino acids in length. In particularly preferred embodiments, the elements $Z_1$, $Z_2$ and $Z_0$ are selected such that the tandem Arg-Gly-Glu sequences in Formula I adopt a conformation where they are adjacent and anti-parallel to each other.

In preferred embodiments, the invention provides cyclic peptides according to Formula II that have the formula

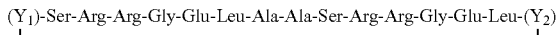

where the elements $Y_1$ and $Y_2$ are as set forth, supra, for Formula II. Particularly preferred peptides according to Formula II, which are also a part of the present invention, are cyclic peptides comprising the amino acid sequence: CSRRGELAASRRGELC (SEQ ID NO:17) and N-Ac-CSRRGELAASRRGELC-NH$_2$ (SEQ ID NO:18), (where the underlined portion of each amino acid sequence indicates that portion of the peptide that is cyclized).

In accordance with the invention, cyclic peptides are provided comprising, within a cyclic ring of the cyclic peptide, the D amino acid sequence:

dGlu-Gly-dArg wherein the cyclic peptide modulates Trk receptor mediated activity. Preferred cyclic peptides that modulate Trk receptor mediated activity comprising D amino acid sequences are c[dLdEGdRdRdSdLdEGdRdRdS] (SEQ ID NO:40), (where the bracketed portion of the amino acid sequence indicates that portion of the peptide that is cyclized by a peptide bond) and Ac-dCdLdEGdRdRdSdAdAdLdEGdRdRdSdC-NH$_2$ (SEQ ID NO:41).

In a further embodiment, the invention provides the cyclic peptide having the amino acid sequence c[SRRGELSRRGEL] (SEQ ID NO:39).

In addition to the cyclic peptides, the invention also provides methods for identifying other compounds (i.e., "candidate compounds") that modulate Trk receptor mediated activity or are likely to modulate such activity. These methods involve comparing a three-dimensional structure of the candidate compound with the three-dimensional structure of a cyclic peptide of the invention. Similarity between the structure of the candidate compound and the structure of the cyclic peptide is indicative of the candidate compound's ability to modulate Trk receptor mediated activity. Hence, a candidate compound having a substantially similar structure to the three-dimensional structure of the cyclic peptide is likely to be a compound which modulates Trk receptor mediated activity.

The above methods are ideally suited for identifying peptidomimetic compounds that modulate Trk receptor mediated activity. Accordingly, the invention provides peptidomimetic compounds that are Trk modulators, and such compounds are considered another aspect of the invention. In particular, the peptidomimetic compounds of the invention are compounds having a three-dimensional structure that is substantially similar to the three-dimensional structure of a cyclic peptide of the invention (i.e., a cyclic peptide that modulates Trk mediated activity and comprises, within a cyclic ring thereof, the amino acid sequence Arg-Gly-Glu).

The invention additionally provides methods, including therapeutic methods, that use cyclic peptides and peptidomimetic compounds to modulate Trk mediated activity. In one such embodiment, the invention provides methods for inhibiting Trk mediated activity. Such methods involve contacting a cell (in vitro or in vivo) with an amount of a cyclic peptide or peptidomimetic compound of the invention that inhibits Trk mediated activity. The amount of the cyclic peptide or peptidomimetic compound contacted to the cell should be an amount that effectively inhibits the Trk receptor mediated activity.

In another embodiment, the invention provides methods for enhancing Trk mediated activity. Such methods involve contacting a cell (in vitro or in vivo) with an amount of a cyclic peptide or peptidomimetic compound of the invention that enhances Trk mediated activity. The amount of the cyclic peptide or peptidomimetic compound contacted to the cell should be an amount that effectively enhances the Trk receptor mediated activity.

Examples of Trk mediated activities that can be modulated (e.g., enhanced or inhibited) by such methods include: neuronal growth and survival, axonal growth, neurite outgrowth and synaptic plasticity and well as other processes of central nervous system (CNS) growth and/or repair. Accordingly, the invention additionally provides methods for enhancing growth or repair of the central nervous system in an individual. These methods involve administering to the individual an amount of a cyclic peptide or a peptidomimetic compound of the invention that enhances Trk mediated activity. The amount of the cyclic peptide or peptidomimetic compound administered should be an amount that effectively enhances CNS growth or repair.

The invention additionally provides methods that use Trk agonists and antagonists to modulate responses that inhibit CNS growth and repair, including responses that normally inhibit processes such as neuronal growth, neuronal survival, axonal growth, neurite outgrowth and synaptic plasticity. In particular, Trk agonists and antagonists of the invention can be used to modulate inhibitory factors and/or inhibitory signals generated by such factors. Examples include factors associated with myelin, including the myelin associated glycoprotein (MAG), Nogo-A and the oligodendrocyte myelin glycoprotein. In general, the invention provides methods using Trk agonists and/or antagonists to modulate a CNS inhibitor response mediated by a signal cascade with one or more components that are themselves modulated by a factor or factors involved in signaling by a Trk receptor. These include, for example, components such as Rho that are modulated by protein kinase A (PKA) and/or by phosphoinositide-3 kinase (PI3K). In preferred embodiments, therefore, the invention provides methods for reducing such "CNS inhibitor" responses by contacting a cell with a Trk agonists (e.g., a cyclic peptide or peptidomimetic) of the invention in an amount that is effective for reducing the CNS-inhibitor response. The invention also provides methods for reducing a CNS inhibitor response in an individual, by administering to the individual an amount of a Trk agonists (e.g., a cyclic peptide or peptidomimetic) of the invention in an amount that effectively reduces the CNS inhibitor response.

In still other embodiments, the invention provides pharmaceutical compositions that can be used in therapeutic methods, such as those described above. Such pharmaceutical compositions comprise an amount of a cyclic peptide or peptidomimetic compound of the invention, along with one or more carriers, diluents or excipients that are pharmaceutically and/or physiologically acceptable.

Further, the present invention is based on the discovery that agents which interfere with the binding of neurotrophins to the p75 receptor promote CNS neuron growth in an inhibitory environment.

Trk receptors and their ligands (i.e. neurotrophins such as NGF, BDNF, NT-3, NT-4 and NT-5) are associated with the growth and repair of CNS neurons. As such, when neurotrophins bind to and activate Trk receptors, Trk activity triggers signaling cascades which promote neuronal growth. However, the p75 receptor binds neurotrophins with low affinity and, when the p75 receptor is engaged in an inhibitory complex, this interaction compromises the ability of neurotrophins to promote CNS neuron growth. The invention provides methods for promoting CNS neuron growth using a p75 receptor binding agent, which interferes with the binding of a neurotrophin to the p75 receptor.

According to the present invention, a method is provided for promoting CNS neuron growth in an inhibitory environment, which comprises administering to an individual a therapeutically effective amount of a p75 receptor binding agent. In one embodiment, the p75 receptor binding agent includes a neurotrophin binding motif or a peptidomimetic thereof. In a particular embodiment, the p75 receptor binding agent comprises a cyclic peptide or peptidomimetic comprising, within a cyclic ring thereof, the amino acid sequence Thr-Asp-Ile-Lys-Gly-Lys-Glu (TDIKGKE) (SEQ ID NO:42). A preferred p75 receptor binding agent is N-Ac-CTDIKGKEC-NH$_2$ (SEQ ID NO:43). The individual is preferably a mammal and more preferably a human.

The present invention provides methods for promoting CNS neuron growth in an inhibitory environment, which comprise administering to an individual a therapeutically effective amount of a p75 receptor binding agent in combination with a neurotrophin. In one embodiment, the neurotrophin is selected from the group consisting of NGF, BDNF, NT-3, NT-4 and NT-5. In a further embodiment, the p75 receptor binding agent is administered in an amount about 10 to about 100 fold greater than the neurotrophin. In an aspect of the invention, the p75 receptor binding agent is a neurotrophin that interferes with another, different neurotrophin for binding to the p75 receptor, but does not interfere with binding of the another, different neurotrophin to a Trk receptor expressed on an injured neuron. In a particular aspect, the p75 receptor binding agent is NGF and the neurotrophin is BDNF wherein NGF is administered in an amount about 10 to about 100 fold greater than BDNF. The individual is preferably a mammal, and more preferably, a human.

5. BRIEF DESCRIPTION OF THE DRAWINGS

FIG. 1 shows the amino acid sequence alignment of NTs BDNF (SEQ ID NO:19), NT4 (SEQ ID NO:20), NT3 (SEQ ID NO:21), and NGF (SEQ ID NO:22). Mature chains are denoted by bold lettering and the RGE motif is underlined.

Figure 2A:
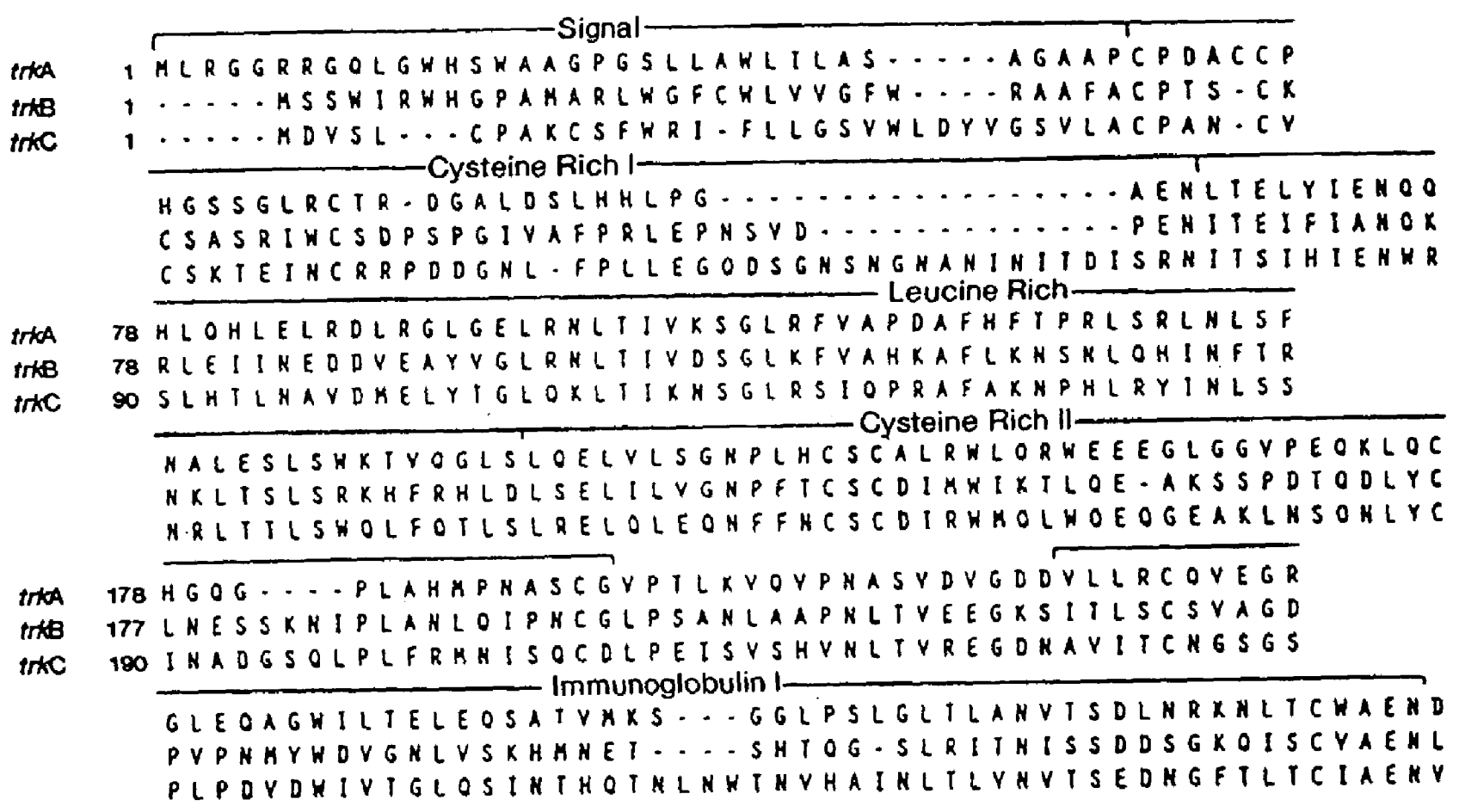
Figure 2C:
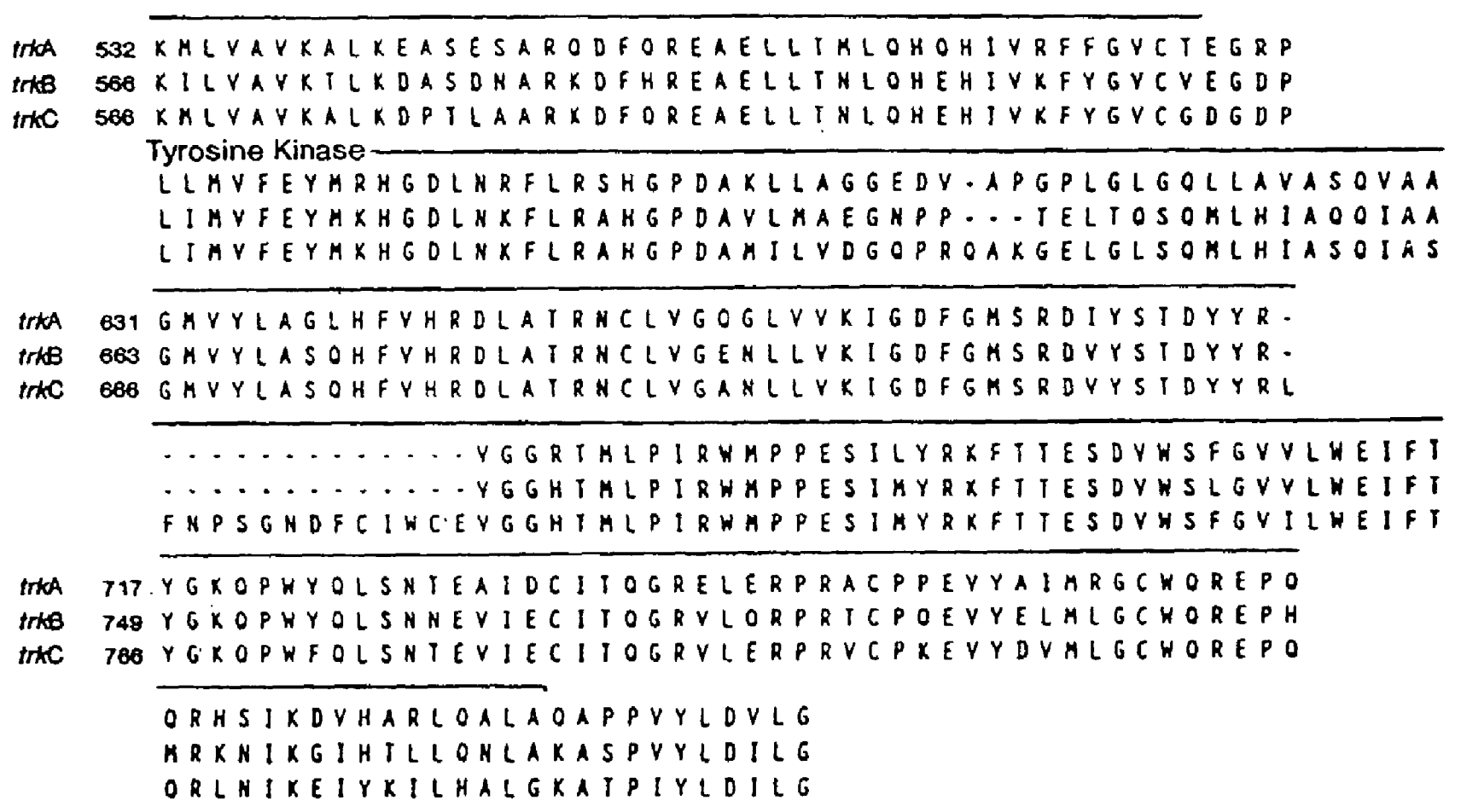

FIGS. 2A–2C show an alignment of the full length amino acid sequences of human TrkA (SEQ ID NO:23), TrkB (SEQ ID NO:24) and TrkC (SEQ ID NO:25) receptors. Consensus sequences for the receptors are boxed, and the boundaries of the receptors' various domains are marked by vertical lines. See also, U.S. Pat. No. 5,844,092 by Presta et al.

FIGS. 3A–3B illustrate representative backbone modifications that may be present within a peptidomimetic. See also, FIGS. 4A and 4B in WO 01/53331.

FIG. 4 illustrates representative unusual amino acids and dipeptide surrogates that may be incorporated into a peptidomimetic. See also, FIG. 5 in WO 01/53331.

FIG. 5 illustrates representative secondary structure mimics that may be incorporated into a peptidomimetic. See also, FIG. 6 in WO 01/53331.

Figure 6:
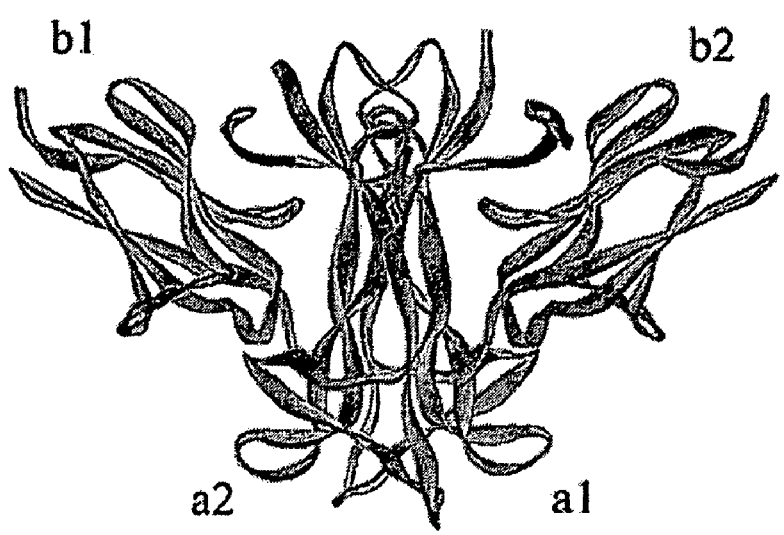
Figure 6:
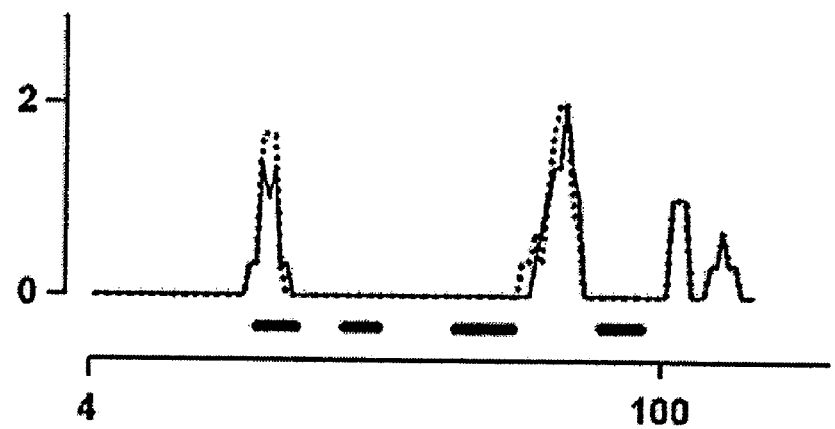
Figure 6:
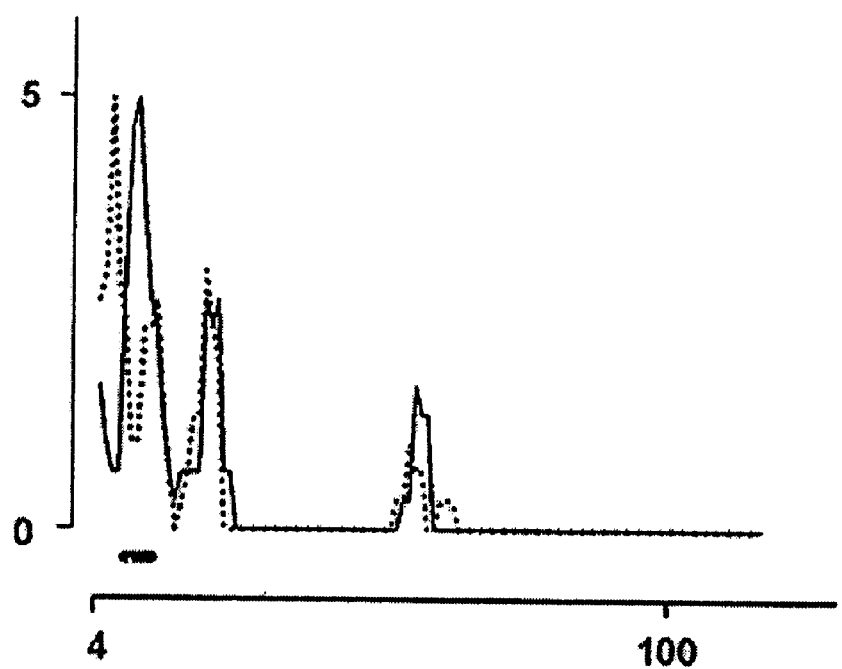

FIGS. 6A–6C illustrates the analysis of a NT/Trk crystal structure to identify linear regions of the ligand that interact with the Trk receptor. FIG. 6A shows a ribbon image of the crystal structure (reported by Banfield et al., *Structure (Camb)* 2001, 9:1191–1199) of an NT-4 dimer (denoted as chain a$_1$ and a$_2$) in a complex with two membrane proximal Ig domains from the TrkB receptor (denoted as chain b$_1$ and b$_2$). FIG. 6B shows the results of examining this crystal structure (solid line) and the NGF/TrkA crystal structure (reported by Wiesman et al., *Nature* 1999, 401:184–188) (dotted line) for linear peptide sequences (LIPs) that make contact between the a$_1$ and b$_2$ chains. FIG. 6C shows the results of examining the NGF (dotted line) and NT-4 (solid line) crystal structures for LIPs that make contact between the a$_1$ and b$_1$ chains.

Figure 7:
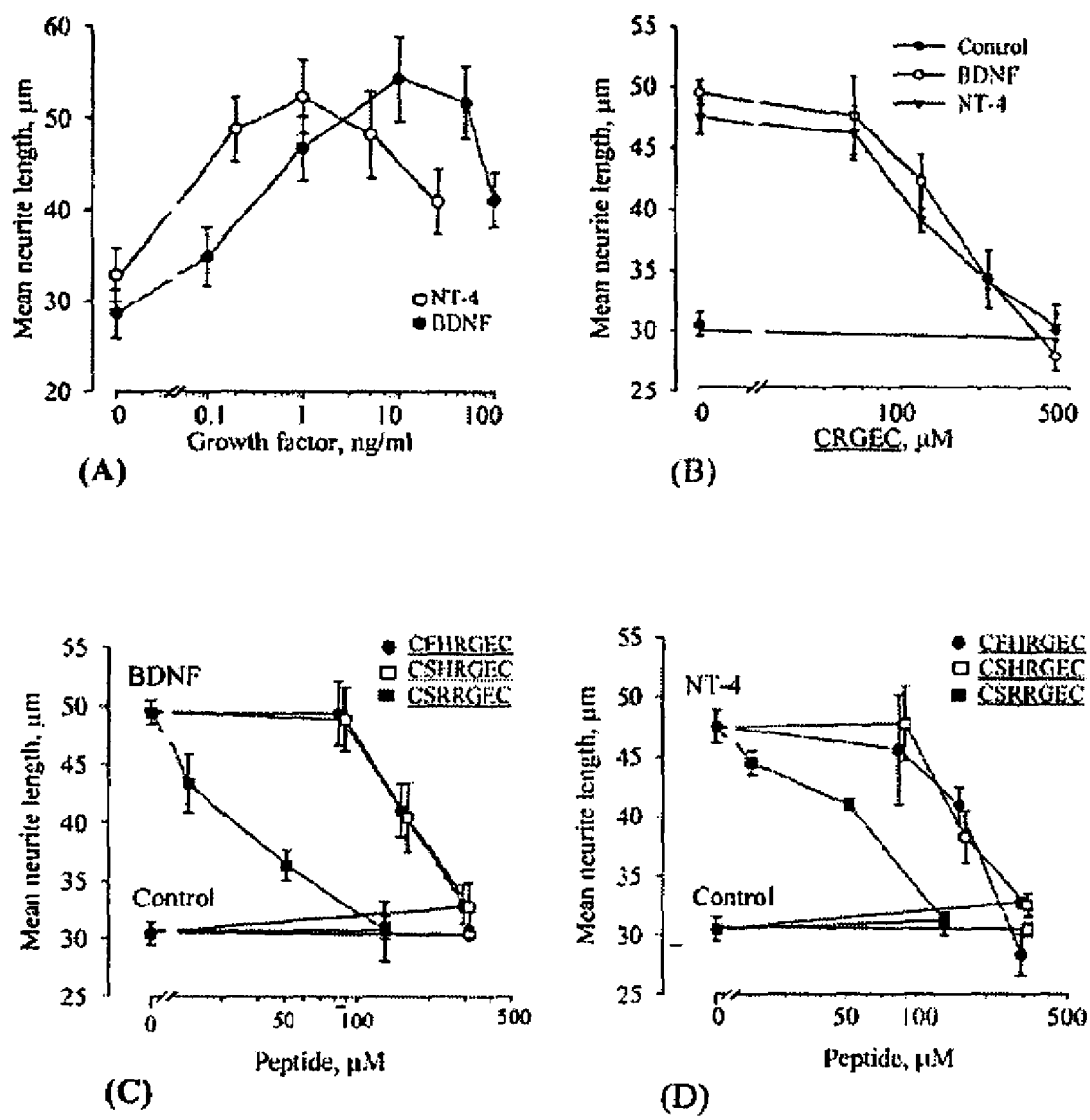

FIGS. 7A–7D show data from experiments where cerebellar neurons were cultured over monolayers of 3T3 cells in control media or in media supplemented with NT-4 or BDNF in the presence of various peptides for 18 hours before being fixed and stained for GAP-43. The mean length of the longest neurite was determined from between about 100–120 neurons under each culture condition. FIG. 7A shows data from experiments testing the effects of various concentrations of NT-4 and BDNF on neurite outgrowth. FIG. 7B shows data from experiments testing the effects of increasing concentrations of the cyclic peptide N-Ac-CRGEC-NH$_2$ (SEQ ID NO:10) in control media and in media containing 5 ng/ml BDNF or 5 ng/ml NT-4, as indicated. FIG. 7C shows data from experiments testing the effects of the NT-4 derived cyclic peptide N—Ac-CSRRGEC-NH$_2$ (SEQ ID NO:26), the NT-3 derived cyclic peptide N-Ac-CSHRGEC-NH$_2$ (SEQ ID NO:7 with an acetylated N-terminal amino group and C-terminal amide group) and the NGF derived cyclic peptide N-Ac-CFHRGEC-NH$_2$ (SEQ ID NO:6) in cerebellar neurons cultured with 5 ng/ml BDNF. FIG. 7D shows data from experiments identical to that shown in FIG. 7C, but where the cerebellar neurons are cultured with 5 ng/ml NT-4.

Figure 8:
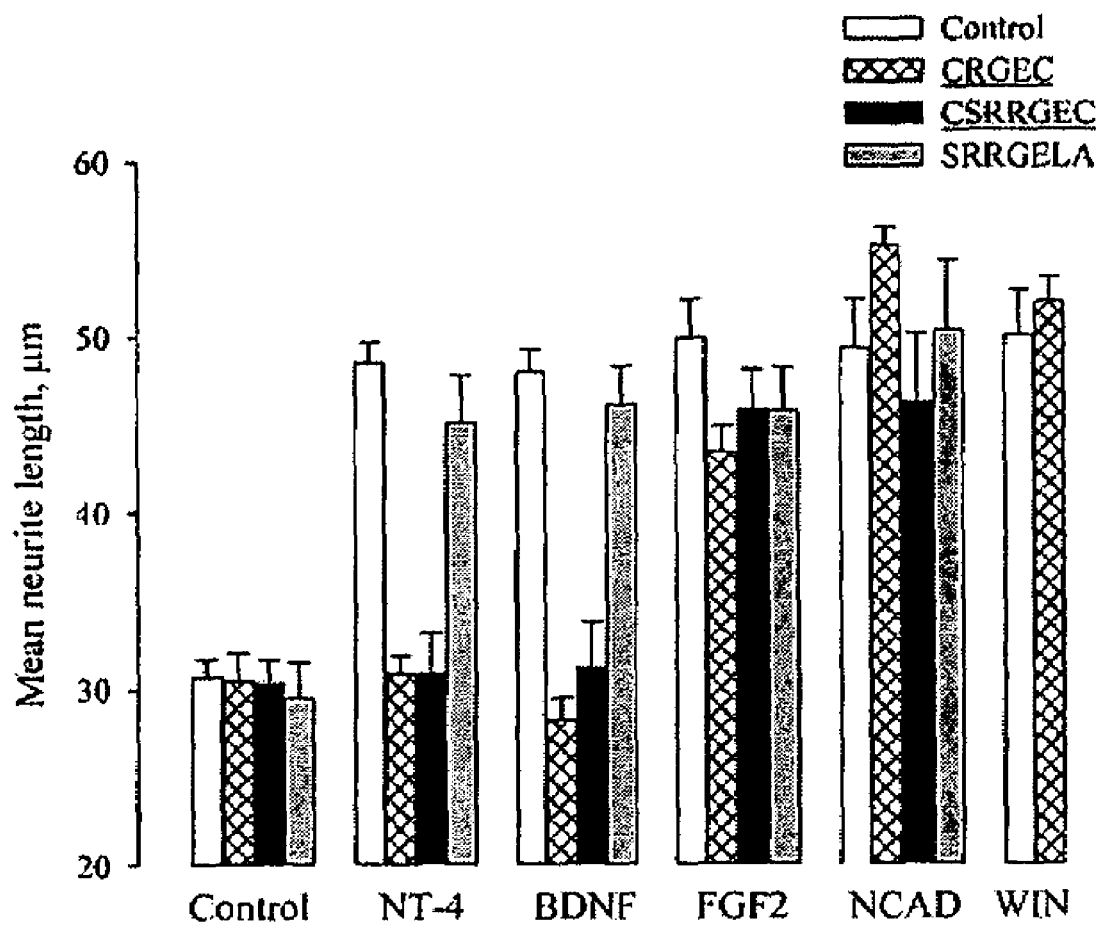

FIG. 8 illustrates results from experiments were cerebellar neurons were cultured over monolayers of 3T3 cells in control media or in media supplemented with NT-4, BDNF, FGF2 (all at 5 ng/ml), with the CG1 receptor agonist WIN55,2122-2 (0.2 µM) or over monolayers of 3T3 cells the express transfected N-cadherin (NCAD) on their cell surface. The experiments were performed, and data plotted, in the presence and absence of: (a) the cyclic peptide N-Ac-CRGEC-NH$_2$ (SEQ ID NO:10) at 440 µM; (b) the cyclic peptide N-Ac-CSRRGEC-NH$_2$ (SEQ ID NO:2) at 125 µM; and (c) the linear peptide N-Ac-SRRGELA-NH$_2$ (SEQ ID NO:27) at 125 µM.

Figure 9A:
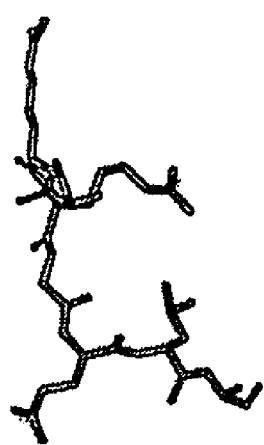
Figure 9B:
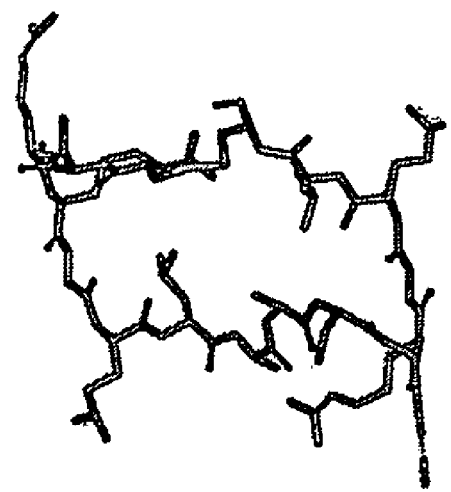
Figure 9C:
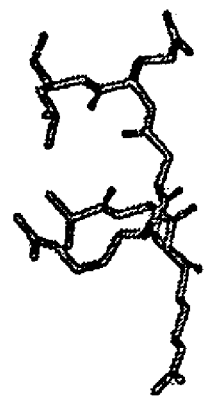

FIGS. 9A–C show modeled structures of the B$_{AG}$ peptide. FIG. 9A shows the native structure of the SRRGELA (SEQ ID NO:27 without an acetylated N-terminal amino group and a C-terminal amide group) motif from one monomer of the NT-4 dimer in the NT-4/TrkB crystal structure. The native structure of the ASRRGEL (SEQ ID NO:28) motif from the partner NT-4 monomer in that crystal structure is shown in FIG. 9C. A modeled structure of the B$_{AG}$ peptide N-Ac-CSRRGELAASRRGELC-NH$_2$ (SEQ ID NO:18) incorporating these "tandem-repeat" motifs is shown in FIG. 9B.

Figure 10A:
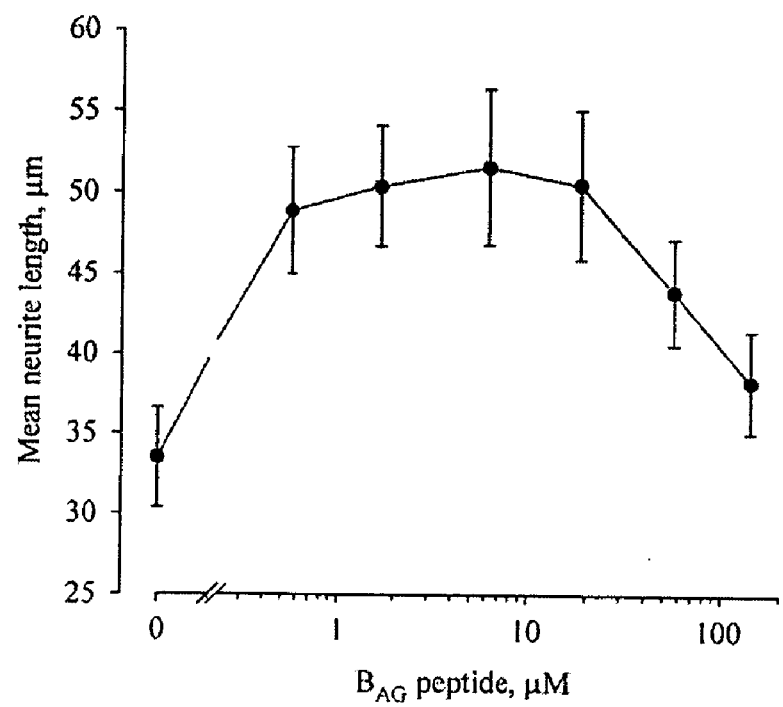
Figure 10B:
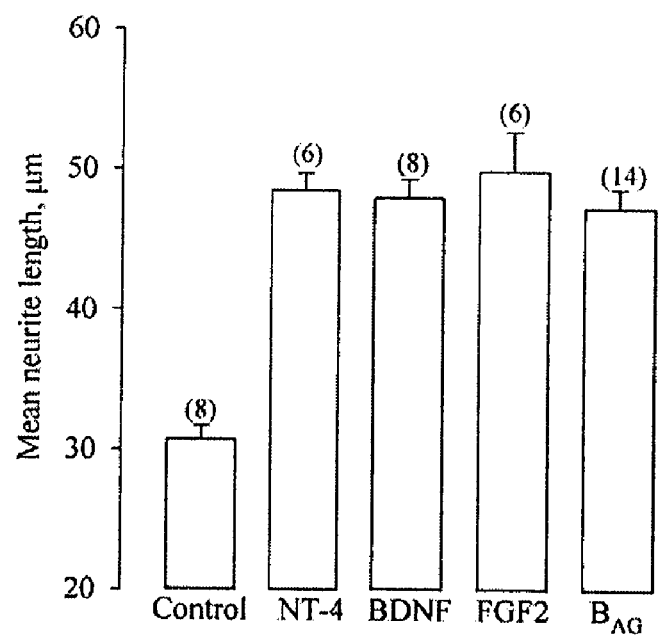

FIGS. 10A–10B show results from neurite outgrowth experiments where cerebellar neurons were cultured in media supplemented with a range of concentrations of the B$_{AG}$ peptide N—Ac-CSRRGELAASRRGELC-NH$_2$ (SEQ ID NO:18). FIG. 10A shows the mean value of absolute neurite lengths determined from 100–120 neurons sampled in a single experiment. FIG. 10B shows a histogram comparing effects of the B$_{AG}$ peptide (6 µM) with the response to established growth promoting agents, including NT-4, BDNF, and FGF2 (all at 5 ng/ml) as indicated.

Figure 11:
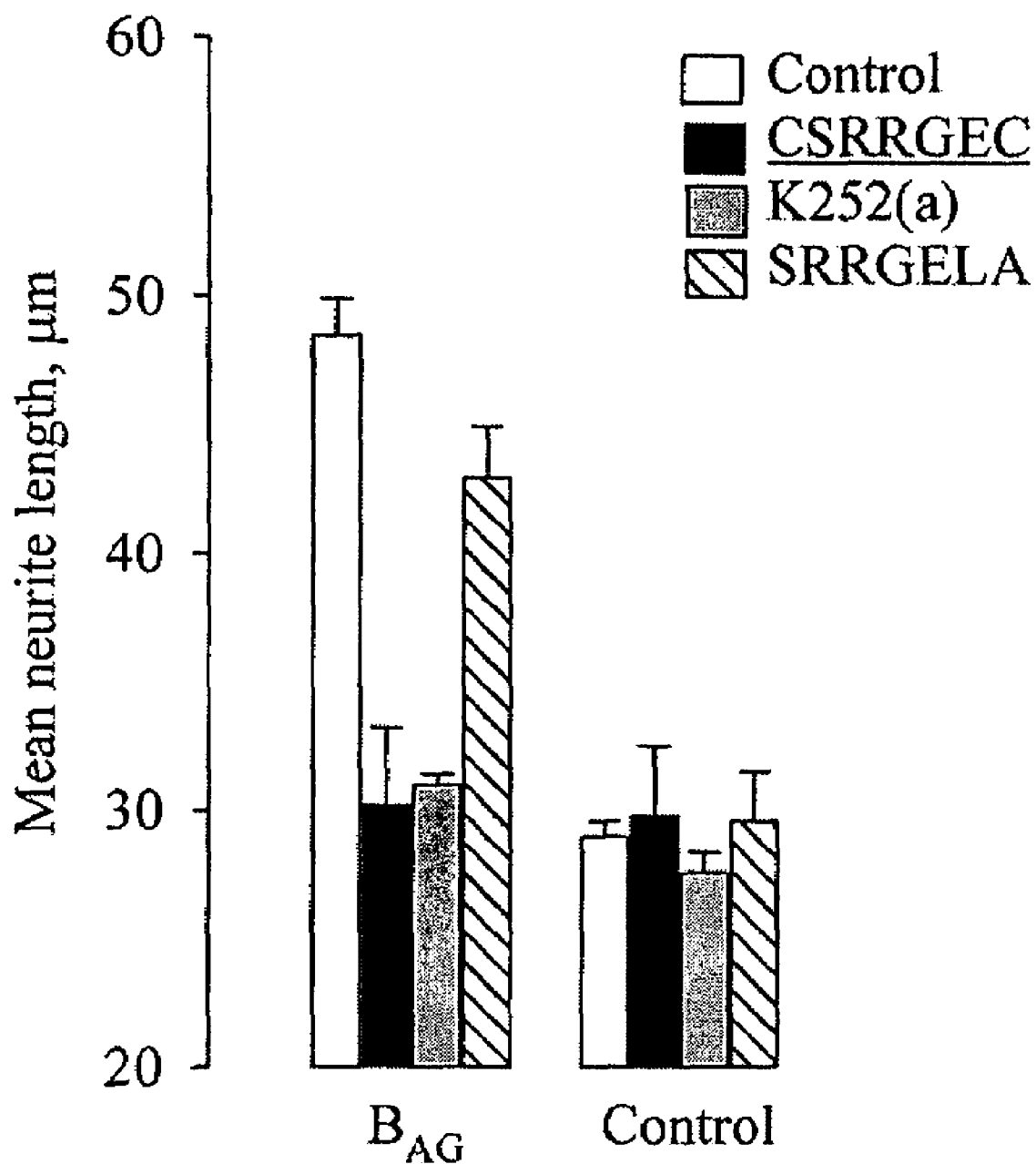

FIG. 11 shows results from neurite outgrowth experiments where cerebellar neurons were cultured in control media or in media supplemented with: (a) the B$_{AG}$ peptide N-Ac-CSRRGELAASRRGELC-NH$_2$ (SEQ ID NO:18) at 6 µM; (b) the TrkB antagonist peptide N-Ac-CSSRGEC-NH$_2$ (SEQ ID NO:29) at 125 µM; (c) the Trk specific tyrosine kinase inhibitor K252a at 100 nM; or the linear version of the TrkB antagonist peptide N-Ac-SRRGELA-NH$_2$ (SEQ ID NO:27) at 125 µM, as indicated.

Figure 12:
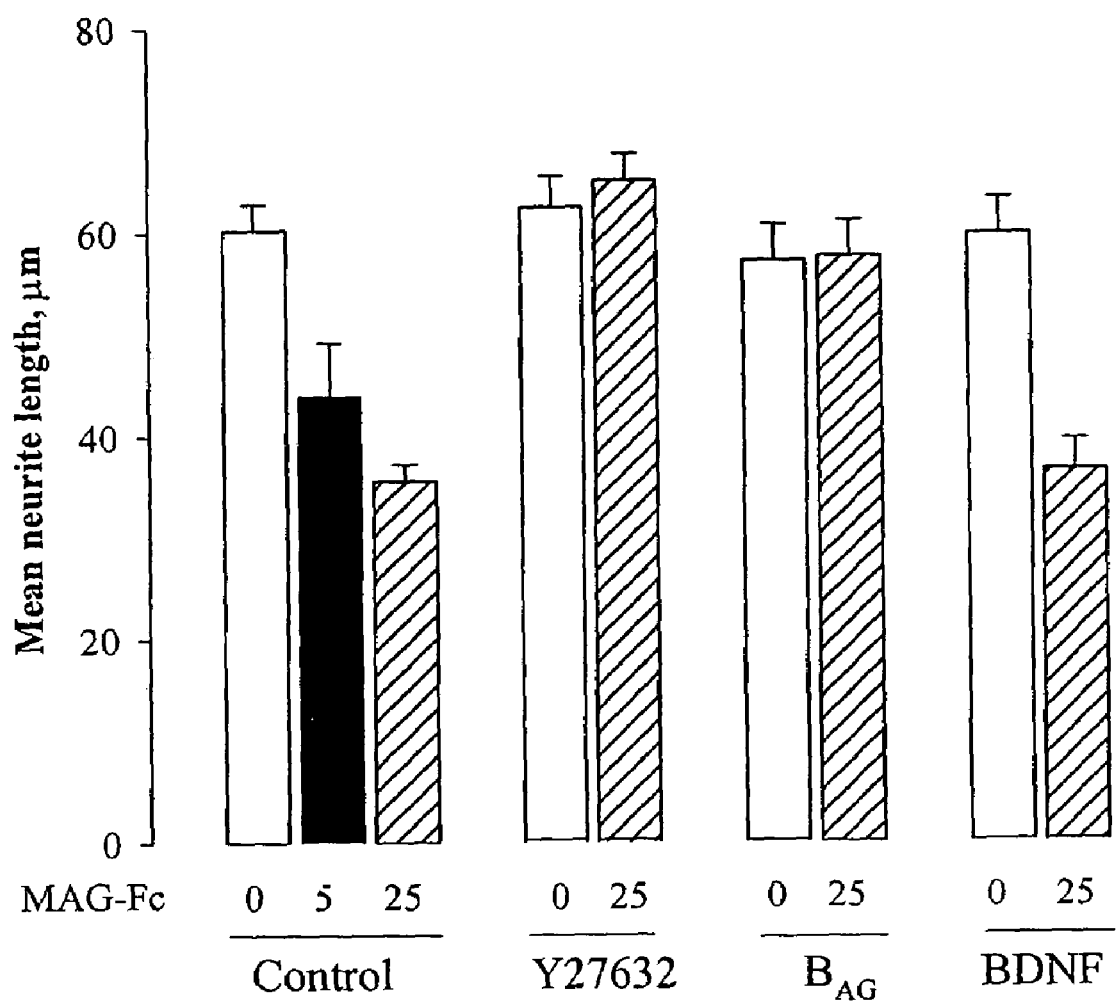

FIG. 12 shows a bar graph depicting results from neurite outgrowth experiments testing the effects of various agents. In particular, cerebellar neurons were cultured over monolayers of N-cadherin expressing 3T3 cells in media supplemented with a soluble MAG-Fc fusion construct at final concentrations of 0, 5 or 25 µg/ml (as indicated below each bar in the graph). Experiments were done in control media (i.e., in media supplemented with MAG-Fc only) and in media additionally supplemented with the Rho kinase inhibitor Y27632 (10 µM final concentration) B$_{AG}$ polypeptide (6 µM final concentration) or BDNF (5 ng/ml final concentration). Cultures were maintained for 22 hours before being fixed and stained for GAP-43. The mean length of the longest neurite was determined from measurements of between about 100–120 neurons under each culture condition. Each column of the graph depicts pooled results from a number of independent experiments (indicated above the column), and the bars indicate standard error of the mean (SEM).

Figure 13:
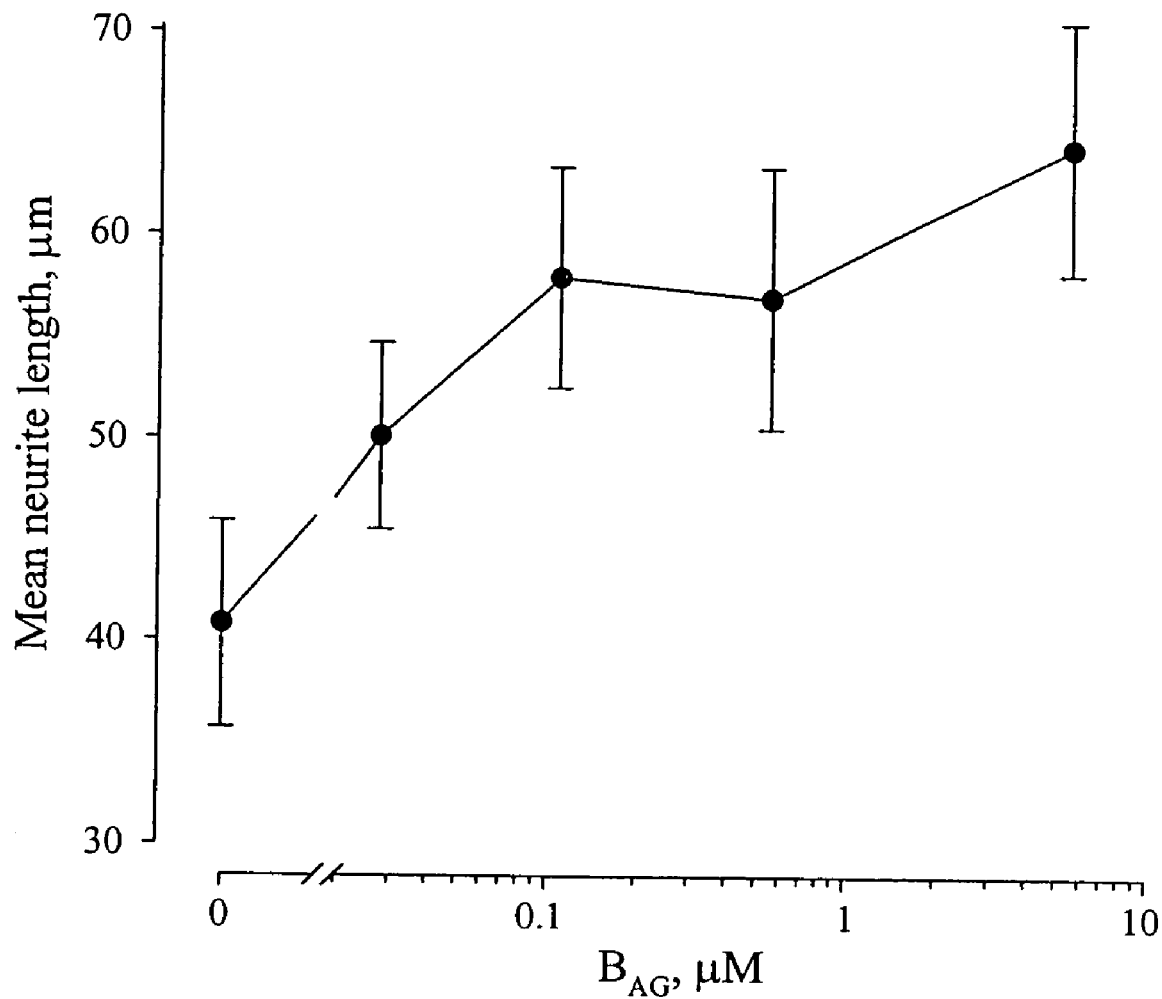

FIG. 13 illustrates a dose response curve for B$_{AG}$ polypeptide on the MAG-Fc response in cultured neurons. In particular, each data point indicates the mean length measured from about 120–150 neurons when cultured over monolayers of N-cadherin expressing 3T3 cells in media supplemented with MAG-Fc (25 µg/ml final concentration) and B$_{AG}$ polypeptide at the final concentration indicated on the horizontal axis. Each point indicates data from a single, representative experiment and the bars on each point indicate the SEM.

Figure 14:
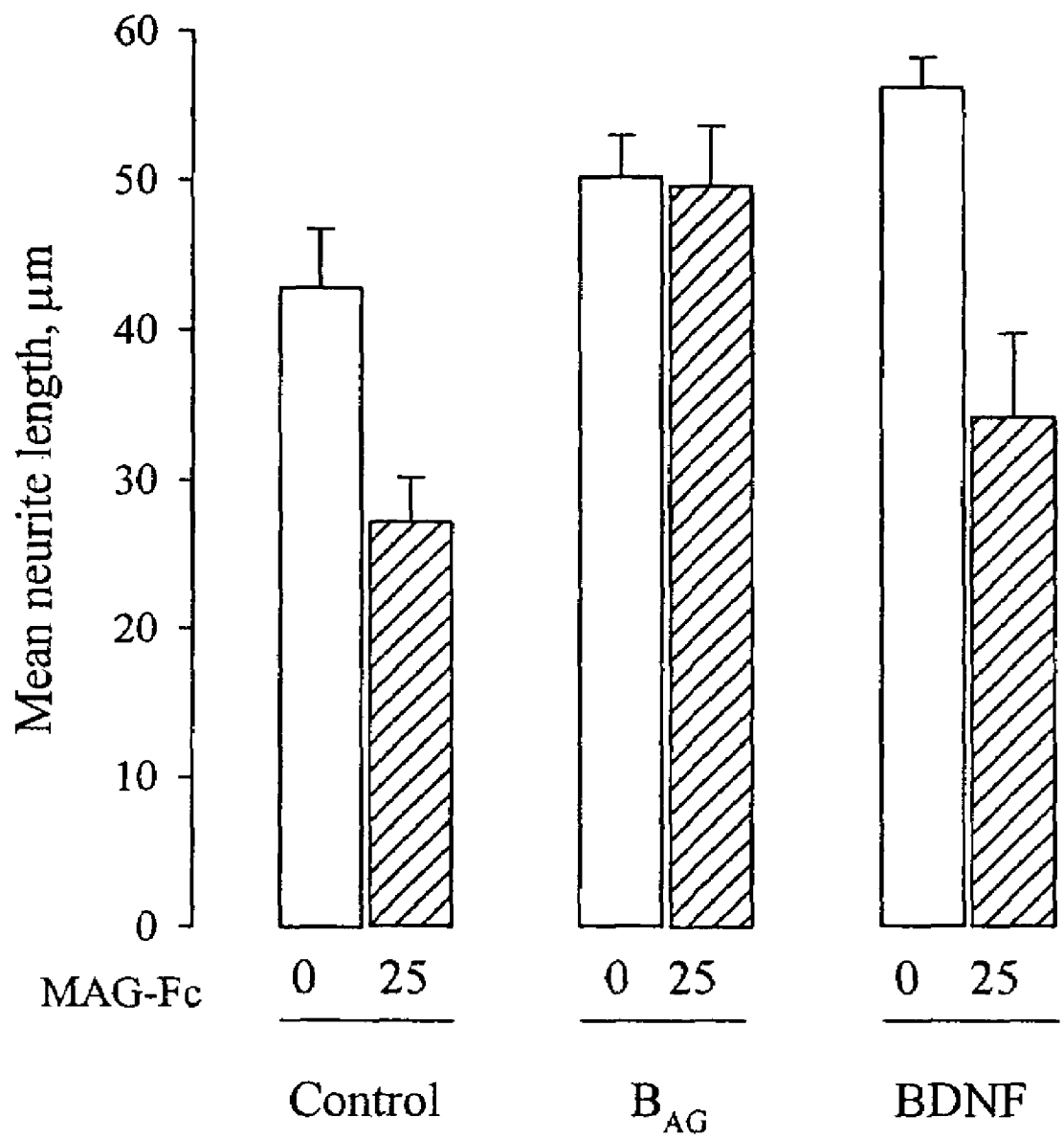

FIG. 14 shows a bar graph depicting results from experiments testing the effects of B$_{AG}$ polypeptide and BDNF on neurite outgrowth in cerebellar neurons that were cultured over monolayers of 3T3 cells that do not express N-cadherin and in media supplemented with 0 or 25 µg/ml final concentration MAG-Fc (as indicated in the figure). Experiments were done in control media (i.e., in media supplemented with MAG-Fc only) and in media additionally supplemented with B$_{AG}$ polypeptide (6 µM final concentration) or BDNF (5 ng/ml final concentration). Cultures were maintained for 22 hours before being fixed and stained for GAP-43. The mean length of the longest neurite was determined from measurements of between about 100–120 neurons under each culture condition. Each column of the graph depicts pooled results from three independent experiments, and the bars indicate standard error of the mean (SEM).

Figure 15:
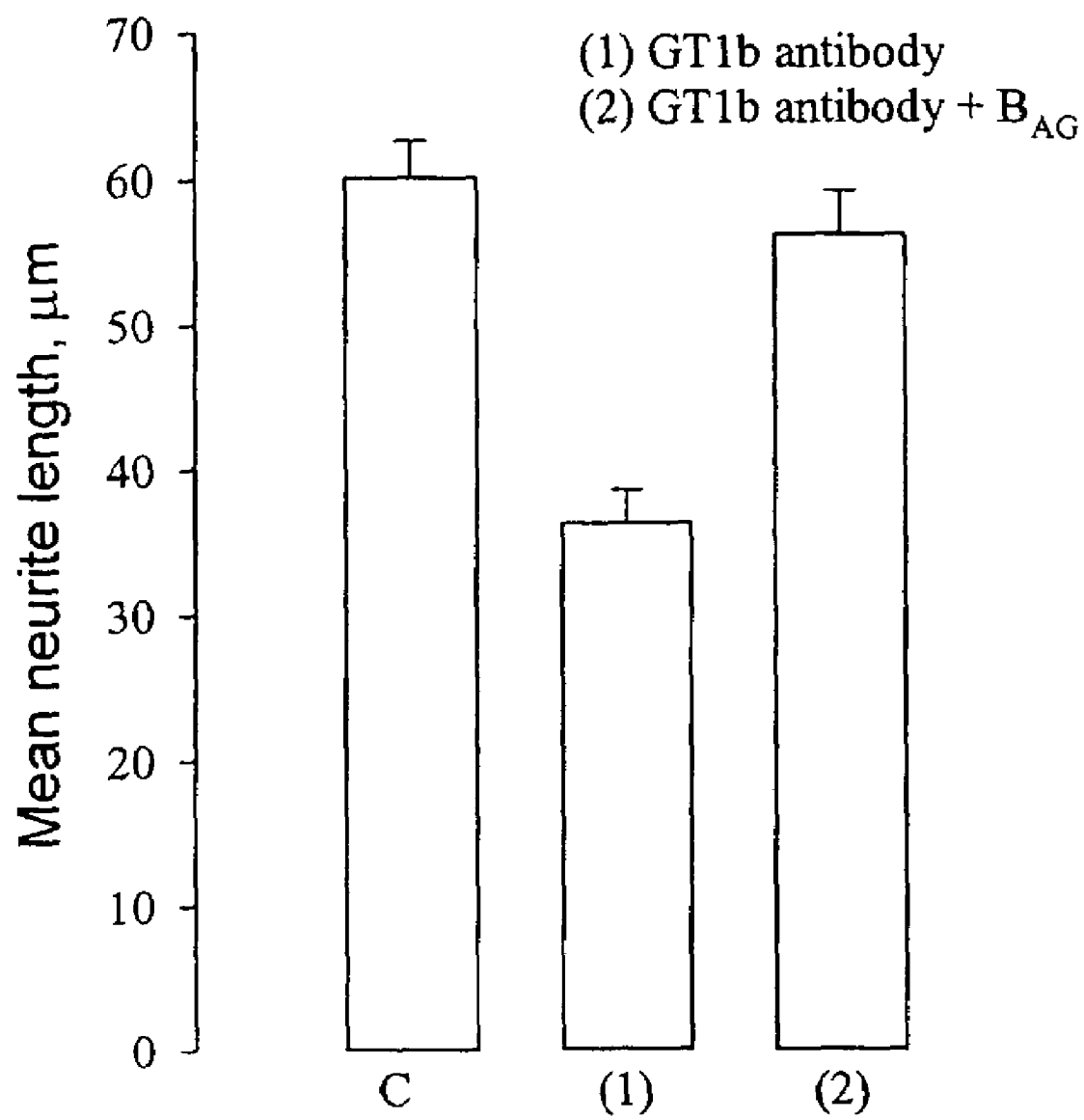

FIG. 15 shows a bar graph depicting results from experiments testing the B$_{AG}$ polypeptide's effect on neurite outgrowth in cerebellar neurons that were cultured over monolayers of N-cadherin expressing 3T3 cells in either: (C) control media without supplements; (1) media supplements with monoclonal antibody for GT1b (20 µg/ml final concentration); or (2) media supplemented with both the GT1b antibody (20 µg/ml final concentration) and B$_{AG}$ polypeptide (6 µM final concentration). Cultures were maintained for 22 hours before fixing and staining for GAP-43. The mean length of the longest neurite was determined from between about 100 and 120 neurons under each culture condition. Each column in the figure indicates pooled results from between 7 and 10 independent experiments, and the bars on each column indicate the SEM.

Figure 16:
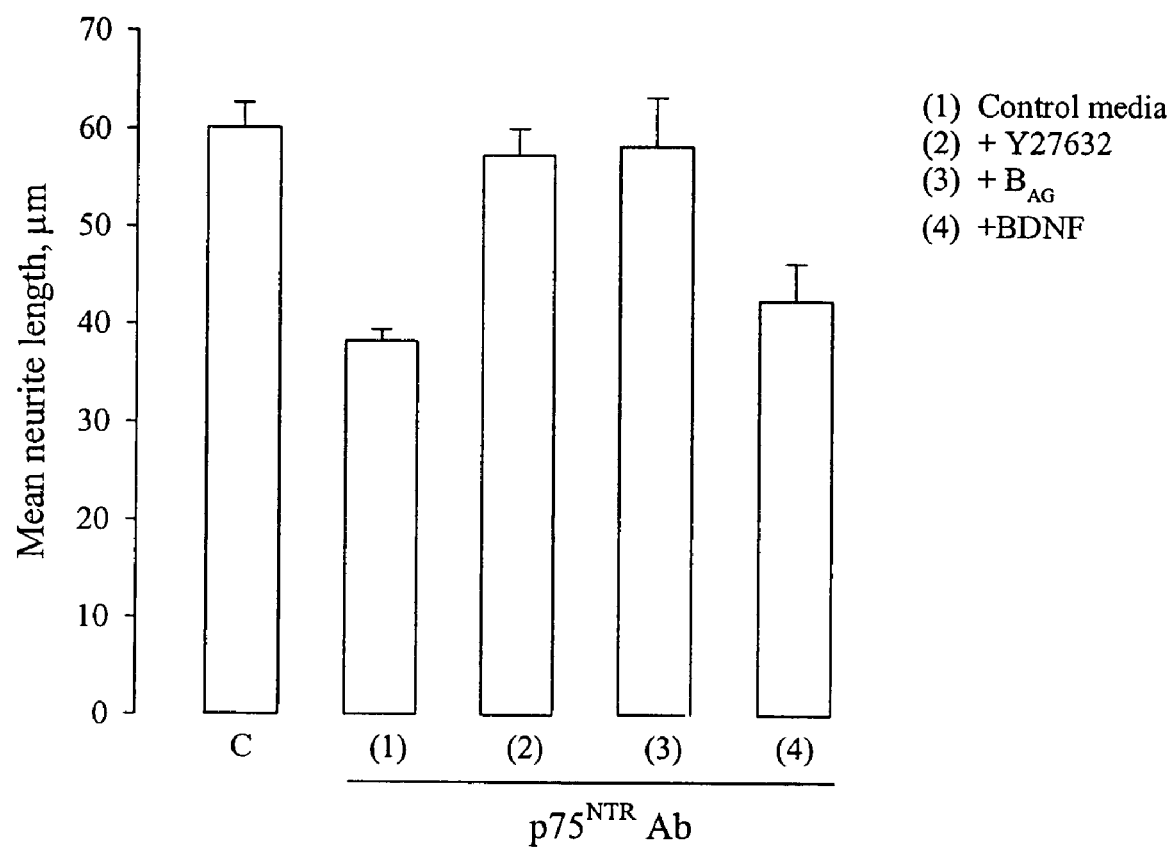

FIG. 16 shows a bar graph depicting results from experiments testing the effects of various agents on neurite outgrowth in cerebellar neurons that were cultured over monolayers of N-cadherin expressing 3T3 cells either in control media without supplements (column C) or in media pre-treated with antibody to p75$^{NTR}$ (columns 1–4). These antibody treated neurons were cultured after treatment in either: (1) control media without supplements; (2) the Rho kinase inhibitor Y27632 (10 µM final concentration); (3) B$_{AG}$ polypeptide (6 µM final concentration); or (4) BDNF neurotrophin (5 ng/ml final concentration). Cultures were maintained for 22 hours before being fixed and stained for GAP-43. The mean length of the longest neurite was determined from between about 100 and 120 neurons under each culture condition. Each column in the figure indicates pooled results from the number of independent experiments indicated above it, and the bars on each column indicate the SEM.

Figure 17:
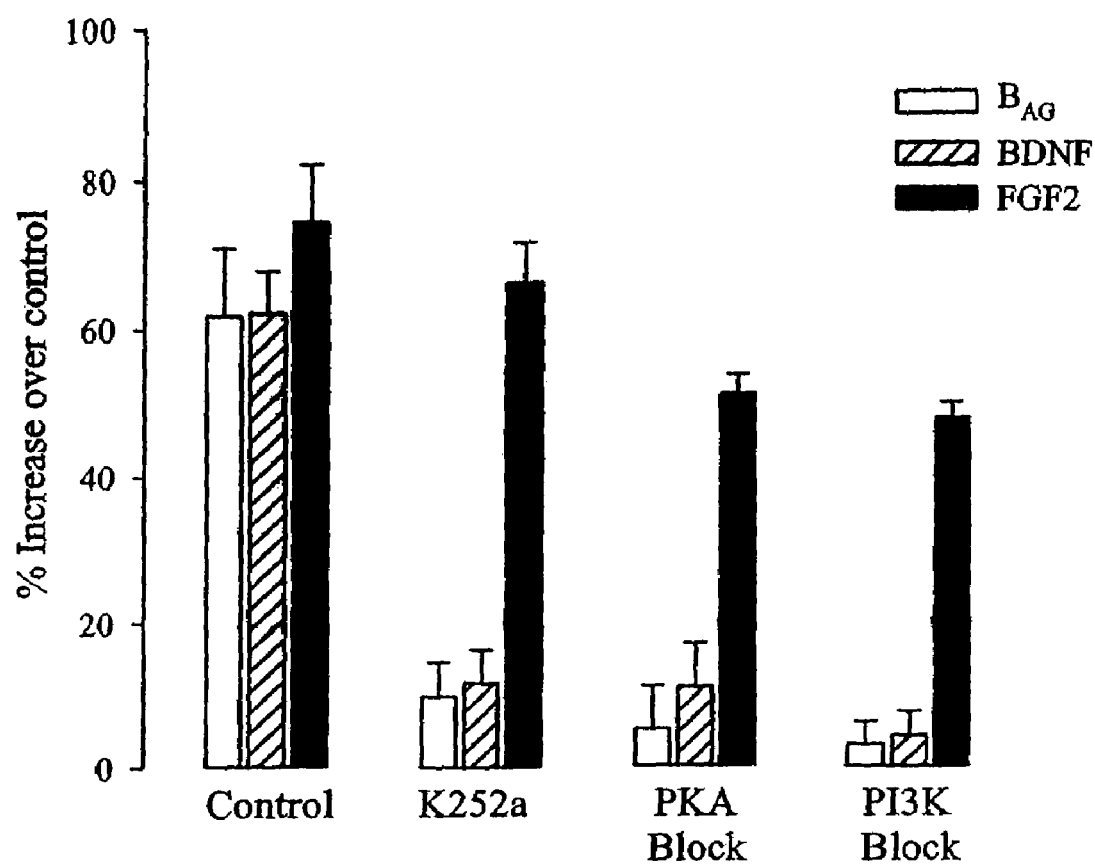

FIG. 17 shows a bar graph depicting results from experiments testing the effects of various kinase inhibitors on neurite outgrowth in cerebellar neurons cultured under different conditions. In particular, cerebellar neurons were cultured over monolayers of 3T3 cells in media supplements with either B$_{AG}$ polypeptide at a final concentration of 6 µM (blank bars), BDNF neurotrophin at a final concentration of 5 ng/ml (striped bars) or FGF2 at a final concentration of 5 ng/ml (black bars). To test the effects of various agents, the experiments were done as indicated in the figure using control media containing no additional supplements, or using media additionally supplement with K252a (100 nM final concentration), a PKA inhibitor (KT5720 at 200 nM final concentration or H-89 at 400 nM final concentration), or a PI3K inhibitor (Wortmannin or Ly294002, each at a final concentration of 10 μM). Cultures were maintained for 18 hours before being fixed and stained for GAP-43, and the mean length of the longest neurite was determined from between about 100 and 120 neurons under each culture condition. Data are pooled for results obtained with each of the PKA inhibitors and each of the PI3K inhibitors (which produced the same results). Each column in the figure indicates pooled results from at least three independent experiments, and the bars on each column indicate the SEM.

FIGS. 18A–18B show graphs depicting the results from experiments testing the effects on neurite growth in cerebellar neurons that were cultured in an "inhibitory environment" of wells coated with polylysine at 17 μg/ml in distilled water ($dH_2O$); a mixture of goat anti-human IgG (Fc-specific) and fibronectin (both at 10 μg/ml in DMEM); and MAG-Fc at 0.25 μg/ml in DMEM/10% FCS. Cultures were maintained for 27 hours before being fixed and stained for GAP-43. FIG. 18A shows a dose-response curve of mean neurite length of cerebellar neurons grown in the presence of $hriB_{AG2}$, $hB_{AG2}$ or $riB_{AG}$.

FIG. 18B shows a bar graph depicting the mean neurite length of cerebellar neurons grown in the presence of BDNF, $B_{AG}$, $hriB_{AG2}$, $hB_{AG2}$ or $riB_{AG}$.

FIG. 19 shows a bar graph depicting results from neurite outgrowth experiments testing the effects of various agents in an inhibitory environment. In particular, cerebellar neurons were cultured over monolayers of N-cadherin expressing 3T3 cells in media supplemented with a soluble MAG-Fc fusion construct at a final concentration of 25 μg/ml. The culture was further supplemented with BDNF (1 ng/ml), NGF (10 ng/ml or 100 ng/ml), BDNF (1 ng/ml) in combination with NGF (10 ng/ml or 100 ng/ml), a constrained monomer of the NGF loop 1 binding motif (N-Ac-CTDIKGKEC-$NH_2$) (SEQ ID NO:43) at 100 μg/ml, or the NGF loop 1 peptide (at 100 μg/ml) in combination with BDNF (at 1 ng/ml). Cultures were maintained for 23 hours before being fixed and stained for GAP-43. The mean length of the longest neurite was determined from measurements of between about 100–120 neurons under each culture condition. Each column of the graph depicts pooled results from a number of independent experiments (indicated above the column), and the bars indicate standard error of the mean (SEM).

6. DETAILED DESCRIPTION

As noted above, the present invention provides compounds, including peptides and peptidomimetics, that modulate (e.g., increase or decrease) activity mediated by Trk-receptors such as TrkA, TrkB and TrkC. Such compounds are generally referred to here as Trk-receptor modulator compounds or "Trk modulators."

Trk modulators of the invention are useful, e.g., for modulating processes such as neuronal growth and survival, axonal growth, neurite outgrowth, synaptic plasticity and other processes that are mediated, at least in part, by a Trk-receptor. These uses include therapeutic methods that may involve modulating the growth and repair of the central nervous system in vitro (e.g., in a cell culture) or in vivo (such as in a patient or other individual). Trk modulators of the invention therefore have utility in the treatment of diseases such as stroke, Alzheimer's disease, Parkinson's disease, head trauma, spinal cord injury, and epilepsy to name a few.

Applicants have discovered that a key interaction between Trk receptors and their neurotrophin ligands occurs through a conserved short linear sequence motif of three amino acid residues—Arg-Gly-Glu (i.e., "RGE" in the single letter amino acid code) found at the N-terminal of mature neurotrophin amino acid sequences. The RGE motif is present in all neurotrophins and, when bound to the Trk receptor, exists as half a helix in what is considered a tight loop.

Applicants have also discovered that properly constrained peptides (for example, cyclic peptides) of the small linear RGE motif have a high structural overlap with the native NT structure and are able to function as Trk receptor antagonists. Similarly, peptidomimetic compounds having high structural overlap with such constrained RGE peptides are also expected to have high structural overlap with the native NT structure and, as such, can also function as Trk receptor antagonists.

As noted above, the RGE motif is conserved among all neurotrophins, and interactions with this motif are important for the binding of those neurotrophins to their respective Trk receptor(s). Hence, constrained peptides and peptidomimetics comprising the RGE motif are useful as antagonists of a wide variety of Trk receptors, including TrkA, TrkB and TrkC. However, Trk modulators of the present invention can also be targeted to specific Trk receptors, by selecting flanking amino acid sequences from an NT ligand that preferably binds to the desired Trk receptor. In preferred Trk antagonist compounds (i.e., Trk modulator compounds that inhibit Trk receptor mediated activity), such flanking residues preferably range in length from no more than about 0 to 10 amino acid residues in length, with sizes between about 2–5 or 2–3 amino acid residues being particularly preferred. Moreover, the size of the cyclic peptide ring (or the corresponding peptidomimetic structure) preferably ranges from only about 4 to 15 amino acid residues, with sizes from about 5 to 10 amino acid residues being particularly preferred.

Applicants have also determined that, in crystal structures of NT dimers in complex with their binding domain of a Trk receptor, the RGE motif runs anti-parallel to itself in the NT dimer. That is to say, the RGE helix in the first NT molecule is aligned with and in an anti-parallel orientation to the RGE helix in the second NT molecule in that dimer. See, in particular, FIGS. 6A–6C. Applicants have moreover discovered that, when a tandem repeat peptide or peptidomimetic of the RGE motif is properly constrained (as in a cyclic peptide or peptidomimetic), it adopts the same anti-parallel alignment conformation and has a high structural overlap with the native NT structure. Such "tandem-repeat" RGE cyclic peptides and peptide mimetics are, surprisingly, able to function as Trk receptor agonists (i.e., they are able to increase activity mediated by a Trk receptor). As such, these compounds are also among the Trk modulator compounds of the invention.

As with the RGE antagonists, described, supra, constrained peptides and peptidomimetics comprising a tandem repeat of the RGE motif are useful as agonists for a wide variety of Trk receptors, including TrkA, TrkB and TrkC. However, the compounds can also be targeted to specific Trk receptors, for example, by selecting flanking amino acid sequences from a NT ligand that preferably binds to the desired Trk receptor. In preferred Trk agonists compounds (i.e., the Trk modulator compounds that increase Trk receptor mediated activity) such flanking residues preferably range in length from no more than about 0 to 10 amino acid residues in length, with sizes from 2–5 or 2–3 being more preferred.

Tandem repeat cyclic peptides and peptidomimetics of the invention may, optionally, contain additional amino acid residues situated between the two tandem repeats of the RGE motif. Such additional amino acid residues therefore function as "spacer" moieties to join the two RGE motifs together in such a way that they adopt the anti-parallel alignment conformation having a high structural overlap with the RGE motif in the native NT structure(s). The exact identity of the spacer amino acid residue(s) is not important and their identities may or may not correspond to identities of amino acid residues flanking the RGE motif in a particular neurotrophin. Preferably, the spacer moiety (if present) in a tandem repeat cyclic peptide or peptidomimetic is short; e.g., not longer than five amino acid residues in length, with spacer moieties between about 0–3 amino acid residues in length being more preferred. Particularly preferred spacer moieties are only about 1 or 2 amino acid residues in length.

The total size of such "tandem-repeat" cyclic peptides and peptidomimetics is moreover, typically about twice that of a Trk antagonist cyclic peptide or peptidomimetic of the invention. Hence, preferred sizes of the peptide ring (or corresponding peptidomimetic structure) are preferably from about 8 to 30 amino acid residues in length, with sizes from about 10 to 20 amino acid residues in length being particularly preferred.

Preferred cyclic peptides that comprise the RGE motif and/or tandem repeats thereof are described in Section 6.1, infra. Section 6.2 then describes routine experimental methods by which a person skilled in the art can determine, e.g., by X-ray crystallography or NMR spectroscopy, three-dimensional "pharmacophore" structures for these and other cyclic peptides, and methods using such pharmacophore structures to design appropriate peptidomimetic compounds are provided in Section 6.3, infra, along with exemplary peptidomimetic modifications. Still further modifications to the Trk modulator compounds of the invention are described in Section 6.4, including pharmaceutical formulations and medicinal uses. Section 6.5 describes routine assays by which a person skilled in the art may verify the Trk modulator activity of a compound, such as a peptidomimetic compound. Section 6.6 then describes certain preferred exemplary uses of such compounds in methods for modulating Trk mediated activities such as neuronal survival, axonal growth and synaptic plasticity. Formulations of Trk modulators (including pharmaceutical formulations) that are particularly suitable for such uses are provided in Section 6.7. The specification concludes with a series of examples, at Section 7, demonstrating certain exemplary embodiments of the invention.

The present invention also provides methods for the administration of a p75 receptor binding agent to an individual, wherein the p75 receptor binding agent interferes with the binding of a neurotrophin to a p75 receptor engaged in an inhibitory complex and, thus, promotes neurotrophin binding to a Trk receptor. These methods are useful in the treatment of conditions wherein CNS neurons are damaged or injured, for example, diseases such as stroke, Alzheimer's disease, Parkinson's disease, traumatic brain injury and spinal cord injury.

The present invention is based, in part, on the discovery that agents designed to interfere with neurotrophin binding to a p75 receptor engaged in an inhibitory complex facilitate neurotrophin-mediated CNS neurite outgrowth. As described in the Examples section below, neurite outgrowth assays were performed using cultured rat cerebellar neurons in an inhibitory environment. The inhibitory culture media was supplemented with NGF, NGF in combination with BDNF, a constrained monomer of the NGF first binding loop (N-Ac-CTDIKGKEC-$NH_2$) (SEQ ID NO:43), or the NGF loop 1 peptide in combination with BDNF. Cultures were maintained for 23 hours, fixed, and stained for GAP-43. The mean length of the longest neurite was then determined from 100–120 neurons under each culture condition. It was found that NGF alone and the constrained monomer alone did not promote neurite outgrowth, but the combinations of NGF with BDNF in ratios of 10:1 and 100:1 and the NGF loop 1 peptide at 100 μg/ml with BDNF at 1 ng/ml promoted neurite outgrowth. These findings show that administration of a p75 receptor binding agent, which is a neurotrophin that does not bind the expressed Trk receptor in combination with another, different neurotrophin, which binds a Trk receptor expressed on the injured neurons results in CNS neuron growth in an inhibitory environment. Here, the neurotrophin, which does not bind to an expressed Trk receptor (i.e., a p75 receptor binding agent) was administered in an amount about 10 to about 100 fold greater than the neurotrophin, which binds to an expressed Trk receptor (i.e., not a p75 receptor binding agent). These results also show that administration of a constrained monomer of the NGF first binding loop, a non-neurotrophin p75 receptor binding agent, promotes neurotrophin-mediated CNS neuron growth.

Definitions

The following defined terms are used throughout the present specification, and should be helpful in understanding the scope and practice of the present invention.

As used herein "an inhibitory environment" means an environment in which growth of a damaged or injured neuron is inhibited. An inhibitory environment is present in the milieu surrounding damaged or injured neurons. Damaged or injured neurons are present in conditions, which include, for example, diseases and disorders that are associated with damage to or impaired function of the CNS. Exemplary conditions include, but are not limited to, Alzheimer's disease, Parkinson's disease, Huntington's disease, amyotrophin lateral sclerosis, stroke, traumatic brain injury, and spinal cord injury. Alternatively, an inhibitory environment is an environment wherein a p75 receptor is engaged in an inhibitory complex (i.e., a p75 receptor is engaged with a molecule that binds a p75 receptor, e.g., a myelin-derived molecule such as MAG or Nogo-A), and this binding results in inhibition of neurotrophin-mediated neuron growth).

The term "therapeutically effective" means that quantity of a compound or pharmaceutical composition that is sufficient to result in a desired activity upon administration to an individual in need thereof. Preferably, a therapeutically effective amount can ameliorate or prevent a clinically significant deficit in the activity, function and response of the individual. Alternatively, a therapeutically effective amount is sufficient to cause an improvement in a clinically significant condition in the individual. For example, "therapeutically effective" means an amount or dose of a p75 receptor inhibitor sufficient to promote the growth of a neuron in the CNS in an inhibitory environment.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government of listed in the U.S. Pharmacopeia or other generally recognized pharmacopeia for use in animals, and more particularly in humans.

The term "carrier" refers to a diluent, adjuvant, excipient, or vehicle with which the compound is administered. Such pharmaceutical carriers can be sterile liquids, such as water and oils, including those of petroleum, animal, vegetable, or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

An "individual" or "patient" as used herein is preferably a mammal and more preferably a human, but can be any animal, including a laboratory animal in the context of a clinical trial or screening or activity experiment. Thus, as can be readily appreciated by one of ordinary skill in the art, the methods of the present invention are particularly suited to administration to any animal, particularly a mammal, and including, but not limited to domestic animals, wild animals and research animals.

6.1. TRK Receptor Modulators: Cyclic Peptides

The term "cyclic peptide," as used herein, refers to a peptide or salt thereof that comprises: (1) an intramolecular covalent bond between two non-adjacent residues; and (2) at least one Trk-receptor recognition sequence RGE (i.e., Arg-Gly-Glu) within a cyclic ring of the cyclic peptide. It is understood that preferred peptides of the invention which function as either Trk receptor agonists or antagonists will be constrained and, hence, are preferably cyclic peptides. However, non-cyclic or "linear" peptides are also useful (e.g., as intermediate compounds for making cyclic peptides of the invention). Hence, non-cyclic versions of the cyclic peptides described throughout this application are also considered part of the present invention.

The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Preferred intramolecular bonds include, but are not limited to, disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452. Such cyclic bonds and other modifications can also be applied to the cyclic peptides and derivative compounds of this invention. For convenience, cyclic peptides of the invention are frequently illustrated in this application showing particular cyclic bonds, which may or may not be preferred. However, other embodiments of these cyclic peptides comprising additional and/or alternative cyclic bonds will be apparent to those persons skilled in the art and are therefore considered part of this invention.

Within certain embodiments a cyclic peptide of the invention preferably comprises an N-acetyl group (i.e., an amino group present on the amino terminal residue of the peptide is acetylated, preferably prior to cyclization). Alternatively, a cyclic peptide of the invention may comprise an N-formyl group (i.e., the amino group present on the amino terminal residue of the peptide is formylated, preferably prior to cyclization). Alternatively, the amino group present on the amino terminal residue of the peptide may be mesylated; again, preferably prior to cyclization. The presence of such terminal groups may, for example, enhance cyclic peptide activity or stability in certain applications. In addition, within certain embodiments a cyclic peptide of the invention may comprise a C-amide group.

In certain embodiments, preferred cyclic peptides of the present invention satisfy the general formula:

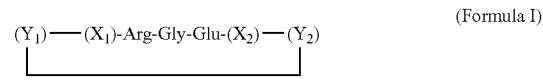

(Formula I)

where $Y_1$ and $Y_2$ are amino acid residues whose identities are independently selected and having a covalent bond between the residues $Y_1$ and $Y_2$. The elements $X_1$ and $X_2$ are optional and, if present, they are independently selected from the amino acid residues and combinations thereof that are linked by peptide bonds. Hence, either $X_1$ or $X_2$ or both $X_1$ and $X_2$, if present, may be a single amino acid residue or, alternatively, may each be a sequence comprising a plurality of amino acid residues linked by peptide bonds.

In preferred embodiments, a cyclic peptide satisfying Formula I, above, will modulate one or more Trk-receptor mediated activities. For example, in certain preferred embodiments a peptide satisfying Formula I will inhibit one or more Trk-receptor mediated activities and, as such, will be a Trk antagonist. In other embodiments, a peptide satisfying Formula I will increase one or more Trk receptor mediated activities and, as such, will be a Trk agonist.

In addition to the RGE consensus sequence(s), cyclic peptides of the invention generally comprise at least one additional residue within the cyclic ring so that preferably at least one of either $X_1$ or $X_2$ in Formula I is present. Generally, the size of $X_1$ and/or $X_2$ will depend upon the desired activity of the cyclic peptide. For example, where a cyclic peptide that is a Trk antagonist is desired, shorter peptide sequences are preferred. Accordingly, in such embodiments, $X_1$ and/or $X_2$ are each preferably between 0 and about 10 amino acids in length, with sizes of about 1, 2, 3, 4 or 5 amino acid residues being particularly preferred. Moreover, in such embodiments the lengths of $X_1$ and/or $X_2$ are also preferably selected so that the size of the cyclic peptide ring ranges from about 5 to about 15 amino acid residues, and is more preferably between about 5–10 amino acid residues in length. Peptide ring sizes of about 5–7 amino acid residues in length are particularly preferred. Such additional residues (i.e., $X_1$ and/or $X_2$ in Formula I, supra) may be present on either the N-terminal or C-terminal side of the RGE sequence, or they may be present on both sides of the RGE sequence.

In preferred cyclic peptides of the invention, the additional residues are derived from sequences that flank the RGE sequence within one or more naturally occurring neurotrophins (e.g., NGF, BDNF, NT-3, NT-4, NT-5 and NT-4/5) with or without amino acid substitutions and/or other modifications. In particular, the presence of flanking sequences from a neurotrophin may help target a cyclic peptide for a particular Trk receptor of interest. Hence, in embodiments where an antagonist for a particular Trk receptor is desired, a cyclic peptide of the invention may comprise amino acid residues flanking either the N-terminal, C-terminal or both sides of the RGE sequence that are derived from flanking sequences in a neurotrophin that preferably binds to the targeted Trk receptor.

As an example, and not by way of limitation, Table I, infra, list certain preferred cyclic peptides that comprise additional amino acid residues derived from particular neurotrophins whose identities are also indicated in the table. The right-hand column in Table I also indicates a Trk receptor to which the neurotrophin preferably binds (or, rather, binds with the highest binding affinity). Hence, each cyclic peptide listed in Table I may, in one embodiment, be used to inhibit the particular Trk receptor indicated along side it, in the right hand column of Table I. Those skilled in the art will appreciate, however, that there is some overlap in binding specificity of the different neurotrophin ligands for various Trk receptors. Hence, the cyclic peptides listed in Table I can also be used as antagonists of other Trk receptors. As a particular example, and not by way of limitation, it is demonstrated in the Examples, infra, that the cyclic peptide N-Ac-<u>CSRRGEC</u>-NH$_2$, (SEQ ID NO:2) which contains additional residues from the neurotrophin NT-4, is a more potent TrkB antagonist than are the peptides N-Ac-<u>CSHRGEC</u>-NH$_2$ (SEQ ID NO: 7 with an acetylated N-terminal amino group and C-terminal amide group) and N-Ac-<u>CFHRGEC</u>-NH$_2$ (SEQ ID NO:6) equivalent peptides designed with additional residues from the neurotrophins NT-3 and NGF, respectively.

TABLE I

TRK ANTAGONISTS

| Peptide Formula | NT | Trk-R |
|---|---|---|
| ($Y_1$)—Ser—Arg—Arg—Gly—Glu—($Y_2$) | NT-4 | TrkB |
| ($Y_1$)—Ala—Arg—Arg—Gly—Glu—($Y_2$) | BDNF | TrkB |
| ($Y_1$)—Phe—His—Arg—Gly—Glu—($Y_2$) | NGF | TrkA |
| ($Y_1$)—Ser—His—Arg—Gly—Glu—($Y_2$) | NT-3 | TrkC |

Examples of particularly preferred cyclic peptide sequences of the invention, which are preferably Trk antagonists, include:

| | |
|---|---|
| <u>CSRRGEC</u>, | (SEQ ID NO:1) |
| N-Ac-<u>CSRRGEC</u>-NH$_2$, | (SEQ ID NO:2) |
| <u>CARRGEC</u>, | (SEQ ID NO:3) |
| N-Ac-<u>CARRGEC</u>-NH$_2$, | (SEQ ID NO:4) |
| <u>CFHRGEC</u>, | (SEQ ID NO:5) |
| N-Ac-<u>CFHRGEC</u>-NH$_2$, | (SEQ ID NO:6) |
| <u>CSHRGEC</u>, | (SEQ ID NO:7) |
| N-Ac-<u>CFHRGE</u>-NH$_2$, | (SEQ ID NO:8) |
| <u>CRGEC</u>, and | (SEQ ID NO:9) |
| N-Ac-<u>CRGEC</u>-NH$_2$. | (SEQ ID NO:10) |

The underlined portion of each foregoing amino acid sequence indicates that portion of the peptide that is cyclized. "N-Ac" denotes an acetylated N-terminal amino group and "NH$_2$" denotes a C-terminal amide group.

Within certain embodiments, relatively small cyclic peptides of the invention that do not contain significant sequences flanking the RGE consensus sequence are particularly preferred. Such peptides may or may not contain an N-acetyle group and they may or may not contain a C-amide group. Examples of preferred, small cyclic peptides of the invention include:

| | |
|---|---|
| N-Ac-<u>CRGEC</u>-NH$_2$, | (SEQ ID NO:10) |
| N-Ac-<u>KRGED</u>-NH$_2$, | (SEQ ID NO:11) |
| H-C(O)-<u>CRGEC</u>-NH$_2$, | (SEQ ID NO:12) |
| CH$_3$-SO$_2$-NH-<u>CRGEC</u>-NH$_2$, | (SEQ ID NO:13) |
| N-Ac-<u>CRGEC</u>-Y-NH$_2$, | (SEQ ID NO:14) |
| H-C(O)-<u>CRGEC</u>-Y-NH$_2$, and | (SEQ ID NO:15) |
| CH$_3$-SO$_2$-NH-<u>CRGEC</u>-Y-NH$_2$. | (SEQ ID NO:16) |

In other embodiments of the invention, where a Trk agonist is desired, longer peptide sequences are generally preferred. In particular, preferred cyclic peptides of the invention that are Trk agonists comprise at least one "tandem repeat" of the RGE motif. Accordingly, where such cyclic peptides satisfy Formula I, supra, at least one of $X_1$ and $X_2$ will be present and comprises a second RGE sequence. More specifically, such cyclic peptides of the invention preferably satisfy the following general formula:

(Formula II)

($Y_1$)—($Z_1$)-Arg-Gly-Glu-($Z_0$)-Arg-Gly-Glu-($Z_2$)—($Y_2$)

As in Formula I, $Y_1$ and $Y_2$ are amino acid residues whose identities are independently selected and having a covalent bond between the residues $Y_1$ and $Y_2$. The elements $Z_1$ and $Z_2$ are optional and, if present, they are independently selected from the amino acid residues and combinations thereof that are linked by peptide bonds. The element $Z_0$ is also optional, and if present is an amino acid residue or some combination thereof, linked by peptide bonds. Hence, either $Z_1$, $Z_2$, $Z_0$ or any combination thereof, if present, may each be a single amino acid residue or, alternatively, they may each be a sequence comprising a plurality of amino acid residues linked by peptide bonds.

In addition to a tandem repeat of the RGE consensus sequence, cyclic peptides of the invention generally comprise one additional residues within the cyclic ring so that, preferably, at least one of either $Z_1$, $Z_2$ and/or $Z_0$ is present. In embodiments where a cyclic peptide that is a Trk agonist is desired, $Z_1$, $Z_2$ and/or $Z_0$ are each preferably no more than about ten amino acid residues in length, and more preferably are each only 1, 2, 3, 4 or 5 amino acid residues in length. Moreover, the lengths of $Z_1$, $Z_2$ and/or $Z_0$ are preferably selected so that the size of the cyclic peptide ring ranges from about 8–50 amino acid residues, and more preferably from about 8–25 or from about 15–20 amino acid residues.

As with the cyclic peptides of Formula I, in preferred cyclic peptides of Formula II the additional residues (i.e., $Z_1$, $Z_2$ and/or $Z_0$) can be derived from sequences that flank the RGE sequence within one or more naturally occurring neurotrophin (e.g., NGF, BDNF, NT-3, NT-4, NT-5 or NT-4/5), with or without amino acid substitutions and/or other modifications. In particular, the presence of flanking amino acid residues from a particular neurotrophin may help target a cyclic peptide for a particular Trk receptor of interest. Hence, in embodiments where an antagonist for a particular Trk receptor is desired, a cyclic peptide of the invention may comprise amino acid residues flanking the N-terminal and/or C-terminal of one or both tandem repeat RGE sequences, and these flanking sequences may be derived from a neurotrophin that preferably binds to the targeted Trk receptor of interest.

As noted above, preferred tandem repeat cyclic peptides of the invention (including cyclic peptides according to Formula II) have the two RGE sequences aligned antiparallel to each other. Accordingly, in preferred cyclic peptides according to Formula II the element $Z_0$ is present and can function as an effective "spacer moiety" to align the two RGE sequences together in an anti-parallel alignment conformation. In preferred embodiments, $Z_0$ is not more than 10 amino acid residues in length, and is preferably five or fewer amino acid residues in length. Preferred sizes for $Z_0$ are about 1, 2, 3, 4 or 5 amino acid residues in length. The exact sequence of amino acid residues in $Z_0$ is not critical. As such, the element $Z_0$ may or may not comprise a sequence of amino acid residues corresponding to a sequence from either the N-terminal or C-terminal of the RGE motif in a natural neurotrophin (e.g., NGF, BDNF, NT-3, NT-4, NT-5 and NT-4/5). Where $Z_0$ does comprise sequences from a neurotrophin, those sequences may or may not comprise amino acid substitutions and/or modifications.

Examples of particularly preferred cyclic peptide sequences of the invention, which are preferably Trk agonists, include:

| | |
|---|---|
| CSRRGELAASRRGELC | (SEQ ID NO:17) |
| N-Ac-CSRRGELAASRRGELC-NH$_2$ | (SEQ ID NO:18) |
| CFHRGEFSIFHRGEFC | (SEQ ID NO:30) |
| CARRGELSARRGELC | (SEQ ID NO 31) |
| CSHRGEYSKSHRGEYC | (SEQ ID NO:32) |

The cyclic peptide sequences identified by SEQ ID NOs: 30, 31, and 32 are TrkA, TrkB, and TrkC agonists, respectively. SEQ ID NO:30 is derived from NGF. SEQ ID NO: 31 is derived from BDNF. SEQ ID NO: 32 is derived from NT-3.

Cyclic peptides as described herein may comprise residues of L-amino acids, D-amino acids, or any combination thereof. The amino acids may from natural or non-natural sources provided that at least one amino group and at least one carboxyl group are present in the molecule. A- and β-amino acids are generally preferred. The 20 L-amino acids commonly found in proteins are particularly preferred in the present invention. These amino acids are identified herein by their conventional three-letter and one-letter abbreviations, whereas the corresponding D-amino acids are designated by the prefix "d".

In certain embodiments, cyclic peptides of the invention may comprise a sequence of D-amino acid residues that is the opposite of a sequence of L-amino acid residues provided herein. For example, the invention provides certain Trk receptor agonist polypeptides, referred to herein as riB$_{AG1}$ and hriB$_{AG2}$ (SEQ ID NOS:40–41) that comprise sequences of D-amino acid sequences which are the reverse sequence of another Trk receptor agonist polypeptide refereed to as the B$_{AG}$ polypeptide (SEQ ID NO:17). Hence, in addition to the polypeptides of L-amino acid residues described supra, the present invention also contemplates polypeptides having the reverse sequence of L-amino acid residues. Hence, in one preferred embodiment peptides and peptidomimetics of the present invention comprise sequences of L-amino acid residues including the Arg-Gly-Glu (i.e., "RGE") motif described, supra. Accordingly, the invention also provides, in an alternative embodiment) peptides and peptidomimetics comprising sequences of D-amino acid residues including the short linear sequence motif dGlu-Gly-dArg (i.e., "dEGdR"). Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Cyclic peptides as described herein may be synthesized by methods well known in the art, including recombinant DNA methods and chemical synthesis. Chemical synthesis may generally be performed using standard solution phase or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross & Meienhofer, eds., "The Peptides: Analysis, Synthesis, Biology," Vol. 1–4 (Academic Press, 1979); Bodansky & Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. In particular, a high percentage of racemization may be observed when residues such as Phe-Gly are coupled. Such situations are, however, uncommon. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 1963, 85:2149. These methods involve assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs.

Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation.

Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline.

It will be readily apparent to those of ordinary skill in the art that, within each of these representative formulas set forth supra, any of the above thiol-containing residues may be employed in place of one or both of the thiol-containing residues recited.

Within further embodiments, cyclization may be achieved by amide bond formation. For example, a peptide bond may be formed between terminal functional groups (i.e., the amino and carboxy termini of a linear peptide prior to cyclization). Examples of such peptides include c(SRRGE) (SEQ ID NO:33), c(ARRGE) (SEQ ID NO:34), c(FHRGE) (SEQ ID NO:35) and c(SHRGE) (SEQ ID NO:36). An example of one particularly preferred peptide having such a cyclic amide bond is the peptide c(SRRGELSRRGEL) (SEQ ID NO:39). This peptide, which is described in the Examples, infra, is referred to here as the $hB_{AG2}$ peptide. Within another such embodiment, the linear peptide comprises a D-amino acid. For example, the Examples, infra, describe another preferred peptide that is referred to as the $hriB_{AG2}$ peptide. This peptide, which contains a cyclic amide bond as described, supra, comprises the following sequence of D amino acid residues:

c[dLdEdGdRdRdSdLdEdGdRdRdS] (SEQ ID NO:40). Alternatively, cyclization may be accomplished by linking one terminus and a residue side chain or using two side chains, as in KRGED (SEQ ID NO:37) or KSRRGED (SEQ ID NO:38), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from an O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino)phosphonium hexafluorophosphonate. (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages include:

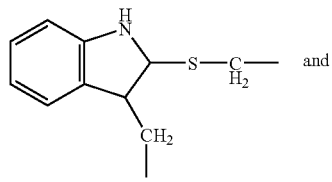 and

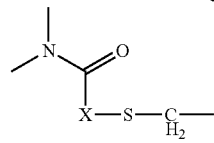

where X may be $(CH_2)_4$, $CH_2$ or

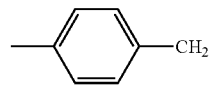

Cyclization may also be achieved using $\delta_1\delta_1$-Ditryptophan (i.e., Ac-Trp-Gly-Gly-Trp-OMe), as shown below:

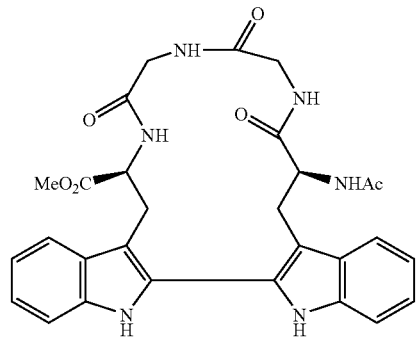

The structures and formulas recited herein are provided solely for the purpose of illustration, and are not intended to limit the scope of the cyclic peptides described herein.

6.2. Trk-Receptor Pharmacophores

For designing peptidomimetics, it is beneficial to obtain a three dimensional structure for the pharmacophore of one or more cyclic peptides described above. The term "pharmacophore" refers to the collection of functional groups on a compound that are arranged in three-dimensional space in a manner complementary to the target protein, and that are responsible for biological activity as a result of compound binding to the target protein. Useful three-dimensional pharmacophore models are best derived from either crystallographic or nuclear magnetic resonance structures of the target, but can also be derived from homology models based on the structures of related targets or three-dimensional quantitative structure-activity relationships derived from a previously discovered series of active compounds.

The present invention provides pharmacophores of certain representative cyclic peptides (i.e., three-dimensional conformations of the neurotrophin consensus sequence RGE within such peptides). Such three-dimensional structures provide the information required to most efficiently direct the design and optimization of peptidomimetics.

In one embodiment, the three-dimensional structures of cyclic peptides are generally determined using X-ray crystallography. These techniques are well known and are within the routine skill in the art. For example, see Cantor&Schimmel, *Biophysical Chemistry* 1980 (Vols. I–III) W.H. Freeman and Company (particularly Chapters 1–13 in Vol. I, and Chapter 13 in Vol. II). See, also, *Macromolecular Crystallography, Parts A–B*

(Carter&Sweet, Eds.) In: *Methods Enzymol.* 1997, Vols. 276–277; Jan Drenth, *Principles of Protein X-Ray Crystallography* (New York: Springer-Verlag, 1994).

The term "crystal" refers, generally, to any ordered (or at least partially ordered) three-dimensional array of molecules. Preferably, the ordering of molecules within a crystal is at least sufficient to produce a sharp X-ray diffraction pattern so that the molecules' three-dimensional structure may be determined.

The molecules in a crystal may be of any type, and it will be understood that a crystal may contain molecules of only one type or may comprise a plurality of different types of molecules. In preferred embodiments, crystals of the present invention comprise at least one biomolecule, such as a cyclic peptide described, supra, in Section 6.1. Crystals of the invention may even comprise a complex or assembly of two or more proteins or other biomolecules. For example, a crystal may comprise molecules of a ligand, such as a neurotrophin, bound to molecules of a receptor, such as a Trk receptor. Typically, crystals that contain biological molecules such as proteins will contain other molecules as well, such molecules of solvent (e.g., water molecules) and/or salt. Other molecules such as drugs, drug candidates or compounds that bind to the protein may also be present in a crystal.

Indeed, crystal structures for the binding domain of Trk receptors complexed with a neurotrophin are already available in the art. See, for example, Wiesmann et al., *Nature* 1999, 401:184; and Banfield et al., *Sturcutre (Camb.)* 2001, 9:1191. The coordinates of these X-ray structures can be readily obtained, for example, from the Protein Data Bank at <www.rcsb.orb> (Accession Nos. 1www and 1hcf, respectively). Hence, in particularly preferred embodiments, which are demonstrated in the Examples, infra, pharmacophore structures of the invention are determined using the X-ray crystal structure(s) of a neurotrophin bound to an appropriate Trk receptor (or fragment thereof). These three-dimensional structures can then be used to design peptidomimetics of the invention or, alternatively, to design additional cyclic peptides that are likely to be Trk modulators.

Alternatively, the three-dimensional structures of cyclic peptides may generally be determined using nuclear magnetic resonance (NMR) techniques that are well known in the art. NMR data acquisition is preferably carried out in aqueous systems that closely mimic physiological conditions to ensure that a relevant structure is obtained. Briefly, NMR techniques use the magnetic properties of certain atomic nuclei (such as $^1H$, $^{13}C$, $^{15}N$ and $^{31}P$), which have a magnetic moment or spin, to probe the chemical environment of such nuclei. The NMR data can be used to determine distances between atoms in the molecule, which can be used to derive a three-dimensional model or the molecule.

For determining three-dimensional structures of cyclic peptides (and candidate peptidomimetics, as discussed below) proton NMR is preferably used. More specifically, when a molecule is placed in a strong magnetic field, the two spin states of the hydrogen atoms are no longer degenerate. The spin aligned parallel to the field will have a lower energy and the spin aligned antiparallel to the field will have a higher energy. At equilibrium, the spin of the hydrogen atoms will be populated according to the Boltzmann distribution equation. This equilibrium of spin populations can be perturbed to an excited state by applying radio frequency (RF) pulses. When the nuclei revert to the equilibrium state, they emit RF radiation that can be measured. The exact frequency of the emitted radiation from each nucleus depends on the molecular environment of the nucleus and is different for each atom (except for those atoms that have the same molecular environment). These different frequencies are obtained relative to a reference signal and are called chemical shifts. The nature, duration and combination of applied RF pulses can be varied greatly and different molecular properties can be probed by those of ordinary skill in the art, by selecting an appropriate combination of pulses.

For three-dimensional structure determinations, one-dimensional NMR spectra are generally insufficient, as limited information pertaining to conformation may be obtained. One-dimensional NMR is generally used to verify connectivity within a molecule and yields incomplete data concerning the orientation of side chains within a peptide. Two-dimensional NMR spectra are much more useful in this respect and allow for unambiguous determination of side-chain-to-side-chain interactions and the conformation of the peptide backbone.

Two-dimensional NMR spectra are generally presented as a contour plot in which the diagonal corresponds to a one-dimensional NMR spectrum and the cross peaks off the diagonal result from interactions between hydrogen atoms that are directly scalar coupled. Two-dimensional experiments generally contain a preparation period, an evolution period where spins are "labeled" as they process in the XY plane according to their chemical shift, a mixing period, during which correlations are made with other spins and a detection period in which a free induction decay is recorded.

Two-dimensional NMR methods are distinguished by the nature of the correlation that is probed during the mixing period. A DQF-COSY (double quantum filtered correlation spectroscopy) analysis gives peaks between hydrogen atoms that are covalently connected through one or two other atoms. Nuclear Overhauser effect spectroscopy (NOESY) gives peaks between pairs of hydrogen atoms that are close together in space, even if connected by way of a large number of intervening atoms. In total correlation spectroscopy (TOCSY), correlations are observed between all protons that share coupling partners, whether or not they are directly coupled to each other. Rotating-frame Overhauser Spectroscopy (ROESY) experiments may be thought of as the rotating frame analogue of NOESY, and yields peaks between pairs of hydrogen atoms that are close together in space. One or more such methods may be used, in conjunction with the necessary water-suppression techniques such as WATERGATE and water flip-back, to determine the three-dimensional structure of a cyclic peptide or candidate peptidomimetic under aqueous conditions. Such techniques are well known and are necessary to suppress the resonance of the solvent (HDO) during acquisition of NMR data.

By way of example, both TOCSY and NOESY may be applied to representative cyclic peptides for the purpose of determining the conformation and the assignment. The water solvent resonance may be suppressed by application of the WATERGATE procedure. A water flipback pulse may also be applied at the end of the mixing period for both TOCSY and NOESY experiments to maintain the water signal at equilibrium and to minimize the loss of amide proton resonances due to their rapid exchange at the near neutral Ph conditions (i.e., Ph 6.8) used in the experiment. NMR data may be processed using spectrometer software using a squared cosine window function along both directions. Baseline corrections may be applied to the NOESY, ROESY and TOCSY spectra using the standard Bruker polynomial method.

NOESY data may be acquired at several mixing times ranging from 80 ms to 250 ms. The shorter mixing time NOESY may be acquired to ensure that no diffusion effects were present in the NOESY spectrum acquired at the longer mixing times. The interproton distances may generally be determined from the 250 ms NOESY. The sequence-specific assignment of the proton resonances may be determined by standard methods (see Wuthrich, *NMR of Proteins and Nucleic Acids*, Wiley & Sons, New York, 1986), making use of both the results of the TOCSY and NOESY data.

For conformational calculations, the NOE cross peaks may be initially converted to a uniform distance upper and lower bounds of 1.8–5.0 angstroms regardless of the NOE intensities. The NOE distances may be refined iteratively through a comparison of computed and experimental NOEs at the various mixing times. This refinement may be much in the spirit of the PEPFLEX-II procedure (Wang et al., Techniques in Protein Chemistry IV, 1993, Evaluation of NMR Based Structure Determination for Flexible Peptides: Application to Desmopressin p. 569), although preferably initial NOE-based distances with very loose upper bounds (e.g., 5 angstroms) are used to permit the generation of a more complete set of conformations in agreement with experimental data. Dihedral-angle constraints may be derived from the values of the $^3J$C$\alpha$H coupling constants. A tolerance value of 40 degrees may be added to each of the dihedral angle constraints to account for the conformational flexibility of the peptide. Distance geometry calculations may be carried out utilizing fixed bond lengths and bond angles provided in the ECEPP/2 database (Ni et al., *Biochemistry* 1992, 31:11551–11557). The $\omega$-angles are generally fixed at 180 degrees, but all other dihedral angles may be varied during structure optimization.

Structures with the lowest constraint violations may be subjected to energy minimization using a distance-restrained Monte Carlo method (Ripoll & Ni, *Biopolymers* 1992, 32:359–365; Ni, *J. Magn. Reson. B* 1995, 106:147–155), and modified to include the ECEPP/3 force field (Ni et al., *J. Mol. Biol.* 1995, 252:656–671). All ionizable groups may be treated as charged during constrained Monte Carlo minimization of the ECEPP/3 energy. Electrostatic interactions among all charges may be screened by use of a distance-dependent dielectric to account for the absence of solvent effects in conformational energy calculations. In addition, hydrogen-bonding interactions can be reduced to 25% of the full scale, while van der Waals and electrostatic terms are kept to full strengths. These special treatments help to ensure that the conformational search is guided primarily by the experimental NMR constraints and that the computed conformations are less biased by the empirical conformational energy parameters (Warder et al., *FEBS Lett.* 1997, 411: 19–26).

Low-energy conformations of the peptide from Monte Carlo calculations may be used in NOE simulations to identify proximate protons with no observable NOEs and sets of distance upper bounds that warrant recalibration. The refined set of NOE distances including distance lower bounds derived from absent NOEs are used in the next cycles of Monte Carlo calculations, until the resulting conformations produced simulate NOE spectra close to those observed experimentally (Ning et al., *Biopolymers* 1994, 34:1125–1137; Ni et al., *J. Mol. Biol.* 1995, 252:656–671). Theoretical NOE spectra may be calculated using a tumbling correlation time of 1.5 ns based on the molecular weight of the peptide and the experimental temperature (Cantor & Schimmel (1980) *Biophysical Chemistry*, W.H. Freeman & Co., San Francisco). All candidate peptide conformations are included with equal weights in an ensemble-averaged relaxation matrix analysis of interconverting conformations (Ni & Zhu, *J. Magn. Reson. B* 1994, 102:180–184). NOE simulations may also incorporate parameters to account for the local motions of the methyl groups and the effects of incomplete relaxation decay of the proton demagnitizations (Ning et al., *Biopolymers* 1994, 34:1125–1137). The computed NOE intensities are converted to the two-dimensional FID's (Ni, *Magn. Reson. B* 1995, 106:147–155) using the chemical shift of assignments, estimated linewidths and coupling constants for all resolved proton resonances. Calculated FIDs may be converted to simulated NOESY spectra using identical processing procedures as used for the experimental NOE data sets.

6.3. TRK Receptor Modulators: Peptidomimetics

As noted above, peptidomimetics are compounds in which at least a portion of the RGE sequence within a cyclic peptide is modified, such that the three dimensional structure of the peptidomimetic remains substantially the same as that of the RGE sequence.

Peptidomimetics may be peptide analogues that are, themselves, cyclic peptides containing one or more substitutions or other modifications within the RGE sequence. Alternatively, at least a portion of the RGE sequence may be replaced with a nonpeptide structure, such that the three-dimensional structure of the cyclic peptide is substantially retained. In other words, one, two or three amino acid residues within the RGE sequence may be replaced by a non-peptide structure. In addition, other peptide portions of the cyclic peptide may, but need not, be replaced with a non-peptide structure. Peptidomimetics (both peptide and non-peptidyl analogues) may have improved properties (e.g., decreased proteolysis, increased retention or increased bioavailability). Peptidomimetics generally have improved oral availability, which makes them especially suited to treatment of conditions such as cancer. It should be noted that peptidomimetics may or may not have similar two-dimensional chemical structures, but share common three-dimensional structural features and geometry. Each peptidomimetic may further have one or more unique additional binding elements. The present invention provides methods for identifying peptidomimetics. A variety of modifications of peptide modifications (including modifications to cyclic peptides as described supra) are known in the art and can be used to generate peptidomimetic compounds. See, for instance, International Patent Publication No. WO 01/53331. Such modifications can also be used in the present invention to generate peptidomimetic compounds, as well as the specific modifications described below.

All peptidomimetics provided herein have a three-dimensional structure that is substantially similar to a three-dimensional structure of a cyclic peptide as described above. In general, two three-dimensional structures are said to be substantially structurally similar to each other if their pharmacophore atomic coordinates have a root-mean square deviation (RMSD) less than or equal to 1 angstrom, as calculated using the Molecular Similarity module within the QUANTA program (QUANTA, available from Molecular Simulations Inc., San Diego, Calif.). All peptidomimetics provided herein have at least one low-energy three-dimensional structure that is substantially similar to at least one low-energy three-dimensional structure of a cyclic peptide as described above.

Low energy conformations may be identified by conformational energy calculations using, for example, the CHARMM program (Brooks et al., *J. Comput. Chem.* 1983, 4:187–217). The energy terms include bonded and non-bonded terms, including bond length energy, angle energy, dihedral angle energy, Van der Waals energy and electrostatic energy. It will be apparent that the conformational energy can be also calculated using any of a variety of other commercially available quantum mechanic or molecular mechanic programs. A low energy structure has a conformational energy that is within 50 kcal/mol of the global minimum.

The low energy conformation(s) of candidate peptidomimetics are compared to the low energy conformations of the cyclic peptide (as determined, for example, by NMR or X-ray crystallography) to determine how closely the conformation of the candidate mimics that of the cyclic peptide. In such comparisons, particular attention should be given to the locations and orientations of the elements corresponding to the crucial side chains. If at least one of the candidate low energy conformations is substantially similar to a solution conformation of a cyclic peptide (i.e., differs with a root-mean square deviation (RMSD) of 1 angstrom or less), the candidate compound is considered a peptidomimetic. Within such analyses, low energy conformations of candidate peptidomimetics in solution may be studied using, for example, the CHARMM molecular mechanics and molecular dynamics program (Brooks et al., *J. Comput. Chem.* 1983, 4:187–217), with the TIP3P water model (Jorgensen et al., *J. Chem Phys.* 1983, 79:926–935) used to represent water molecules. The CHARM22 force field may be used to represent the designed peptidomimetics.

By way of example, low energy conformations may be identified using a combination of two procedures. The first procedure involves a simulated annealing molecular dynamics simulation approach. In this procedure, the system (which includes the designed peptidomimetics and water molecules) is heated up to above room temperature, preferably around 600 K, and simulated for a period of 100 picoseconds (ps) or longer; then gradually reduced to 500 K and simulated for a period of 100 ps or longer; then gradually reduced to 400 K and simulated for a period of 100 ps or longer; gradually reduced to 300 K and simulated for a period of 500 ps or longer. The trajectories are recorded for analysis. This simulated annealing procedure is known for its ability for efficient conformational search.

The second procedure involves the use of the self-guided molecular dynamics (SGMD) method (Wu & Wang, *J. Physical Chemistry* 1998, 102:7238–7250). The SGMD method has been demonstrated to have an extremely enhanced conformational searching capability. Using the SGMD method, simulation may be performed at 300 K for 1000 ps or longer and the trajectories recorded for analysis.

Conformational analysis may be carried out using the QUANTA molecular modeling package. First, cluster analysis may be performed using the trajectories generated from molecular dynamic simulations. From each cluster, the lowest energy conformation may be selected as the representative conformation for this cluster and may be compared to other conformational clusters. Upon cluster analysis, major conformational clusters may be identified and compared to the solution conformations of the cyclic peptide(s). The conformational comparison may be carried out using the Molecular Similarity module within the QUANTA program.

Similarity in structure may also be evaluated by visual comparison of the three-dimensional structures displayed in a graphical format, or by any of a variety of computational comparisons. For example, an atom equivalency may be defined in the peptidomimetic and cyclic peptide three-dimensional structures, and a fitting operation used to establish the level of similarity. As used herein, an "atom equivalency" is a set of conserved atoms in the two structures. A "fitting operation" may be any process by which a candidate compound structure is translated and rotated to obtain an optimum fit with the cyclic peptide structure. A fitting operation may be a rigid fitting operation (e.g., the cyclic peptide three-dimensional structure can be kept rigid and the three-dimensional structure of the peptidomimetic can be translated and rotated to obtain an optimum fit with the cyclic peptide). Alternatively, the fitting operation may use a least squares fitting algorithm that computes the optimum translation and rotation to be applied to the moving compound structure, such that the root mean square difference of the fit over the specified pairs of equivalent atoms is a minimum. Preferably, atom equivalencies may be established by the user and the fitting operation is performed using any of a variety of available software applications (e.g., QUANTA, available from Molecular Simulations Inc., San Diego, Calif.). Three-dimensional structures of candidate compounds for use in establishing substantial similarity may be determined experimentally (e.g., using NMR techniques as described herein or x-ray crystallography), or may be computer-generated using, for example, methods provided herein.

Figure 3A:
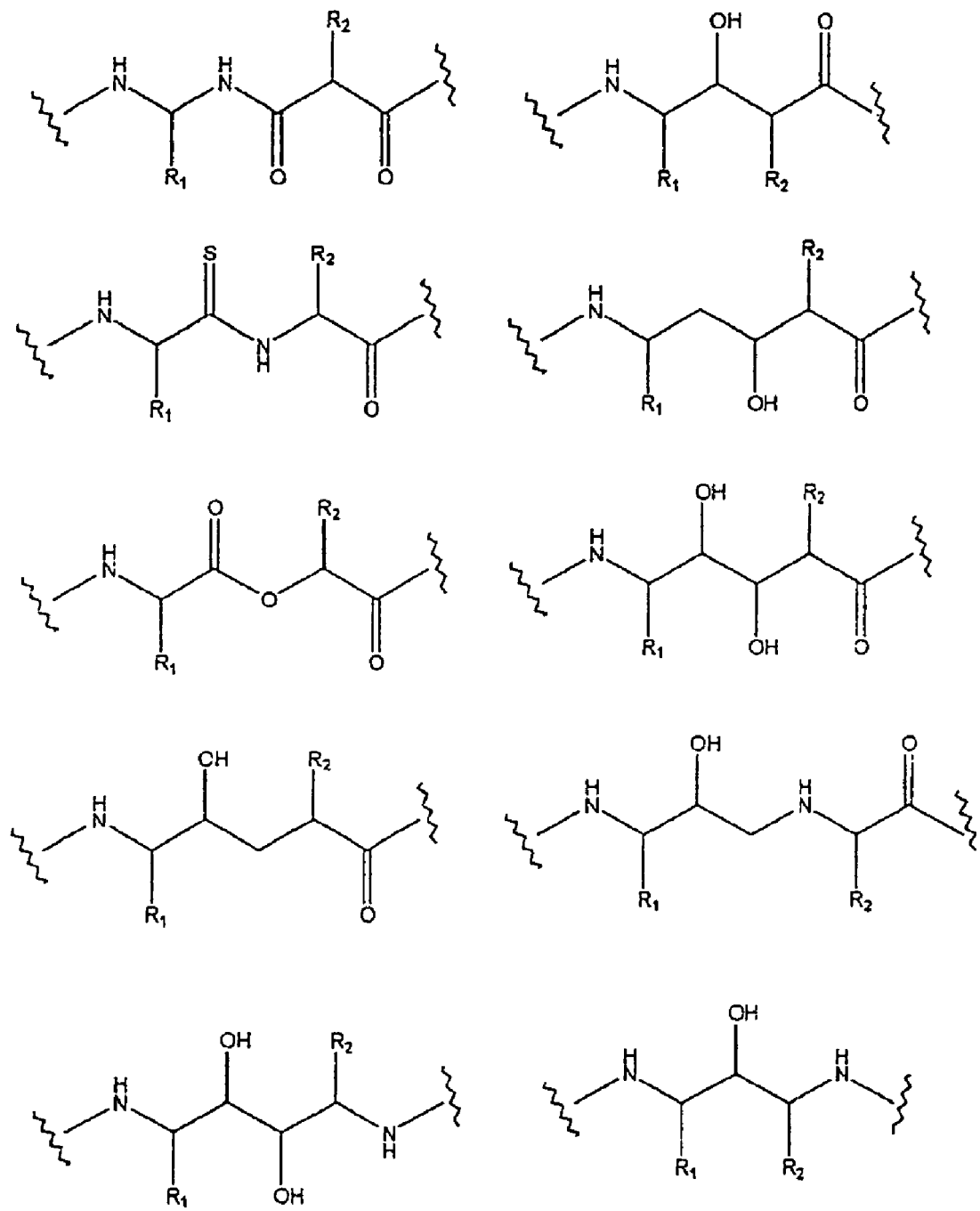

Certain peptidomimetics may be designed, based on the cyclic peptide structure. For example, such peptidomimetics may mimic the local topography about the cleavable amide bonds (amide bond isosteres). Examples of backbone modifications are given in FIGS. 3A and 3B (see also, FIGS. 4A–4B in WO 01/53331). These mimetics often match the peptide backbone atom-for-atom, while retaining functionality that makes important contacts with the binding sites. Amide bond mimetics may also include the incorporation of unusual amino acids or dipeptide surrogates. Examples of such unusual amino acids and dipeptide surrogates are illustrated here, in FIG. 4 (see also FIG. 5 in WO 01/53331). Still other examples are well known in the art (see, for example, in Gillespie et al., *Biopolymers* 1997, 43:191–217). The conformationally rigid substructural elements found in these types of mimetics are believed to result in binding with highly favorable entropic driving forces, as compared to the more conformationally flexible peptide linkages. Backbone modifications can also impart metabolic stability towards peptidase cleavage relative to the parent peptide. Other peptidomimetics may be secondary structure mimics. Such peptidomimetics generally employ non-peptide structures to replace specific secondary structures, such as $\beta$-turns, $\beta$-sheets and $\alpha$-turns (see FIG. 5).

To design a peptidomimetic, heuristic rules that have been developed through experience may be used to systematically modify a cyclic peptide. Within such modification, empirical data of various kinds are generally collected throughout an iterative refinement process. As noted above, optimal efficiency in peptidomimetic design requires a three-dimensional structure of the pharmacophore.

Pharmacophores as provided herein permit structure-based peptidomimetic design through, for example, peptide scaffold modification as described above. Certain peptidomimetics may be identified through visual inspection of one or more pharmacophores, as compared to the neurotrophin RGE conformation. Peptidomimetics can also be designed based on a visual comparison of a cyclic peptide pharmacophore with a three-dimensional structure of a candidate compound, using knowledge of the structure-activity relationships of the cyclic peptide. Structure-activity studies have established important binding elements in the cyclic peptides, and have permitted the development of pharmacophore models. Peptidomimetics designed in this manner should retain these binding elements.

Peptidomimetics may also be designed around replacing the disulfide bond (—S—S—) with a thioether (—S—

$CH_2$—C(O)—). The disulfide bond in general is not very stable as it can readily be reduced under acidic conditions. Replacing the disulfide bond with a thioether moiety (—S—$CH_2$—C(O)—) can significantly improve the stability of the peptide and therefore the oral availability.

As an alternative to design by visual inspection, libraries (e.g., containing hydantoin and/or oxopiperazine compounds) may be made using combinatorial chemical techniques. Combinatorial chemical technology enables the parallel synthesis of organic compounds through the systematic addition of defined chemical components using highly reliable chemical reactions and robotic instrumentation. Large libraries of compounds result from the combination of all possible reactions that can be done at one site with all the possible reactions that can be done at a second, third or greater number of sites. Combinatorial chemical methods can potentially generate tens to hundreds of millions of new chemical compounds as mixtures, attached to a solid support, or as individual compounds.

Pharmacophores can be used to facilitate the screening of such chemical libraries. For example, instead of producing all possible members of every library (resulting in an unwieldy number of compounds), library synthesis can focus on the library members with the greatest probability of interacting with the target. The integrated application of structure-based design and combinatorial chemical technologies can produce synergistic improvements in the efficiency of drug discovery.

Further peptidomimetics are compounds that appear to be unrelated to the original peptide, but contain functional groups positioned on a nonpeptide scaffold that serve as topographical mimics. This type of peptidomimetic is referred to herein as a "non-peptidyl analogue." Such peptidomimetics may be identified using library screens of large chemical databases. Such screens use the three-dimensional conformation of a pharmacophore to search such databases in three-dimensional space. A single three-dimensional structure may be used as a pharmacophore model in such a search. Alternatively, a pharmacophore model may be generated by considering the crucial chemical structural features present within multiple three-dimensional structures.

Any of a variety of databases of three-dimensional structures may be used for such searches. A database of three-dimensional structures may be prepared by generating three-dimensional structures of a database of compounds, and storing the three-dimensional structures in the form of data storage material encoded with machine-readable data. The three-dimensional structures can be displayed on a machine capable of displaying a graphical three-dimensional representation and programmed with instructions for using the data. Within preferred embodiments, three-dimensional structures are supplied as a set of coordinates that define the three-dimensional structure.

Preferably, the 3D-database contains at least 100,000 compounds, with small, non-peptidyl molecules having relatively simple chemical structures particularly preferred. It is also important that the 3D co-ordinates of the compounds in the database be accurately and correctly represented. The National Cancer Institute (NCI) 3D-database (Milne et al., *J. Chem. Inf. Comput. Sci.* 1994, 34:1219–1224) and the Available Chemicals Directory (ACD; available from MDL Information Systems, San Leandro, Calif.) are two excellent databases that can be used to generate a database of three-dimensional structures, using molecular modeling, as discussed above. For flexible molecules, which can have several low-energy conformations, it is desirable to store and search multiple conformations. The Chem-X program (Oxford Molecular Group PLC; Oxford UK) is capable of searching thousands or even millions of conformations for a flexible compound. This capability of Chem-X provides a real advantage in dealing with compounds that can adopt multiple conformations. Using this approach, although the NCI-3D database presently contains a total of 465,000 compounds, hundreds of millions of conformations can be searched in a 3D-pharmacophore searching process.

A pharmacophore search typically involves three steps. The first step is the generation of a pharmacophore query. Such queries may be developed from an evaluation of critical distances in the three dimensional structure of a cyclic peptide. Using the pharmacophore query of interest, a distance bit screening is performed on the database to identify compounds that fulfill the required geometrical constraints. In other words, compounds that satisfy the specified critical pair-wise distances are identified. After a compound passed the distance bit screening step, the program next checks whether the compound meets the sub-structural requirements as specified in the pharmacophore query. After a compound passes this sub-structural check, it is finally subjected to a conformational analysis. In this step, conformations are generated and evaluated with regard to geometric requirements specified in the phamacophore query. Compounds that have at least one conformation satisfying the geometric requirements, are considered as 'hits' and are recorded in a result database.

Other criteria, which will be apparent to those of ordinary skill in the art, may also be considered when selecting specific compounds for particular applications, such as the simplicity of the chemical structure, low molecular weight, chemical structure diversity and water solubility. The application of such criteria is well understood by medicinal, computational and structural chemists.

It will be apparent that a compound structure may be optimized using screens as provided herein. Within such screens, the effect of specific alterations of a candidate compound on three-dimensional structure may be evaluated, in order to optimize three-dimensional similarity to a cyclic peptide. Such alterations include, for example, changes in hydrophobicity, steric bulk, electrostatic properties, size and bond angle.

Biological testing of candidate compounds may be used to confirm peptidomimetic activity. In general, peptidomimetics should function in a substantially similar manner as a structurally similar cyclic peptide. In other words, a peptidomimetic of the cyclic peptide N-Ac-CSRRGEC-$NH_2$ (SEQ ID NO:2) should bind to a TRK with an affinity that is at least half the affinity of the cyclic peptide N-Ac-CSRRGEC-$NH_2$ (SEQ ID NO:2), as measured using standard binding assays. Further, a peptidomimetic of the cyclic peptide N-Ac-CSRRGEC-$NH_2$ (SEQ ID NO:2) should modulate a TRK-mediated function using a representative assay provided herein at a level that is at least half the level of modulation achieved using N-Ac-CSRRGEC-$NH_2$ (SEQ ID NO:2).

Once an active peptidomimetic has been identified, related analogues may be identified using two-dimensional similarity searching. Such searching may be performed, for example, using the program ISIS Base (Molecular Design Limited). Two-dimensional similarity searching permits the identification of other available, closely related compounds, which may be readily screened to optimize biological activity.

6.4. TRK Modulating Agents

As noted above, the term "Trk modulator" is used here, to describe any molecule comprising at least one cyclic peptide or peptidomimetic compound of the invention containing the neurotrophin motif RGE (i.e., Arg-Gly-Glu). Multiple cyclic peptides and/or peptidomimetics can be present in a modulating agent of the invention. Moreover, additional RGE sequences (for example, tandem repeats of RGE sequences) may be included in a modulating agent.

Linkers may or may not be used to separate RGE sequences in a Trk modulator, including tandem repeats of RGE sequences (such as in preferred Trk agonists of the invention). Linkers can also be used to attach a modulating agent of the invention to a solid support or material, as described below.

A linker may be any molecule (including peptide and/or non-peptide sequences as well as single amino acids or other molecules), that does not contain a RGE sequence and that can be covalently linked to at least two peptide sequences and/or peptidomimetics. Using a linker, peptidomimetics and other peptide or protein sequences may be joined in a variety of orientations.

Linkers preferably produce a distance between CAR sequences and/or peptidomimetics between 0.1 to 10,000 nm, more preferably about 0.1–400 nm. A separation distance between recognition sites may generally be determined according to the desired function of the modulating agent. For Trk antagonists, the linker distance should be small (0.1–400 mm). For Trk agonists, the linker distance should be 400–10,000 nm. One linker that can be used for such purposes is $(H_2N(CH_2)_nCO_2H)_m$, or derivatives thereof, where n ranges from 1 to about 10 and m ranges from 1 to about 4000. For example, if glycine $(H_2NCH_2CO_2H)$ or a multimer thereof is used as a linker, each glycine unit corresponds to a linking distance of about 2.45 angstroms, or 0.245 nm, as determined by calculation of its lowest energy conformation when linked to other amino acids using molecular modeling techniques. Similarly, aminopropanoic acid corresponds to a linking distance of about 3.73 angstroms, aminobutanoic acid to about 4.96 angstroms, aminopentanoic acid to about 6.30 angstroms and amino hexanoic acid to about 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms.

Peptide and non-peptide linkers may generally be incorporated into a modulating agent using any appropriate method known in the art.

Modulating agents that are Trk antagonists may contain one or more peptidomimetics. Preferably such peptidomimetics are adjacent to one another (i.e., without intervening sequences) or are in close proximity (i.e., separated by peptide and/or non-peptide linkers to give a distance between the peptidomimetics that ranges from about 0.1 to 400 nm). It will be apparent that other neurotrophin sequences, as discussed above, may also be included.

As noted above, a modulating agent may consist entirely of one or more peptidomimetics, or may contain additional peptide and/or non-peptide components. Peptide portions may be synthesized as described above or may be prepared using recombinant methods. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous neurotrophin. Such sequences may be prepared based on known Cdna or genomic sequences, or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous neurotrophin. To generate a nucleic acid molecule encoding a peptide portion of a modulating agent, an endogenous sequence may be modified using well known techniques. Alternatively, portions of the desired nucleic acid sequences may be synthesized using well known techniques, and then ligated together to form a sequence encoding a portion of the modulating agent.

Trk modulating agents of the present invention may additionally comprise an antibody, or antigen-binding fragment thereof, that specifically binds to a NT sequence or, alternatively an antibody or antigen-binding fragment thereof that specifically binds to a Trk receptor sequence. As used herein, an antibody, or antigen-binding fragment thereof, is said to "specifically bind" to a NT or Trk sequence (with or without flanking amino acids) if it reacts at a detectable level (within, for example, an ELISA, as described by Newton et al., *Develop. Dynamics* 1993, 197: 1–13) with a peptide containing that sequence, and does not react detectably with peptides containing a different NT or Trk sequence, nor with a sequence in which the order of amino acid residues in the NT (or Trk) and/or flanking sequence is altered.

Antibodies and fragments thereof may be prepared using standard techniques. See, e.g., Harlow & Lane, *Antibodies: A Laboratory Manual*, Cold Spring Harbor Laboratory, 1988. In one such technique, an immunogen comprising a NT or Trk sequence is initially injected into any of a wide variety of mammals (e.g., mice, rats, rabbits, sheep or goats). Small immunogens (i.e., less than about 20 amino acids) are preferably joined to a carrier protein, such as bovine serum albumin or keyhole limpet hemocyanin. Following one or more injections, the animals are bled periodically. Polyclonal antibodies specific for the NT or Trk sequence may then be purified from such antisera by, for example, affinity chromatography using the modulating agent or antigenic portion thereof coupled to a suitable solid support.

Monoclonal antibodies specific for a NT (or Trk) sequence may be prepared, for example, using the technique of Kohler & Milstein, (*Eur. J. Immunol.* 1976, 6:511–519) and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within certain embodiments, monoclonal antibodies may be specific for particular NTs or, alternatively, for particular Trk receptors. For example, the antibody may bind to NGF, but do not bind to BNDF, or vice versa. As another example, a monoclonal antibody may bind specifically to TrkB and not bind specifically to TrkA, or vice versa. Such antibodies may be prepared as described above, using (to generate antibodies for a particular NT) an immunogen that comprises the RGE sequence and also sufficient flanking sequence to generate the desired specificity (e.g., 5 amino acids on each side is generally sufficient). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular Trk-expressing cell, such as a particular neuronal cell.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow & Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow & Lane, 1988, pages 628–29).

6.5. Evaluation of TRK Modulator Activity

As noted above, peptidomimetics, cyclic peptides and other Trk modulators of the invention are capable of modulating (i.e., enhancing or inhibiting) Trk mediated activities including, for example, neuronal survival, axonal growth and synaptic plasticity. Hence, the ability of a modulating agent (or a suspected modulating agent) to modulate Trk mediated activity can generally be evaluated either in vitro or in vivo by assaying one or more of these effects. Generally speaking, a test compound is a Trk antagonist if, within such a representative assay, contact of test cells with the candidate results in a discernible disruption of the Trk mediated activity being measured. A candidate compound is generally considered a Trk agonist if, within such a representative assay, contact of test cells with the candidate compound results in a discernible increase of the Trk mediated activity measured.

In particular, preferred embodiments of the invention, the activity of a Trk modulator or candidate compound is evaluated in vivo in a neurite outgrowth assay. Within a representative neurite outgrowth assay, which is demonstrated in the Examples, infra, neurons may be cultured on a monolayer of cells (preferably 3T3 cells or cell lines derived therefrom). As an example, monolayers of 3T3 fibroblasts can be established by overnight culture of cells (preferably about 80,000) in individual wells of an 8-chamber well tissue culture slide. Approximately 3,000 cerebellar neurons isolated from post natal day 3 (PND3) mouse brains may be cultured for 18 hours on the various monolayers in control media (SATO/2% FCS) or in media supplemented with various concentrations of the candidate modulating agent. Alternatively, the cells may be cultured in media supplemented with a control peptide (for example, a non-cyclic, linear peptide having the same amino acid sequence as a Trk modulator cyclic peptide) or with a neurotrophin (e.g., NGF, BDNF, NT-3, NT-4, NT-5 or NT-4/5).

The cell cultures may then be fixed and stained for GAP43 or with some other agent that specifically binds neurons and their neurites. The length of the longest neurite on each GAP43 positive neuron may then be measured, preferably using computer assisted morphometry. A compound that is a Trk modulator will generally modulate (e.g., inhibit or enhance) neurite outgrowth in such a cell culture assay.

6.6. Uses of TRK Receptor Modulators

In general, modulating agents and compositions of the present invention can be used for modulating (e.g., inhibiting or enhancing) activities that are mediated by a Trk receptor—including activities mediated by TrkA, TrkB and/or TrkC. Trk receptors are implicated in the growth and repair of the central nervous system (CNS) and mediate, at least in part, such processes as neuronal survival, axonal growth, neurite outgrowth, synaptic plasticity and, more generally, neurological growth. Hence, modulating agents and compositions of the invention can be used to modulate any of these processes. Such uses include, inter alia, therapeutic methods and pharmaceutical compositions for treating conditions, diseases and disorders that are associated with such processes. Exemplary conditions, diseases and disorders include Alzheimer's disease, Parkinson's disease, stroke, and head and spinal cord injury to name a few.

In one embodiment of the invention, Trk agonist of the invention can be used to increase or enhance activities that are mediated by a Trk receptor. Hence, Trk agonist of the invention may be used, e.g., to increase or enhance the growth and/or repair of the CNS, for example by increasing or enhancing such processes a neuronal growth, neuronal survival, axonal growth, neurite outgrowth and synaptic plasticity. Trk agonists of the invention are therefore useful, e.g., in therapeutic methods for treating diseases and disorders that involve or are otherwise associated with damage to or impaired function of the central nervous system. These include, inter alia, the disease and disorders listed above.

In other embodiments, Trk antagonists of the invention can be used to decrease or inhibit activity mediated by a Trk receptor. Thus, Trk antagonists may inhibit processes such as neuronal growth, neuronal survival, axonal growth, neurite outgrowth and synaptic plasticity. Trk antagonists are also useful in therapeutic methods, for example to treat or ameliorate diseases and disorders (for example, epilepsy) that are associated either with increased Trk receptor activity, or with increased activity of a neurotrophin (for example, BDNF) that binds to and activates a Trk receptor.

In still other embodiments, Trk agonists and antagonists of the invention can also be used to modulate responses that inhibit CNS growth and repair (i.e., "CNS inhibitors"), including responses that inhibit processes such as neuronal growth, neuronal survival, axonal growth, neurite outgrowth and synaptic plasticity. In particularly preferred embodiments, Trk agonists of the invention (for example a $B_{AG}$ or other agonist polypeptide or peptide mimetic) can be used to block or reduce a CNS inhibitor response. In other embodiments of the invention, Trk agonists (for example, a $B_{AG}$ or other agonist polypeptide or peptide mimetic) can be used to enhance and/or promote neuronal growth and recovery, even administered in an inhibitory environment such as in the presence of one or more CNS inhibitors.

As a particular example, it is understood that inhibitory factors, such as those associated with myelin, exists which can inhibit or even prevent processes of CNS growth and repair, including those recited above. Examples of such inhibitors include, but are not limited to, the myelin associated glycoprotein (also referred to as "MAG"), Nogo-A and the oligodendrocyte myelin glycoprotein. For a more complete description of such inhibitors, see also Section 3.3 above. Trk agonists and antagonists of the invention can be used to modulate responses that are produced by these and other CNS inhibitors.

Without being limited to any particular theory or mechanism of action, it is understood that Trk receptors modulate CNS growth and repair at least in part by a mechanism or mechanisms that involve protein kinase A (PKA) and phosphinositide 3-kinase (PI3K). Accordingly, Trk agonists and antagonists of the invention can, in preferred embodiments, modulate effects of inhibitory signals that are mediated by one or more components which are themselves modulated by either PKA or PI3K. As an example, and not by way of limitation, PKA is understood to activate Rho by direct phosphorylation on Ser188 of that molecule (Ellerbroek et al., *J. Biol. Chem.* 2003, 278:19023–19031). Hence, Trk agonists and antagonists of the present invention can be used to modulate signals mediated by inhibitory cascades involving Rho. These include, inter alia, inhibitory signals mediated by myelin inhibitors such as MAG (and MAG fusion constructs such as MAG-Fc), Nogo-A, the oligodendrocyte myelin glycoprotein, NgR, GT1b and $p75^{NTR}$. Other CNS inhibitors involving Rho include signals mediated by chondroitin sulfate proteoglycans from CNS glial scar (Monnier et al., *Neurosci.* 2003, 22:319–330) and, as such, these CNS inhibitors can also be modulated by Trk agonists and antagonists of the invention. As another non-limiting example, activation of PI3K is expected to overcome inhibitory activity of semaphorins (Eickholt et al., *J. Cell Biol.* 2002, 157:211–217). Hence, Trk agonists and antagonists of the present invention can additionally be used to modulate these CNS inhibitors.

In general, methods of the invention involve contacting a cell expressing a Trk receptor (typically a neuronal cell) with a Trk modulating agent either in vivo or in vitro. The amount of Trk modulating agent administered should be an "effective amount"—that is to say, it should be an amount that effectively modulates a Trk mediated activity of interest or, alternatively, an amount that effectively modulates a CNS inhibitor of interest. In embodiments where the Trk modulator is administered as part of a therapeutic method, amount administered should be an amount that effectively ameliorates (but does not necessarily eliminate or cure) the condition, disease or disorder being treated. Alternatively, the amount administered may be an amount effective to ameliorate (but not necessarily eliminate) one or more symptoms associated with the condition, disease or disorder being treated.

As a particular, non-limiting example, a Trk modulating agent of the invention can be used to modulate (e.g., inhibit or enhance) neurological growth, such as neurite outgrowth. In such methods, neurite outgrowth may be enhanced and/or directed by contacting a neuron with one or more Trk agonists of the invention (e.g., the cyclic peptide N-Ac-CSRRGELAASRRGELC-NH$_2$(SEQ ID NO:18)). Alternatively, neurite outgrowth may be inhibited and/or decreased by contacting a neuron with one or more Trk antagonists of the invention (e.g., the cyclic peptide N-Ac-CSRRGEC-NH$_2$(SEQ ID NO:2)). Preferred modulating agents for use within such methods are preferably linked to a polymeric matrix or other support, and comprise a cyclic peptide as described in Section 6.1, supra, or a peptidomimetic thereof (as described in Section 6.3). Modulating agents comprising antibodies, or fragments thereof, may also be used in such methods, with or without the use of linkers or support materials.

The method of achieving contact to the neuronal cell and the amount of Trk modulating agent administered will depend upon the location of the neuron as well as the extent and nature of desired outgrowth (or, where Trk antagonists are administered, the extend and nature of desired inhibition). For example, a neuron may be contacted (e.g., via implantation) with one or more Trk modulating agents linked to a support material such as a suture, fiber nerve guide or other prosthetic device so that the neurite outgrowth is directed along the support material. Alternatively, a tubular nerve guide may be employed in which the lumen of the nerve guide contains a composition comprising the modulating agent or agents. In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

6.7. TRK Receptor Modulators: Formulations

In certain embodiments, a modulating agent as described herein may, but need not, be linked to one or more additional molecules. For example, it may be beneficial for certain applications to link multiple modulating agents (which may, but need not, be identical) to a support molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012).

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent or linker). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other NT and/or Trk receptor sequences may be attached, for example, by random coupling, in which equimolar amounts of such molecules are mixed with a matrix support and allowed to couple at random.

Although modulating agents as described herein may preferentially bind to specific tissues or cells (i.e., neuronal cells and tissues), and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. An antibody targeting agent may be an intact (whole) molecule, a fragment thereof, or a functional equivalent thereof. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Within certain aspects of the present invention, one or more modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A modulating agent (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration. For certain topical applications, formulation as a cream or lotion, using well known components, is preferred.

Optionally, a pharmaceutical composition may also contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include but are not limited to analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a calorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710, 491A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and the duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.2%, and more preferably from 0.0001% to 0.002%. Fluid compositions typically contain about 10 ng/ml to 5 mg/ml, preferably from about 10.mu.g to 2 mg/Ml peptidomimetic. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Trk receptor modulators can also be formulated according to the description provided in section 6.9, infra.

6.8. p75 Binding Agents

The term "p75 receptor binding agent" is used herein to describe a naturally-occurring or synthetic (e.g., recombinant) molecule, which binds to a p75 receptor engaged in an inhibitory complex, and interferes with p75 receptor:neurotrophin interaction but not neurotrophin:Trk receptor interaction. Thus, a p75 receptor binding agent facilitates neurotrophin-mediated neuron growth in an inhibitory environment. A p75 receptor is engaged in an inhibitory complex when it interacts with a nogo receptor and any of the myelin-associated proteins (e.g., MAG, Nogo-A, oligodendocyte myelin glycoprotein). Examples of p75 receptor binding agents include, but are not limited to, neurotrophins, such as NGF, and agents derived from neurotrophins, such as the NGF binding loop-derived N-Ac-CTDIKGKEC-NH$_2$ (SEQ ID NO:43). A neurotrophin is a p75 receptor binding agent according to the invention if it interferes with binding of another, different neurotrophin to the p75 receptor and does not interact with the Trk receptor expressed on the injured neuron. For example, in the case of neurons that express TrkB but not TrkA, the neurotrophin NGF is a p75 receptor binding agent because NGF will compete (i.e., interfere) with a neurotrophin that binds TrkB (e.g., BDNF) for p75 receptor binding but will not interfere with neurotrophin binding (e.g., BDNF) to the TrkB receptor.

In a preferred embodiment, a p75 receptor binding agent comprises at least one cyclic peptide or peptidomimetic compound containing the NGF motif TDIKGKE (i.e., Thr-Asp-Ile-Lys-Gly-Lys-Glu) (SEQ ID NO:42) within a cyclic ring of the cyclic peptide or peptidomimetic compound. An especially preferred p75 receptor binding agent is N-Ac-CTDIKGKEC-NH$_2$ (SEQ ID NO:43). As noted previously, underlined peptide sequences denote a peptide that has been cyclised by a covalent bond between the two last underlined residues. In these examples, the p75 binding agents were cyclized by a disulfide bond between two cysteine residues, acetylated and amide blocked. It is understood that preferred peptides which bind to a p75 receptor will be constrained and, hence, are preferably cyclic peptides. Methods for cyclization of peptides are described in section 6.1, supra.

Multiple cyclic peptides and/or peptidomimetics can be present in a p75 receptor binding agent. Moreover, additional TDIKGKE (SEQ ID NO:42) sequences (for example, tandem repeats of TDIKGKE (SEQ ID NO:42) sequences) may be included in a p75 receptor binding agent.

Linkers may or may not be used to separate p75 receptor binding sequences in a p75 receptor binding agent, including tandem repeats of p75 receptor binding sequences. A linker may be any molecule (including peptide and/or non-peptide sequences as well as single amino acids or other molecules), that can be covalently linked to at least two peptide sequences and/or peptidomimetics, and does not contain a p75 receptor binding sequence. Using a linker, peptidomimetics and other peptide or protein sequences may be joined in a variety of orientations.

p75 receptor binding agents may contain one or more peptidomimetics. Preferably such peptidomimetics are adjacent to one another (i.e., without intervening sequences) or are in close proximity (i.e., separated by peptide and/or non-peptide linkers to give a distance between the peptidomimetics that ranges from about 0.1 to 400 nm). A p75 receptor binding agent may consist entirely of one or more peptidomimetics, or may contain additional peptide and/or non-peptide components. Methods for making a peptidomimetic are described in sections 6.2 and 6.3, supra.

All or part of a p75 receptor binding agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous neurotrophin. Such sequences may be prepared based on known cDNA or genomic sequences, or from sequences isolated by screening an appropriate library. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous neurotrophin. To generate a nucleic acid molecule encoding a peptide portion of a modulating agent, an endogenous sequence may be modified using well known techniques. Alternatively, portions of the desired nucleic acid sequences may be synthesized using well known techniques, and then ligated together to form a sequence encoding a portion of the p75 receptor binding agent.

6.9. p75 Binding Agents: Methods for Promoting CNS Growth

The present invention provides methods for promoting CNS growth, which comprise administering a p75 receptor binding agent. Trk receptors are implicated in the growth and repair of the CNS and mediate such processes as neuronal survival, axonal growth, neurite outgrowth, synaptic plasticity, and more generally, neurological growth. p75 receptors bind neurotrophins with low affinity and this binding compromises the ability of neurotrophins to activate Trk receptors in the situation where the p75 receptor is engaged in an inhibitory complex. Hence, methods which interfere with the binding of neurotrophins to p75 receptor allows neurotrophins to bind to and activate Trk receptors, and thus promote CNS neuron growth in an inhibitory environment.

In an aspect of the present invention, a method is provided which comprises administering to an individual a therapeutically effective amount of a p75 receptor binding agent in combination with at least one neurotrophin. A preferred neurotrophin is NGF, BDNF, NT-3, NT-4 or NT-5. In one embodiment, the p75 receptor binding agent is administered in an amount about 10 to about 100 fold greater than that of the neurotrophin. In another embodiment, the p75 receptor binding agent is NGF and the neurotrophin is BDNF. The methods of the present invention can be used to treat conditions, diseases and disorders that are associated with damage to or impaired function of the CNS. Exemplary conditions include, but are not limited to, Alzheimer's disease, Parkinson's disease, Huntington's disease, amyotrophin lateral sclerosis, stroke, traumatic brain injury, and spinal cord injury.

According to the methods of the present invention, a neurotrophin is a p75 receptor binding agent when the neurotrophin interferes with the binding of another, different neurotrophin to a p75 receptor engaged in an inhibitory complex, but does not interfere with the binding of the another, different neurotrophin to a Trk receptor expressed on an injured CNS neuron. For example, NGF is a p75 receptor binding agent according to the present invention if it is co-administered with BDNF to an individual with neurons that express the TrkB receptor because NGF competes with BDNF for binding to the p75 receptor but does not compete with BDNF for binding to the TrkB receptor.

A p75 receptor agent as described herein can be present within a pharmaceutical composition. A pharmaceutical composition comprises a p75 receptor binding agent in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. A p75 receptor binding agent (alone or in combination with a targeting agent and/or drug) can be encapsulated within liposomes using well known technology.

Compositions of the present invention may be formulated for any appropriate manner of administration, including for example, topical, intravenous, intracranial, intraperitoneal, subcutaneous, or intramuscular administration. Pharmaceutical compositions comprising a p75 receptor binding agent can be administered by any means that allows the p75 receptor binding agent to reach and bind with p75 receptors in the body of an individual.

Sterile injectable forms of pharmaceutical compositions comprising a p75 receptor binding agent can be aqueous or oleaginous suspensions. These suspensions may be formulated according to techniques known in the art using suitable dispersing or wetting agents and suspending agents. A sterile injectable preparation can also be a sterile injectable solution or suspension in a non-toxic parenterally-acceptable diluent or solvent. Among the acceptable vehicles and solvents that can be employed are sterile water, lactated Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant. A p75 receptor binding agent can also be formulated according to the description provided in section 6.7, supra.

p75 receptor binding agents can be administered topically. For example, a p75 receptor binding agent may be applied topically to the exposed spinal cord of an individual following spinal cord injury or during surgery. For topical application, a pharmaceutical composition can be formulated in a suitable ointment containing the p75 receptor binding agent suspended or dissolved in one or more carriers. Carriers for topical administration of p75 receptor binding agents include, but are not limited to, mineral oil, liquid petrolatum, white petrolatum, emulsifying wax, water, or absorbable materials, such as, for example, Type I collagen gel or gelatin hemostasis sponge (Gelfoam®, Pharmacia & Upjohn, Kalamazoo, Mich.).

Appropriate dosages and the duration and frequency of administration will be determined by such factors as the condition of the patient, the type and severity of the patient's disease and the method of administration. In general, an appropriate dosage and treatment regimen provides the p75 binding agent(s) in an amount sufficient to provide therapeutic and/or prophylactic benefit. Various considerations for determining appropriate dosages are described, e.g., in Gilman et al. (eds), *The Pharmacological Bases of Therapeutics*, 8$^{th}$ Ed. (1990), Pergamon Press. Appropriate dosages may generally be determined using experimental models and/or clinical trials. In general, the use of the minimum dosage that is sufficient to provide effective therapy is preferred. Patients can be monitored for therapeutic effectiveness using physical examination, imaging studies, or assays suitable for the condition being treated or prevented, which will be familiar to those of ordinary skill in the art. Dose adjustments can be made based on the monitoring findings. For example, an individual with a spinal cord injury associated with loss of sensation in an arm can be monitored, following administration of a p75 receptor binding agent according to the invention, for return of sensation to the arm by physical examination.

Compositions comprising a p75 receptor binding agent may be administered as part of a sustained release formulation (i.e., a formulation such as a capsule or sponge that effects a slow release of p75 receptor binding agent following administration). Such formulations may generally be prepared using well known technology and administered by, for example, subcutaneous implantation or implantation at the desired target site. Sustained-release formulations may contain a p75 receptor binding agent dispersed in a carrier matrix and/or contained within a reservoir surrounded by a rate-controlling membrane (see, e.g., European Patent Application 710,491A). Carriers for use within such formulations are biocompatible, and may also be biodegradable; preferably the formulation provides a relatively constant level of binding agent release. The amount of binding agent contained within a sustained release formulation depends upon the site of implantation, the rate and expected duration of release and the nature of the condition to be treated.

Although a p75 receptor binding agent as described herein may preferentially bind to specific tissues or cells (i.e., neuronal cells and tissues), and thus may be sufficient to target a desired site in vivo, it may be beneficial for certain applications to include an additional targeting agent. Accordingly, a targeting agent can be linked to a p75 receptor binding agent to facilitate targeting to one or more specific tissues. As used herein, a p75 receptor "targeting agent" may be any substance (such as a compound or cell) that, when linked to a p75 receptor binding agent, enhances the transport of the p75 receptor binding agent to a target tissue (i.e., a damaged neuron), thereby increasing the local concentration of the p75 receptor binding agent.

Targeting agents can include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. An antibody targeting agent may be an intact (whole) molecule, a fragment thereof, or a functional equivalent thereof. For example, a MAG, Nogo-A or myelin glycoprotein antibody can be a targeting agent. Examples of antibody fragments are F(ab')2, –Fab', Fab and F[v] fragments, which may be produced by conventional methods or by genetic or protein engineering. Linkage is generally covalent and may be achieved by, for example, direct condensation or other reactions, or by way of bi- or multi-functional linkers. Within other embodiments, it may also be possible to target a polynucleotide encoding a binding agent to a target tissue, thereby increasing the local concentration of binding agent. Such targeting may be achieved using well known techniques, including retroviral and adenoviral infection.

For certain embodiments, it may be beneficial to link a drug to a p75 receptor binding agent. For a description of drugs suitable for linking to a p75 receptor binding agent, see section 6.7, supra.

7. EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing the invention in spirit or in scope. The invention is therefore to be limited only by the terms of the appended claims along with the full scope of equivalents to which those claims are entitled.

7.1. Experimental Procedures

7.1.1 Neurite Outgrowth Assays

Co-cultures of cerebellar neurons on monolayers of either parental 3T3 cells or LK8 cells (an established transfected 3T3 cell line that expresses physiological levels of chick N-cadherin; see Doherty et al., *Neuron* 1991, 6:247–258) were established as previously described by Williams et al. (*Neuron* 1994, 13:583–594). The cells were maintained in Dulbecco's modified Eagle's medium supplemented with 10% foetal calf serum (FCS).

For establishment of the co-cultures, about 80,000 3T3 cells (or LK8 cells) were plated into individual chambers of an eight-chamber tissue culture slide coated with poly-L-lysine and fibronectin. The plated cells were maintained overnight in Dulbecco's modified Eagle's medium ("DMEM") supplemented with 10% FCS to allow for the formation of confluent monolayers. The medium was removed and about 6,000 dissociated cerebellar neurons (taken from post-natal day 9 rats) were plated into each well in SATO medium supplemented with 2% FCS. Test reagents were added as indicated in the text and the co-cultures maintained for 18 hours. The co-cultures were then fixed and stained for GAP-43 immunoreactivity. The mean length of the longest neurite per cell was measured for between about 120 and 150 neurons, again as previously described by Williams et al. (*Neuron* 1994, 13:583–594).

7.1.2 Molecular Modeling of TRK Receptor-Ligand Structures

X-ray crystallography structures of the NGF/TrkA and NT-4/TrkB complexes were used for molecular modeling. These structures have been previously described (See, respectively, Wiesmann et al. *Nature* 1999, 401:184–188; and Banfield et al. *Structue* (*Camb*) 2001, 9:1191–1199) and can be readily accessed, e.g., over the internet from the Protein Data Bank (PDB) under the accession numbers 1www (for NGF/TrkA) and 1hcf (for NT-4/TrkB). Swiss PDB software packages were used to isolate the structures of various motifs from the binding interfaces of the crystals, and Accelrys software was used to generate images.

Contact profiles were generated from various ligand/receptor interfaces at the NT-4/TrkB crystal structure by measuring the average number of receptor contacts per ligand residue against the ligand residue sequence number. The average was taken over a three residue window and the contact number is the number of receptor residues that are within five Angstroms of the given ligand amino acid.

7.1.3 Reagents

Recombined human FGF2, BDNF and NT-4/5 were all obtained from R&D systems (Minneapolis, Minn.). The CB1 cannabinoid receptor agonist WIN55,2122–2 mesylate was obtained and used as previously described (see, Williams et al., *J. Cell. Biol.* 2003, 160:481–486). The Trk receptor antagonist K252a was obtained from Calbiochem (San Diego, Calif.). The PD173074 FGFR antagonist (Mohammadi et al., *Embo J.* 1998, 17:5986–5904) was synthesized and used as previously described by Skaper et al. (*J. Neurochem.* 2000, 75:1520–1527) and by Hamby et al., *J. Med. Chem.* 1997, 40:2296–2303).

Synthetic peptides were all obtained from a commercial supplier (Multiple Peptide Systems, San Diego, Calif.). All peptides were purified by reverse-phase high performance liquid chromatography (RP-HPLC) according to routine methods, and obtained at the highest level of purity (i.e., greater than 95% pure). Where peptide sequences are underlined (throughout this specification) denotes a peptide that has been cyclised by a covalent bond between the two last underlined residues. In these examples, peptides were cyclized by a disulfide bond between two cysteine residues, acetylated and amide blocked.

7.2. Identification of a NT-4 Linear Peptide Sequence that Interacts with TrkB Receptor This section describes molecular modeling experiments that identify a suitable linear peptide (LIP) sequence from natural neurotrophin ligands that binds to a key site in a Trk receptor.

Considerable evidence suggests that the membrane proximal immunoglobulin (Ig) domain (D5) of the Trk receptor is directly involved in the binding of NTs. See, for example, Perez et al., *Mol. Cell Neurosci.* 1995, 6:97–105; and Urfer et al., *Embo J.* 1995, 14:2795–2805. Crystal structures of the NGF/TrkA complex (Wiesmann et al., *Nature* 1999, 401:184–188) and of the NT-4/TrkB complex (Banfield et al., Structure (Camb) 2001, 1191–1199) have been solved which support this view. In both structures, a single NT dimer engages to Trk receptor molecules with each NT molecule in the dimer interacting, in turn, with each Trk receptor molecule.

Both crystal structures were analyzed with an algorithm designed to highlight linear regions on the ligand that interact with the receptor (Doherty et al., *Mol. Cell Neurosci* 2000, 16:283–295). To illustrate this analysis, the NT-4/TrkB(D5) crystal structure is shown here in FIG. 6A. Within this complex, an individual NT monomer (labeled $a_1$) makes linear contacts with both TrkB receptor monomers (labeled $b_1$ and $b_2$). Both of these two interfaces were analyzed, and this analysis is illustrated in FIGS. 6B–6C. In these figures, interfaces between NGF and the TrkA receptor are shown by dotted lines, whereas the interfaces between NT-4 and TrkB are shown by a solid line. As can be seen from inspection of these two figures, the interfaces overlap considerably for these two ligand-receptor complexes.

The contact profile analysis indicates that the N-terminal of the NT ligand makes the most intimate contact with the Trk receptor (FIG. 6C). Moreover, a small linear motif (SRRGE) situated at the dominant peak in the contact profile exists as half a helix and can be considered a tight loop. The sequence is closely conserved in BDNF (ARRGE), which also binds to the TrkB receptor, and is partially conserved in NGF (FHRGE) and NT-3 (SHRGE), ligands for the TrkA and TrkC receptors, respectively. Interesting, this region of neurotrophins is disordered in crystal structures of unbound NT (see, McDonald et al., *Nature* 1991, 354:411–414) and therefore has not previously been the subject of peptide studies.

The $a_1/b_2$ interface contact profile is illustrated in FIG. 6B. NT loops 1–4, which others have implicated in the NT/Trk interaction (LeSauteur et al., *J. Biol. Chem.* 1995, 270:6564–6569) are highlighted. However, none of these loops figure in the $a_1/b_1$ interface and only loop 1 is involved in the $a_1/b_2$ interface.

7.3. Development of a TrkB Antagonist Peptide

Cerebellar neurons, isolated from rat pups at PND2, were cultured over monolayers of 3T3 fibroblasts in either control media or in media supplemented with a range of BDNF and/or NT-4 concentrations. After 16 hours, the co-cultures were fixed and mean neurite length determined as has been previously described (Williams et al., *J. Biol. Chem.* 2000, 275:4007–4012). The results, which are illustrated in FIG. 7A, show that both ligands stimulate neurite outgrowth in a dose-dependent manner with a maximal response seen at between about 1 and 10 ng/ml.

The results in Section 7.2, supra, suggest that a properly constrained peptide of the small linear RGE motif that is present in all NTs might have a high structural overlap with the native NT structure and thereby function as a Trk receptor antagonist. To test this hypothesis, a cyclic version of the LIP was designed that was constrained by a disulfide bond and has the amino acid sequence: N-Ac-CRGEC-NH$_2$(SEQ ID NO:9). The effect of this peptide on the BDNF and NT-4 response was tested in the above-described neurite outgrowth assay, with both NT ligands used at concentrations of 5 ng/ml. These results, which are illustrated in FIG. 7B show that the peptide antagonizes both the BDNF and the NT-4 response, with a 50% inhibition seen at 144±23 μM for the BDNF response and 112±22 μM for the NT-4 response. In contrast, the peptide has no effect on basal neurite outgrowth when tested at concentrations greater than about 400 μM and in the absence of any natural NT ligand. These results suggest that the cyclic peptide itself has no specific effects on neuronal survival and neurite outgrowth.

7.4. An NT-4 Lip is a More Potent TrkB Antagonist than Equivalent NT3 and NGF Lips The RGE sequence motif is shared by all the NTs. However, the amino sequences flanking this motif differ between the TrkA, TrkB and TrkC ligands. A series of "equivalent" peptides, designed from sequences of different NT ligands, was therefore tested to determine if an extended peptide from the TrkB ligand might be a more active TrkB receptor antagonist.

Molecular modeling studies suggest that the peptide N-Ac-CSRRGEC-NH$_2$ (SEQ ID NO:2) shares structural overlap with the natural SRRGE (SEQ ID NO:33) motif of NT-4. Accordingly, this peptide sequence was tested alongside equivalent peptides derived from NGF (N—Ac-CFHRGEC-NH$_2$ (SEQ ID NO:6)) and NT-3 (N-Ac-CSHRGEC-NH$_2$ (SEQ ID NO:7 with an acetylated N-terminal amino group and a C-terminal amide group)) for their ability to inhibit the BDNF and NT-4 responses in the neurite outgrowth assay described in Section 7.3, supra. Surprisingly, the N-Ac-CSRRGEC-NH$_2$ derived from NT-4 was approximately 5-fold better than the NGF and NT-3 derived peptides at inhibiting the BDNF response, with a 50% inhibition seen at 27±6 μM. These results are illustrated in FIG. 7C.

As noted, above, the addition of as little as two flanking amino acid residues from NT-4 increased the efficacy of the peptide up to five-fold against a TrkB response. Addition of the equivalent amino acids from either NGF or NT-3 had no discernable effect on the efficacy of the original cyclic RGE peptide, suggesting that the selectivity of NT binding may be determined, at least in part, by the nature of amino acid residues that immediately flank the RGE motif. Indeed, a considerable body of evidence suggests that specificity of Trk receptor binding is encoded by the amino terminal sequences of the NTs. See, for example, Urfer et al., *Embo J.* 1994, 13:5896–5909; and McInnes & Sykes, *Biopolymers* 1997, 43:339–366. These findings suggests that cyclic peptides and peptidomimetics of the invention can be targeted to particular Trk receptors (i.e., to a TrkA, TrkB or TrkC receptor) by selecting the RGE flanking amino acid sequences from an NT ligand that preferably binds to the desired Trk receptor.

The same qualitative response described supra, was seen when the peptides were tested against NT-4 (see, FIG. 7D). However, whereas 50% inhibition of the BDNF response could be obtained with only about 25 μM of the peptide N-Ac-CSRRGEC-NH$_2$ (SEQ ID NO:2), the same level of inhibition of the NT-4 response required the peptide to be used at about 55±4 μM.

As with the cyclic peptide N-Ac-CRGEC-NH$_2$ (SEQ ID NO:10), neither the N-Ac-CSRRGEC-NH$_2$ (SEQ ID NO:2) peptide nor its NGF or NT-3 equivalents had any effect on basal neurite outgrowth in control cultures not supplemented with a NT ligand. The peptides were also tested for their ability to inhibit the neurite outgrowth response stimulated by other agents, including N-cadherin, FGF2 or a CB1 receptor agonist. Cell growth responses produced by these agents have been described elsewhere (Williams et al., *J. Cell Biol.* 2003, 160:481–486) and, in particular, are not believed to involve Trk receptors. The results from those experiments are shown in FIG. 8. In particular, the cyclic peptides did not inhibit any of these responses, even when administered at concentrations that fully inhibited the NT-4 and BDNF responses. These data confirm that the cyclic peptides and peptide mimetics of this invention can fully inhibit Trk receptor function without any non-specific effects on neurite outgrowth.

The effects of the linear peptide N-Ac-SRRGELA-NH$_2$ (SEQ ID NO:27) were also evaluated in the neurite outgrowth assay against NT-4, BDNF and the other agents mentioned, supra. These results are also shown in FIG. 8. As expected, whereas the cyclic version of this peptide was a potent inhibitor of both the NT-4 and the BDNF responses, the linear peptide did not inhibit any of the response even when tested at concentrations up to 125 µM. Hence, peptides and peptidomimetics containing the RGE motif need to be constrained, e.g. by disulfide bonds, to be functional Trk receptor antagonists.

7.5. Development of a TrkB Agonist Peptide

In crystal structures of the NT-4/TrkB receptor complex, the SRRGE (SEQ ID NO:33) motif in NT-4 runs anti-parallel to itself in the NT-4 dimer. The corresponding motif exhibits a similar anti-parallel alignment in crystal structures of the NGF/TrkA receptor complex. Previously, a "tandem-repeat" mimetic approach has been used to develop peptide agonist of N-cadherin. See, Williams et al., *J. Biol. Chem.* 2002, 277:4361–4367. The anti-parallel arrangement of the RGE motif in neurotrophins suggests that the "tandem-repeat" approach might also be used to develop Trk receptor agonist peptides.

Molecular modeling supports the hypothesis that a tandem repeat of the NT-4 SRRGE (SEQ ID NO:33)sequence might be constrained in the cyclic peptide N-Ac-CSRRGELAASRRGELC-NH$_2$ (SEQ ID NO:18) (this peptide is also referred herein to as the "B$_{AG}$" peptide) in a manner that would allow for simultaneous engagement of two TrkB receptor monomers. A modeled structure of the B$_{AG}$ peptide, which emphasizes this point, is shown here at FIG. 9. The effect of the B$_{AG}$ peptide on neurite outgrowth was therefore tested in the assay described in Section 7.3 supra.

The results from such an experiment are illustrated in FIG. 10A. The peptide can be seen to stimulate neurite outgrowth in a dose-dependent manner, with an EC$_{50}$ of about 300 nM and a near maximal response at about 600 Nm. As with the result to the natural ligands BDNF and NT-4, the response of neurite outgrowth to the B$_{AG}$ peptide is biphasic (compare FIGS. 7A and 10A). Next, the B$_{AG}$ peptide's ability to stimulate axonal growth was compared to that of established growth promoting peptides. The data from these experiments, which are illustrated in FIG. 10B, demonstrate that at 6 µM the B$_{AG}$ peptide promotes axonal growth by the same extent as maximally active concentrations of NT-R, BDNF and FGF2.

7.6. TrkB Antagonists Inhibit the Agonist Peptide Response

To verify that the B$_{AG}$ peptide activates Trk receptor by binding to the same site as the monomeric peptide antagonists (described in Sections 7.3–7.4, supra), experiments were conducted to determine whether the peptide antagonist N-Ac-CSRRGEC-NH$_2$ (SEQ ID NO:2) could inhibit the B$_{AG}$ peptide's effects on neurite outgrowth. The results are shown in FIG. 11.

At 125 µM, the TrkB antagonist peptide can fully inhibit the activity of a maximally active concentration of the B$_{AG}$ peptide. In contrast, the linear version of this peptide (i.e., the peptide N-Ac-SRRGELA-NH$_2$ (SEQ ID NO:27)) had very little to no effect on B$_{AG}$ peptide activity in the neurite outgrowth assay. K252a, a compound which is reported to be a relatively specific Trk receptor antagonist (Tapley et al., *Oncogene* 1992, 7:371–381), also fully inhibited the response of neurite outgrowth to the B$_{AG}$ peptide. However, PD17304, a specific FGF receptor antagonist, did not inhibit the response.

These data establish that "tandem-repeat" cyclic peptides and peptidomimetics, based on the RGE motif, are specific and effective agonist of Trk receptors.

7.7. TRK Agonists Overcome Inhibitors of Neuronal Growth

This example describes additional experiments investigating the effect of Trk receptor agonists under conditions that normally inhibit neuronal growth. In particular, the experiments demonstrate that, unlike the natural Trk receptor ligand, Trk receptor agonists of the invention can counteract the activity of inhibitory molecules and/or their receptors.

7.7.1 Materials and Methods

Reagents and culture treatment. Unless otherwise noted here, reagents in the experiments set forth in this Section were obtained and as set forth supra, in Section 7.1.3 et seq. In particular, recombinant human FGF2 and BDNF were obtained from R&D systems (Minneapolis, Minn.) and used at final concentrations of 5 ng/ml. The Trk receptor agonist K252a was obtained from Calbiochem (San Diego, Calif.) and used at a final concentration of 100 nM. The Trk agonist peptide B$_{AG}$ (SEQ ID NO:18) was obtained from a commercial supplier (Multiple Peptide Systems, San Diego Calif.). Recombinant MAG-Fc chimera was obtained from R&D Systems (Minneapolis, Minn.) and used at a final concentration of 5–25 µg/ml. Monoclonal antibody to GT1b (clone GMR5) was obtained from Seikagaku America (Falmouth, Mass.) and used at a final concentration of 20 µg/ml. A p75 NTR rabbit polyclonal antibody was raised against the extracellular domain of that receptor as previously described (see, Huber & Chao, *Dev. Biol.* 1995, 167:227–238) and used at a 1:200 dilution of serum. The known PKA inhibitors KT5720 and H-89 were obtained from Calbiochem (San Diego, Calif.) and used at final concentrations of 200 and 400 nM, respectively. The known PI3K inhibitors Wortmnannin and LY294002 were also obtained from Calbiochem (San Diego, Calif.) and were both used at final concentrations of 10 µM. The Rho kinase inhibitor Y27632 was obtained from Tocris (Bristol, UK) and used at 10 µM final concentration.

All reagents were diluted into the co-culture media and in general added to the cultures just prior to plating of the neurons. The exception was antiserum raised against the p75$^{NTR}$ receptor. Instead, a high density neuronal suspension was treated with a 1:200 dilution of the serum for 60 minutes. The neurons were then diluted by a factor of about 20, and seeded out for culture. The residual amount of p75$^{NTR}$ antibody in the cultures is estimated to have been approximately a 1:5000 dilution of the serum. Separate control experiments demonstrated that this antibody had no effect on neurite outgrowth at a dilution of 1:1000, establishing that the 1:5000 dilution used in these experiments has, at most, a negligible effect.

Neurite outgrowth assays. Neurite outgrowth assays were performed as described in Section 7.1.1, supra.

7.7.2 Results

The Trk receptor agonist B$_{AG}$ block MAG inhibitory activity. Myelin associated glycoprotein (MAG) has been previously shown to inhibit neurite outgrowth response from post-natal day 2–3 rat cerebellar neurons when presented to those cells as either a transfected molecule in the cellular substrate (Mukhopadhyay et al., *Neuron* 1994, 13:757–767) or when added as a soluble Fc chimeric protein (Tang et al., *Mol. Cell. Neurosci.* 1997, 9:333–346). In furtherance of those studies, post-natal day 3 cerebellar neurons were cultured over monolayers of LK8 cells, a 3T3 fibroblast cell line that express transfected N-cadherin and have been previously shown to promote a robust neurite outgrowth response (Williams et al., Neuron 1994, 13:583–594). Cells were cultured with soluble MAG-Fc fusion protein present in the culture medium at concentrations of 0, 5 or 25 μg/ml. As expected, MAG-Fc inhibited neurite outgrowth in a dose-dependent manner, with an approximately 40% inhibition response when present in the culture medium at a concentration of 25 μg/ml (see, FIG. 12).

Previous reports have suggested that inhibitors such as MAG mediated their effect(s) by activation of RhoA and/or its downstream effector Rho kinase. See, for example, Dergham et al., J. Neurosci. 2002, 22:6570–6570; Fournier et al., J. Neurosci. 2003, 23:1416–1423; and Lehmann et al., J. Neurosci. 1999, 19:7537–7547. To confirm these reports, cells were also cultured with the known Rho kinase inhibitor Y27632 (Narumiya et al., Methods Enzymol. 2000, 325:273–284; Davies et al., Biochem. J. 2000, 351:95–105) included in the culture medium at a concentration of 10 μM. As expected, MAG-Fc does not inhibit neurite outgrowth under these conditions, even when present in the culture medium at concentrations as high as 25 μg/ml (FIG. 12).

Additional neurite outgrowth experiments were performed to investigate what effect, if any, a Trk agonist might have on inhibitors such as MAG. In these experiments, neurons were cultured with the Trk agonist polypeptide $B_{AG}$ (SEQ ID NO:18, described in Section 7.5 above) present in the culture medium at a concentration of 6 μM. Surprisingly, MAG-Fc failed to inhibit neurite outgrowth under these conditions, even when present in the culture medium at concentrations as high as 25 μg/ml (FIG. 12). By contrast, when the neurotrophin BDNF was present in the culture medium at a concentration of 5 ng/ml there was no measurable effect on the MAG response—i.e., MAG-Fc continued to inhibit neurite outgrowth (FIG. 12). This result is consistent with previous reports that neuron cells must be "primed" with neurotrophins to circumvent the inhibitor activity of MAG and myelin (see, Cai et al., Neuron 1999, 22:89–101).

To further investigate the $B_{AG}$ polypeptide's ability to block MAG inhibitor activity, the polypeptide was tested in neurite outgrowth assays at a variety of different concentrations in the culture medium. Results from these experiments are depicted graphically in FIG. 13. These data show that the $B_{AG}$ polypeptide effectively blocks MAG inhibitor activity when present in the culture medium at concentrations as low as 30 nM, with a half maximal response when present at concentrations of between about 100 and 200 nM.

To confirm that the results from these experiments were not caused by any specific MAG inhibition of the N-cadherin component in neurite outgrowth, experiments were also performed with neurons cultured over monolayers of 3T3 fibroblasts cells that do not express transfected N-cadherin. Bar graphs showing data from these experiments are shown in FIG. 14. Although the basal neurite outgrowth response is lower when cells are cultured under these conditions, MAG-Fc nevertheless produces a measurable and substantial inhibition of neurite outgrowth when present at 25 μg/ml. In the absence of MAG-Fc, basal levels of neurite outgrowth are already robust, and the $B_{AG}$ polypeptide does not have a substantial effect when present in the culture medium at a concentration of 6 μM. Inspection of FIG. 14, however, reveals that the Trk-receptor agonist at this concentration does effectively block the MAG response, so that MAG-Fc fails to inhibit neurite outgrowth when present at a final concentration of 25 μg/ml. As before, and again in contrast to the effect of $B_{AG}$, the neurotrophin BDNF has no apparent effect on the inhibitory response stimulated by MAG-Fc when present at a concentration of 5 ng/ml.

These experiments demonstrate that Trk receptor agonists such as the $B_{AG}$ polypeptide can be used to effectively prevent or reduce inhibitory responses produced by signaling molecules such as MAG. The results from these experiments additionally show that Trk receptor agonists (e.g., $B_{AG}$) promote neuronal growth and recovery, even when administered in an inhibitory environment, such as in the presence of the inhibitory signaling molecule MAG.

$B_{AG}$ blocks inhibition by GT1b. The $B_{AG}$ polypeptide's ability to circumvent inhibitory activity of GT1b was also treated in neurite outgrowth assays. Previous reports have described multivalent IgM antibodies to GT1b that can inhibit neurite outgrowth from cerebellar granule cells (Vinson et al., J. Biol. Chem. 2001, 276:20280–20285). To confirm these reports, cerebellar neurons were cultured over monolayers of N-cadherin expressing 3T3 cells in both control media and in media containing 20 μg/ml of monoclonal antibody for GT1b. Data from these experiments are shown in the bar graph at FIG. 15. Consistent with previous reports, co-culturing the cells with 20 μg/ml of antibody robustly inhibits neurite outgrowth under these conditions. Compare the column labeled (1) in FIG. 15 to column C in that same figure. Co-culturing cells with 10 μM of the Rho kinase inhibitor Y27632 effectively abolishes this effect, confirming previous reports that the GT1b receptor involves Rho kinase as a downstream effector in its signal cascade (see, Vinson et al., J. Biol. Chem. 2001, 276:20280–20285). Surprisingly, when the Trk-receptor agonist $B_{AG}$ is present in the culture medium (6 μM) with antibody to GT1b, the antibody's inhibitor effect is effectively eliminated; i.e., a level of neurite outgrowth is observed which is comparable to that seen when antibody is not present in the culture medium. Compare the column labeled (2) in FIG. 15 to column C in that same figure.

These results show that Trk receptor agonists such as the $B_{AG}$ polypeptide can be used to effectively reduce or prevent inhibitory activity produced by such receptors such as GT1b. The results from these experiments additionally show that Trk receptor agonists (e.g., $B_{AG}$) promote neuronal growth and recovery, even when administered in an inhibitory environment, such as in the presence of the inhibitory signaling by GT1b.

$B_{AG}$ blocks inhibition by $p75^{NTR}$. Because inhibitory molecules in myelin are believed to signal either directly or indirectly via the $p75^{NTR}$ receptor, the $B_{AG}$ peptide's ability to circumvent that receptor's inhibitory activity was also investigated. To verify, first, that signaling from this receptor does inhibit neurite outgrowth, cerebellar neurons were cultured over monolayers of N-cadherin expressing 3T3 cells in both control media and in media containing polyclonal antibody to $p75^{NTR}$ (1:200 serum dilution).

Data from these experiments are presented in the bar graph at FIG. 16. Pretreatment of the cells with antibody for 60 minutes effectively inhibits the subsequent outgrowth of neurons, as can be seen by visually comparing the columns labeled (1) and C in the bar graph at FIG. 16. As with MAG and GT1b, antibody to p75NTR does not elicit an inhibitory response when the Rho kinase inhibitor Y27632 is added to neurons at a final concentration of 10 μM immediately after antibody treatment (see column (2) in FIG. 16). Likewise, culturing the neurons with a final $B_{AG}$ polypeptide concentration of 6 μM also effectively blocks the $p75^{NTR}$ antibody's inhibitory effect. However, culture the cells with the neurotrophin BDNF (5 ng/ml final concentration) has no significant effect on the inhibitory response elicited by p75$^{NTR}$ antibody.

Because the cell cultures may contain some residual amount of antibody (estimated to be no more than approximately 1:5000 serum dilution) after treatment, control experiments were performed in which cells were cultured with polyclonal antibody in the media at a 1:1000 serum dilution. The presence of antibody at this level had no measurable effect on neurite outgrowth, demonstrating that the effects observed in these experiments are not caused by the very low levels of residual antibody that may remain after treatment.

The results from these experiments demonstrate that Trk receptor agonists such as the B$_{AG}$ polypeptide can be used to effectively reduce or prevent inhibitory responses produced by the p75$^{NTR}$ pathway. he results additionally show that Trk receptor agonists (e.g., B$_{AG}$) promote neuronal growth and recovery, even when administered in an inhibitory environment, such as in the presence of the inhibitory signaling by p75$^{NTR}$.

B$_{AG}$ signaling is mediated by PKA and PI3K. To further investigate mechanisms by which a Trk receptor agonists may block inhibitory signals, cerebellar neurons were cultured for 18 hours over 3T3 monolayers in control media or in media supplemented with what hade been determined to be maximally active concentrations of either the B$_{AG}$ polypeptide (6 µM final concentration), the neurotrophin BDNF (5 ng/ml final concentration) or FGF2 (5 ng/ml final concentration). Findings from these experiments are depicted in the bar graph at FIG. 17. Under these conditions, each of the three factors (B$_{AG}$, BDNF and FGF2) enhances neurite length by about 60–70% compared to the control culture. When K252a, a compound which is reported to be a relatively specific Trk receptor antagonist (Tapley et al., *Oncogene* 1992, 7:371–381), was included in the culture media at a final concentration of 100 nM, the outgrowth response produced by both B$_{AG}$ and BDNF were essentially abolished. However, the outgrowth response produced by FGF2 was unaffected, confirming reports suggesting that FGF2 promotes neurite outgrowth by a signaling cascade that is distinct from that of Trk receptors and, in particular, does not involve either PKA or PI3K (see, Williams et al., *Cell Biol.* 2003, 160:481–486).

In similar experiments, neuronal cells were cultured either with the protein kinase A (PKA) inhibitor KT5720 (200 nM final concentration) or H-89 (400 nM final concentration), or with the phosphoinositide 3-kinase (PI3K) inhibitor Worthmannin (10 µM final concentration) of LY294002 (10 µM final concentration) in the culture media. As with the Trk receptor antagonist, the neurite outgrowth response to both B$_{AG}$ and BDNF was essentially abolished by these kinase inhibitors. As expected, the neurite outgrowth response to FGF2 was unaffected.

These results demonstrate that the activated Trk receptor stimulates neurite growth by a mechanism or mechanisms that involve activation of both PKA and PI3K. Hence, Trk agonists of this invention (e.g., the B$_{AG}$ polypeptide) can be effective at blocking or reducing a wide variety of inhibitory signals. In particular, Trk agonists of the invention can be effective at blocking inhibitory signals mediated by signal cascades with one or more components that are inhibited or inactivated by either PKA or PI3K.

As an example, and not be way of limitation, PKA is reported to inactivate Rho by direct phosphorylation on Ser188 of that molecule (Ellerbroek et al., *J. Biol. Chem.* 2003, 278:19023–19031). Hence, Trk agonists of the present invention can be used to block or reduce signals mediated by inhibitory cascades involving Rho. These include, inter alia, inhibitory signals mediated by myelin inhibitors such as MAG (or by MAG fusion constructs such as an MAG-Fc), Nogo-A, the oligodendrocyte myelin glycoprotein, NgR, GT1b and p75NTR as well as signals mediated by chondroitin sulfate proteoglycans from the CNS glial scar (Monnier et al. *Neurosci.* 2003, 22:319–330). As another non-limiting example, activation of PI3K is expected to overcome inhibitory activity of semaphorins (Eickholt et al., *J. Cell Biol.* 2002, 157:211–217). Indeed, neurotrophins are reported to overcome such inhibitor signaling by activating a Trk-PI3K cascade in neurons (Atwal et al., *J. Neurosci.* 2003, 23:7602–7609). Hence, Trk agonists of the present invention can be used to block or reduce these inhibitory signals as well.

7.8. Additional TRK Agonist Compounds

This example describes additional peptides and peptidomimetic compounds that are either based on or derived from the B$_{AG}$ polypeptide described in the preceding examples. Data from biological assays are also presented, demonstrating that these novel compounds also exhibit activity as Trk receptor agonists.

7.8.1 Novel TRK Receptor Agonists

The following peptides and peptidomimetics were designed based on the amino acid sequence of the B$_{AG}$ polypeptide described supra—i.e., CSRRGELAASRRGELC (SEQ ID NO:17). These novel compounds, which are referred to here as hB$_{AG2}$, riB$_{AG1}$ and hriB$_{AG2}$, are set forth in Table 1, below.

TABLE I

TRK RECEPTOR AGONIST COMPOUNDS

| Identifier | Sequence | | Key |
|---|---|---|---|
| hB$_{AG2}$ | c(SRRGELSRRGEL) | (SEQ ID NO:39) | cyclized peptide bond. |
| riB$_{AG1}$ | Ac-dCdLdEGdRdRdSdAdAdLdEGdRdRdSdC-NH$_S$ | (SEQ ID NO:40) | D-amino acid residues. Cyclized by cysteine disulfide bonds. |
| hriB$_{AG2}$ | c(dLdEGdRdRdSdLdEGdRdRdS) | (SEQ ID NO:41) | D-amino acid residues. Cyclized peptide bond. |

In Table I, above, the lowercase "c" is used to denote a cyclization by a peptide or amide bond joining the amino-terminal amino acid residue to the carboxy-terminal amino acid residue. Hence, the $hB_{AG1}$ polypeptide (SEQ ID NO:39) preferably comprises an amide bond joining the N-terminal serine residue to the C-terminal leucine residue. Similarly, the peptide $hriB_{AG2}$ (SEQ ID NO:41) preferably comprises an amid bond joining the N-terminal leucine residue to the C-terminal serine residue.

The lowercase "d" in front of an amino acid residue in Table I denotes that the residue is a D-amino acid residue (as opposed to an L-amino acid residue). Hence, the polypeptides $riB_{AG1}$ and $hriB_{AG2}$ preferably comprise D-amino acid residues. Indeed, all of the amino acid residues in these polypeptides (with the exception of the glycine residues, which are neither L nor D amino acid residues) are preferably D-amino acid residues.

It is readily apparent, upon visual inspection of the $riB_{AG1}$ and $hriB_{AG2}$ amino acid sequences (SEQ ID NOS:40 and 41), that these sequences are reverse sequences of the $B_{AG}$ polypeptide sequence (SEQ ID NO:17). In particular, and as will be appreciated by those of skill in the art, polypeptides of the invention which comprise a sequence of D-amino acid residues are expected to adopt three dimensional structures (i.e., "conformations") that are substantially similar or identical to the three dimensional conformation of a polypeptide comprising the reverse sequence of L-amino acid. Hence, in addition to the polypeptides of L-amino acid residues described supra, the present invention also contemplates polypeptides having the reverse sequence of D-amino acid residues. Hence, in one preferred embodiment peptides and peptidomimetics of the present invention comprise sequences of L-amino acid residues including the Arg-Gly-Glu (i.e., "RGE") motif described, supra. Accordingly, the invention also provides, in an alternative embodiment) peptides and peptidomimetics comprising sequences of D-amino acid residues including the short linear sequence motif dGlu-Gly-dArg (i.e., "dEGdR").

Peptides and peptidomimetics of the invention that comprise such D-amino acid residues are expected to be more stable and less readily degraded in vivo, e.g., by proteolytic enzymes. Similarly, cyclic amide bonds, such as those used in the $hB_{AG2}$ and $hriB_{AG2}$ polypeptides, are also expected to be less readily degraded in vivo. Shortened peptides (e.g., $hB_{AG}$, which lacks two terminal cysteines and two central alanines compared to $B_{AG}$) are more likely to cross the blood-brain barrier. Accordingly, such peptides may be preferred, e.g., for use in pharmaceutical compositions and administration to an individual.

7.8.2 Biological Activity

The $hB_{AG2}$, $riB_{AG1}$ and $hriB_{AG2}$ polypeptides were tested in a substrate based assay, to evaluate their ability to promote neurite outgrowth in an inhibitory environment. In particular, and as discussed above, the myelin associated glycoprotein (MAG) has been previously shown to inhibit neurite outgrowth response. See, for example, Mukhopadhyay et al., Neuron 1994, 13:757–767; and Tang et al., Mol. Cell. Neurosci. 1997, 9:333–346. As demonstrated in the examples, supra, Trk receptor agonists such as the $B_{AG}$ polypeptide are able to block MAG inhibitory activity, and promote neurite outgrowth in that inhibitory environment (i.e., in the presence of MAG). The data presented in the experiments described here, demonstrate that the $hB_{AG2}$, $riB_{AG1}$ and $hriB_{AG2}$ polypeptides also block MAG inhibitory activity and promote neurite outgrowth.

Materials and Methods.

Briefly, standard plastic 8 chamber tissue-culture slides were coated as follows with either: (a) polylysine; (b) polylysine and a mixture of goat anti-human IgG and fibronectin; or (c) polylysine, a mixture of goat anti-human IgG (Fc-specific) and fibronectin and MAG-Fc. First, slides are coated with polylysine at 17 μg/ml in distilled water ("dH$_2$O") for thirty (30) minutes at room temperature. After aspirating the wells, a mixture of anti-human IgG and/or fibronectin (both at 10 μg/ml in DMEM) is added to wells to be coated with those compounds, and incubated for 120 minutes. The wells are again aspirated and (for wells coated with MAG-Fc) incubated for sixty (60) minutes with MAG-Fc (0.25 μg/ml in DMEM and 10% FCS). PND2/3 rat cerebellar neurons are then added at 15K to each well in DMEM, 10% FCS, 25 mM KCl and 5 ng/ml FGF2, bringing the final media volume to 300 μl in each well. The cerebellar neurons are cultured for 27 hours before fixing and staining for GAP-43. Polylysine, goat anti-human IgG (Fc-specific) and fibronectin are available from SIGMA (St. Louis, Mo.).

Results. The mean length of the longest neurite per neuron was determined. Basal neurite growth of about 9 μm was observed on the polylysine substrate. Neurite growth increased to about 24 μm on the polylysine/fibronectin substrate. Neurite growth decreased to about 15 μm in the wells that had the additional MAG-Fc coating. FIG. 18A shows a dose response curve for the three peptidomimetics. Peptidomimetic $hriB_{AG2}$ (SEQ ID NO:40) promoted substantial dose-dependent neurite growth in the inhibitory environment. A neurite growth response can be observed at a dose of about 10 μg/ml and is almost double the value seen in the inhibitory environment without the peptidomimetic at a dose of 33 μg/ml (the highest concentration tested). $hB_{AG2}$ (SEQ ID NO:39) promotes neurite growth at a dose of 33 μg/ml. $riB_{AG1}$ (SEQ ID NO: 41) does not promote growth at the same concentration.

FIG. 18B shows a bar graph depicting neurite growth in the inhibitory environment in the presence of BDNF, $B_{AG}$, $hriB_{AG2}$, $hB_{AG2}$ or $riB_{AG}$. BDNF has no effect on neurite growth at concentrations of 10 μg/ml and 100 μg/ml. $B_{AG}$ peptide promotes neurite growth at concentrations of both 10 μg/ml and 100 μg/ml. $hriB_{AG2}$ at a concentration of 33 μg/ml promoted neurite growth to a substantially greater extent than BDNF, $B_{AG}$ peptide, and the $hB_{AG2}$ and $riB_{AG1}$ at any concentration. $hB_{AG2}$ at a concentration of 33 μg/ml promoted neurite growth to an extent comparable to $B_{AG}$ polypeptide at a concentration of 10 μg/ml.

These results show that other peptides and peptidomimetics, such as the $B_{AG}$ peptide derivatives of this application, can promote neurite growth in an inhibitory environment and to an extent that is comparable or even superior to that of the $B_{AG}$ polypeptide.

7.9. p75 Receptor Binding Agents Overcome Inhibition of Neuronal Growth

This example describes experiments investigating the effect of p75 receptor binding agents under conditions that normally inhibit neuronal growth. In particular, the experiments demonstrate that p75 receptor binding agents counteract the activity of inhibitory molecules and/or their receptors.

Neurite Outgrowth Assays

Co-cultures of cerebellar neurons on monolayers of either parental 3T3 cells or LK8 cells (an established transfected 3T3 cell line that expresses physiological levels of chick N-cadherin; see Doherty et al., *Neuron* 1991, 6:247–258) were established as previously described by Williams et al. (*Neuron* 1994, 13:583–594). The cells were maintained in Dulbecco's modified Eagle's medium supplemented with 10% fetal calf serum (FCS). These cerebellar neurons express the TrkB receptor and do not express functional levels of the TrkA receptor.

For establishment of the co-cultures, about 80,000 3T3 cells (or LK8 cells) were plated into individual chambers of an eight-chamber tissue culture slide coated with poly-L-lysine and fibronectin. The plated cells were maintained overnight in Dulbecco's modified Eagle's medium ("DMEM") supplemented with 10% FCS to allow for the formation of confluent monolayers. The medium was removed and about 6,000 dissociated cerebellar neurons (taken from post-natal day 2/3 rats) were plated into each well in SATO medium supplemented with 2% FCS. Test reagents were added as indicated in the text and the co-cultures maintained for 23 hours. The co-cultures were then fixed and stained for GAP-43 immunoreactivity. The mean length of the longest neurite per cell was measured for between about 120 and 150 neurons, again as previously described by Williams et al. (*Neuron* 1994, 13:583–594).

Reagents

Recombined human NGF and BDNF were obtained from R&D systems (Minneapolis, Minn.). Synthetic peptides were all obtained from a commercial supplier (Multiple Peptide Systems, San Diego, Calif.). All peptides were purified by reverse-phase high performance liquid chromatography (RP-HPLC) according to routine methods, and obtained at the highest level of purity (i.e., greater than 95% pure).

The p75 receptor binding agents promote neurotrophin-mediated neuron growth in an inhibitory environment. Myelin associated glycoprotein (MAG) has been previously shown to inhibit neurite outgrowth response from post-natal day 2–3 rat cerebellar neurons when presented to those cells as either a transfected molecule in the cellular substrate (Mukhopadhyay et al., *Neuron* 1994, 13:757–767) or when added as a soluble Fc chimeric protein (Tang et al., *Mol. Cell. Neurosci.* 1997, 9:333–346). In furtherance of those studies, post-natal day 3 cerebellar neurons were cultured over monolayers of LK8 cells, a 3T3 fibroblast cell line that express transfected N-cadherin and have been previously shown to promote a robust neurite outgrowth response (Williams et al., *Neuron* 1994, 13:583–594). Cells were cultured with soluble MAG-Fc fusion protein present in the culture medium at concentrations of 0, 5 or 25 µg/ml. As expected, MAG-Fc inhibited neurite outgrowth in a dose-dependent manner, with an approximately 40% inhibition response when present in the culture medium at a concentration of 25 µg/ml. Thus, this culture medium, containing soluble MAG-Fc fusion protein, is an inhibitory culture medium.

The inhibitory culture medium was further supplemented with BDNF at 1 ng/ml, NGF at 10 ng/ml or 100 ng/ml, BDNF (at 1 ng/ml) in combination with NGF (at 10 ng/ml or 100 ng/ml), a constrained monomer of the loop 1 motif in NGF which binds to the p75 receptor (N-Ac-CTDIKGKEC-NH$_2$ (SEQ ID NO:43)) at 100 µg/ml, or the NGF loop 1 peptide (at 100 µg/ml) in combination with BDNF (at 1 ng/ml). The growth media containing MAG-Fc alone was the control. When the neurotrophin BDNF was present in the inhibitory culture medium at a concentration of 1 ng/ml there was no measurable effect on the MAG response—i.e., MAG-Fc continued to inhibit neurite outgrowth. Like BDNF, NGF at concentrations of either 10 ng/ml or 100 ng/ml did not stimulate neurite outgrowth in the presence of MAG-Fc (FIG. 19). In data from individual experiments, the results obtained with NGF at 10 ng/ml and 100 ng/ml were not obviously different, and these data were therefore pooled. These results are consistent with previous reports that neuron cells must be "primed" with neurotrophins to circumvent the inhibitor activity of MAG and myelin (see, Cai et al., *Neuron* 1999, 22:89–101).

The constrained monomer of the NGF loop 1 binding motif alone also had no effect on neurite outgrowth in the presence of MAG-Fc (FIG. 19). However, the NGF loop 1 peptide in combination with BDNF produced a significant neurite outgrowth response. Additionally, a significant neurite outgrowth response was also observed when BDNF and NGF were added together (FIG. 19) in a ratio of 1:10 or 1:100 (BDNF to NGF).

The results from these experiments suggest that, when NGF and BDNF are administered to an inhibitory environment, NGF allows BDNF to promote neurite outgrowth. The results additionally show that administration of a constrained monomer of the first β hairpin loop in NGF allows BDNF to promote CNS neuron growth in an inhibitory environment.

7.10. Treatment of a Patient with Spinal Cord Injury

A patient is diagnosed with a thoracic spinal cord injury and has loss of sensation and motor activity in his legs. The patient undergoes surgery to stabilize the thoracic spine. Following debridement of soft tissue and bone, the damaged spinal cord is exposed. A sterile pharmaceutical powder comprising a p75 receptor binding agent is mixed with sterile normal saline to form a gel. The surgeon topically applies the p75 receptor binding agent gel to the exposed surface of the cord. The stabilization procedure is completed in the usual fashion. Post-operatively, the patient is monitored for improvement in sensation and/or motor activity in the lower extremities.

8. REFERENCES CITED

Numerous references, including patents, patent applications and various publications, are cited and discussed in the description of this invention. The citation and/or discussion of such references is provided merely to clarify the description of the present invention and is not an admission that any such reference is "prior art" to the invention described here. All references cited and/or discussed in this specification (including references, e.g., to biological sequences or structures in the GenBank, PDB or other public databases) are incorporated herein by reference in their entirety and to the same extent as if each reference was individually incorporated by reference.

What is claimed is:

1. A cyclic peptide consisting of the formula,

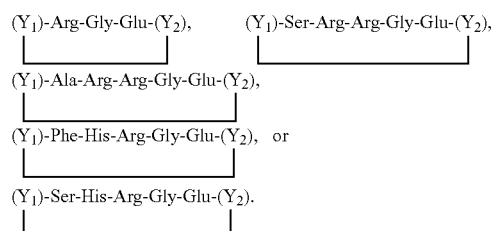

wherein $Y_1$ and $Y_2$ are independently selected amino acids with a covalent bond formed between $Y_1$ and $Y_2$, wherein the cyclic peptide is monocyclic Trk (tyrosine kinase) receptor mediated activity, and wherein the cyclic peptide is monocyclic.

2. A cyclic peptide consisting of the amino acid sequence:
Cys-Arg-Gly-Glu-Cys (SEQ ID NO:9);
Cys-Ser-Arg-Arg-Gly-Glu-Cys (SEQ ID NO:1);
Cys-Ala-Arg-Arg-Gly-Glu-Cys (SEQ ID NO:3);
Cys-Phe-His-Arg-Gly-Glu-Cys (SEQ ID NO:5); or
Cys-Ser-His-Arg-Gly-Glu-Cys (SEQ ID NO:7);
wherein a covalent bond joins the N-terminal and C-terminal cysteines in said amino acid sequence, wherein the cyclic peptide modulates Trk (tyrosine kinase) receptor mediated activity, and wherein the cyclic peptide is monocyclic.

3. A cyclic peptide according claim 1 wherein $Y_1$ and $Y_2$ are covalently linked by disulfide bonds.

4. A composition comprising:
(a) an amount of a cyclic peptide according to claim 1, which amount is effective for modulating a Trk receptor mediated activity; and
(b) one or more carriers, diluents or excipients.

5. A composition according to claim 4, wherein the cyclic peptide inhibits a Trk receptor mediated activity.

6. A cyclic peptide wherein the cyclic peptide consisting of the formula

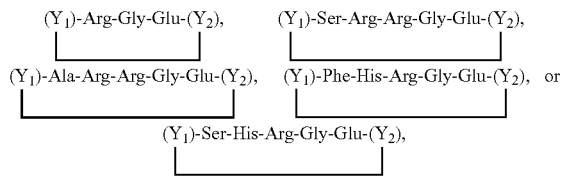

wherein $Y_1$ and $Y_2$ are independently selected amino acids with a covalent bond formed between $Y_1$ and $Y_2$, and wherein the cyclic peptide is monocyclic.

7. A cyclic peptide consisting of the amino acid sequence:
Cys-Arg-Gly-Glu-Cys (SEQ ID NO:9);
Cys-Ser-Arg-Arg-Gly-Glu-Cys (SEQ ID NO:1);
Cys-Ala-Arg-Arg-Gly-Glu-Cys (SEQ ID NO:3);
Cys-Phe-His-Arg-Gly-Glu-Cys (SEQ ID NO:5); or
Cys-Ser-His-Arg-Gly-Glu-Cys (SEQ ID NO:7);
wherein a covalent bond joins the N-terminal and C-terminal cysteines in said amino acid sequence and wherein the cyclic peptide is monocyclic.

8. A composition comprising:
(a) an effective amount of a cyclic peptide, according to claim 6; and
(b) one or more carriers, diluents or excipients.

9. A composition comprising:
(a) an effective amount of a cyclic peptide, according to claim 7; and
(b) one or more carriers, diluents or excipients.

* * * * *

SEQUENCE LISTING

<160> NUMBER OF SEQ ID NOS: 43

<210> SEQ ID NO 1
<211> LENGTH: 7
<212> TYPE: PRT
<213> ORGANISM: Artificial
<220> FEATURE:
<223> OTHER INFORMATION: synthetic peptide

<400> SEQUENCE: 1

Cys Ser Arg Arg Gly Glu Cys
1               5

<210> SEQ ID NO 2
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (7)..(7)
<223> OTHER INFORMATION: Xaa is C-NH2

<400> SEQUENCE: 2

Xaa Ser Arg Arg Gly Glu Xaa
1               5

<210> SEQ ID NO 3
<211> LENGTH: 7
<212> TYPE: PRT
<213> ORGANISM: Artificial
<220> FEATURE:
<223> OTHER INFORMATION: synthetic peptide

<400> SEQUENCE: 3

Cys Ala Arg Arg Gly Glu Cys
1               5

<210> SEQ ID NO 4
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (7)..(7)
<223> OTHER INFORMATION: Xaa is C-NH2

<400> SEQUENCE: 4

Xaa Ala Arg Arg Gly Glu Xaa
1               5

<210> SEQ ID NO 5
<211> LENGTH: 7
<212> TYPE: PRT
<213> ORGANISM: artificial
<220> FEATURE:
<223> OTHER INFORMATION: synthetic peptide

```
<400> SEQUENCE: 5

Cys Phe His Arg Gly Glu Cys
1               5

<210> SEQ ID NO 6
<211> LENGTH: 7
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (7)..(7)
<223> OTHER INFORMATION: Xaa is C-NH2

<400> SEQUENCE: 6

Xaa Phe His Arg Gly Glu Xaa
1               5

<210> SEQ ID NO 7
<211> LENGTH: 7
<212> TYPE: PRT
<213> ORGANISM: artificial
<220> FEATURE:
<223> OTHER INFORMATION: synthetic peptide

<400> SEQUENCE: 7

Cys Ser His Arg Gly Glu Cys
1               5

<210> SEQ ID NO 8
<211> LENGTH: 6
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (6)..(6)
<223> OTHER INFORMATION: Xaa is E-NH2

<400> SEQUENCE: 8

Xaa Phe His Arg Gly Xaa
1               5

<210> SEQ ID NO 9
<211> LENGTH: 5
<212> TYPE: PRT
<213> ORGANISM: artificial
<220> FEATURE:
<223> OTHER INFORMATION: synthetic peptide

<400> SEQUENCE: 9

Cys Arg Gly Glu Cys
1               5

<210> SEQ ID NO 10
<211> LENGTH: 5
<212> TYPE: PRT
<213> ORGANISM: artificial
```

```
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-AC-C
<220> FEATURE:
<221> NAME/KEY: MISC_FEATURE
<222> LOCATION: (5)..(5)
<223> OTHER INFORMATION: Xaa is C-NH2

<400> SEQUENCE: 10

Xaa Arg Gly Glu Xaa
1               5

<210> SEQ ID NO 11
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-K
<220> FEATURE:
<221> NAME/KEY: MISC_FEATURE
<222> LOCATION: (5)..(5)
<223> OTHER INFORMATION: Xaa is D-NH2

<400> SEQUENCE: 11

Xaa Arg Gly Glu Xaa
1               5

<210> SEQ ID NO 12
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is C(O)-C
<220> FEATURE:
<221> NAME/KEY: MISC_FEATURE
<222> LOCATION: (5)..(5)
<223> OTHER INFORMATION: Xaa is C-NH2

<400> SEQUENCE: 12

Xaa Arg Gly Glu Xaa
1               5

<210> SEQ ID NO 13
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is CH3-SO2-NH-C
<220> FEATURE:
<221> NAME/KEY: MISC_FEATURE
<222> LOCATION: (5)..(5)
<223> OTHER INFORMATION: Xaa is C-NH2

<400> SEQUENCE: 13

Xaa Arg Gly Glu Xaa
1               5
```

```
<210> SEQ ID NO 14
<211> LENGTH: 6
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (6)..(6)
<223> OTHER INFORMATION: Xaa is Y-NH2

<400> SEQUENCE: 14

Xaa Arg Gly Glu Cys Xaa
1               5

<210> SEQ ID NO 15
<211> LENGTH: 6
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is H-C(O)-C
<220> FEATURE:
<221> NAME/KEY: MISC_FEATURE
<222> LOCATION: (6)..(6)
<223> OTHER INFORMATION: Xaa is Y-NH2

<400> SEQUENCE: 15

Xaa Arg Gly Glu Cys Xaa
1               5

<210> SEQ ID NO 16
<211> LENGTH: 6
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is CH3-SO2-NH-C
<220> FEATURE:
<221> NAME/KEY: MISC_FEATURE
<222> LOCATION: (6)..(6)
<223> OTHER INFORMATION: Xaa is Y-NH2

<400> SEQUENCE: 16

Xaa Arg Gly Glu Cys Xaa
1               5

<210> SEQ ID NO 17
<211> LENGTH: 16
<212> TYPE: PRT
<213> ORGANISM: artificial
<220> FEATURE:
<223> OTHER INFORMATION: synthetic peptide

<400> SEQUENCE: 17

Cys Ser Arg Arg Gly Glu Leu Ala Ala Ser Arg Arg Gly Glu Leu Cys
1               5                   10                  15
```

```
<210> SEQ ID NO 18
<211> LENGTH: 16
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (16)..(16)
<223> OTHER INFORMATION: Xaa is C-NH2

<400> SEQUENCE: 18

Xaa Ser Arg Arg Gly Glu Leu Ala Ala Ser Arg Arg Gly Glu Leu Xaa
1               5                   10                  15

<210> SEQ ID NO 19
<211> LENGTH: 229
<212> TYPE: PRT
<213> ORGANISM: Homo sapiens

<400> SEQUENCE: 19

Ala Pro Met Lys Glu Ala Asn Ile Arg Gly Gln Gly Leu Ala Tyr
1               5                   10                  15

Pro Gly Val Arg Thr His Gly Thr Leu Glu Ser Val Asn Gly Pro Lys
                20                  25                  30

Ala Gly Ser Arg Gly Leu Thr Ser Leu Ala Asp Thr Phe Glu His Val
            35                  40                  45

Ile Glu Glu Leu Leu Asp Glu Asp Gln Lys Val Arg Pro Asn Glu Glu
50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
210                 215                 220

Ile Lys Arg Gly Arg
225

<210> SEQ ID NO 20
<211> LENGTH: 186
<212> TYPE: PRT
<213> ORGANISM: Homo sapiens
```

-continued

```
<400> SEQUENCE: 20

Gln Pro Pro Pro Ser Thr Leu Pro Pro Phe Leu Ala Pro Glu Trp Asp
1               5                   10                  15

Leu Leu Ser Pro Arg Val Val Leu Ser Arg Gly Ala Pro Ala Gly Pro
            20                  25                  30

Pro Leu Leu Phe Leu Leu Glu Ala Gly Ala Phe Arg Glu Ser Ala Gly
        35                  40                  45

Ala Pro Ala Asn Arg Ser Arg Arg Gly Val Ser Glu Thr Ala Pro Ala
    50                  55                  60

Ser Arg Arg Gly Glu Leu Ala Val Cys Asp Ala Val Ser Gly Trp Val
65                  70                  75                  80

Thr Asp Arg Arg Thr Ala Val Asp Leu Arg Gly Arg Glu Val Glu Val
                85                  90                  95

Leu Gly Glu Val Pro Ala Ala Gly Gly Ser Pro Leu Arg Gln Tyr Phe
            100                 105                 110

Phe Glu Thr Arg Cys Lys Ala Asp Asn Ala Glu Gly Gly Pro Gly Gly
        115                 120                 125

Ala Gly Gly Gly Cys Arg Gly Val Asp Arg Arg His Trp Val Ser
    130                 135                 140

Glu Cys Lys Ala Lys Gln Ser Tyr Val Arg Ala Leu Thr Ala Asp Ala
145                 150                 155                 160

Gln Gly Arg Val Gly Trp Arg Trp Ile Arg Ile Asp Thr Ala Cys Val
                165                 170                 175

Cys Thr Leu Leu Ser Arg Thr Gly Arg Ala
            180                 185

<210> SEQ ID NO 21
<211> LENGTH: 241
<212> TYPE: PRT
<213> ORGANISM: Homo sapiens

<400> SEQUENCE: 21

Gln Gly Asn Asn Met Asp Gln Arg Ser Leu Pro Glu Asp Ser Leu Asn
1               5                   10                  15

Ser Leu Ile Ile Lys Leu Ile Gln Ala Asp Ile Leu Lys Asn Lys Leu
            20                  25                  30

Ser Lys Gln Met Val Asp Val Lys Glu Asn Tyr Gln Ser Thr Leu Pro
        35                  40                  45

Lys Ala Glu Ala Pro Arg Glu Pro Glu Arg Gly Gly Pro Ala Lys Ser
    50                  55                  60

Ala Phe Gln Pro Val Ile Ala Met Asp Thr Glu Leu Leu Arg Gln Gln
65                  70                  75                  80

Arg Arg Tyr Asn Ser Pro Arg Val Leu Leu Ser Asp Ser Thr Pro Leu
                85                  90                  95

Glu Pro Pro Pro Leu Tyr Leu Met Glu Asp Tyr Val Gly Ser Pro Val
            100                 105                 110

Val Ala Asn Arg Thr Ser Arg Arg Lys Arg Tyr Ala Glu His Lys Ser
        115                 120                 125

His Arg Gly Glu Tyr Ser Val Cys Asp Ser Glu Ser Leu Trp Val Thr
    130                 135                 140

Asp Lys Ser Ser Ala Ile Asp Ile Arg Gly His Gln Val Thr Val Leu
145                 150                 155                 160

Gly Glu Ile Lys Thr Gly Asn Ser Pro Val Lys Gln Tyr Phe Tyr Glu
                165                 170                 175
```

```
Thr Arg Cys Lys Glu Ala Arg Pro Val Lys Asn Gly Cys Arg Gly Ile
            180                 185                 190

Asp Asp Lys His Trp Asn Ser Gln Cys Lys Thr Ser Gln Thr Tyr Val
        195                 200                 205

Arg Ala Leu Thr Ser Glu Asn Asn Lys Leu Val Gly Trp Arg Trp Ile
        210                 215                 220

Arg Ile Asp Thr Ser Cys Val Cys Ala Leu Ser Arg Lys Ile Gly Arg
225                 230                 235                 240

Thr

<210> SEQ ID NO 22
<211> LENGTH: 223
<212> TYPE: PRT
<213> ORGANISM: Homo sapiens

<400> SEQUENCE: 22

Glu Pro His Ser Glu Ser Asn Val Pro Ala Gly His Thr Ile Pro Gln
1               5                   10                  15

Val His Trp Thr Lys Leu Gln His Ser Leu Asp Thr Ala Leu Arg Arg
            20                  25                  30

Ala Arg Ser Ala Pro Ala Ala Ala Ile Ala Ala Arg Val Ala Gly Gln
        35                  40                  45

Thr Arg Asn Ile Thr Val Asp Pro Arg Leu Phe Lys Lys Arg Arg Leu
    50                  55                  60

Arg Ser Pro Arg Val Leu Phe Ser Thr Gln Pro Pro Arg Glu Ala Ala
65                  70                  75                  80

Asp Thr Gln Asp Leu Asp Phe Glu Val Gly Gly Ala Ala Pro Phe Asn
                85                  90                  95

Arg Thr His Arg Ser Lys Arg Ser Ser His Pro Ile Phe His Arg
            100                 105                 110

Gly Glu Phe Ser Val Cys Asp Ser Val Ser Val Trp Val Gly Asp Lys
        115                 120                 125

Thr Thr Ala Thr Asp Ile Lys Gly Lys Glu Val Met Val Leu Gly Glu
    130                 135                 140

Val Asn Ile Asn Asn Ser Val Phe Lys Gln Tyr Phe Phe Glu Thr Lys
145                 150                 155                 160

Cys Arg Asp Pro Asn Pro Val Asp Ser Gly Cys Arg Gly Ile Asp Ser
                165                 170                 175

Lys His Trp Asn Ser Tyr Cys Thr Thr Thr His Thr Phe Val Lys Ala
            180                 185                 190

Leu Thr Met Asp Gly Lys Gln Ala Ala Trp Arg Phe Ile Arg Ile Asp
        195                 200                 205

Thr Ala Cys Val Cys Val Leu Ser Arg Lys Ala Val Arg Arg Ala
    210                 215                 220

<210> SEQ ID NO 23
<211> LENGTH: 790
<212> TYPE: PRT
<213> ORGANISM: Homo sapiens

<400> SEQUENCE: 23

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30
```

-continued

```
Ala Ala Pro Cys Pro Asp Ala Cys Cys Pro His Gly Ser Ser Gly Leu
        35                  40                  45
Arg Cys Thr Arg Asp Gly Ala Leu Asp Ser Leu His His Leu Pro Gly
    50                  55                  60
Ala Glu Asn Leu Thr Glu Leu Tyr Ile Glu Asn Gln Gln His Leu Gln
65                  70                  75                  80
His Leu Glu Leu Arg Asp Leu Arg Gly Leu Gly Glu Leu Arg Asn Leu
                85                  90                  95
Thr Ile Val Lys Ser Gly Leu Arg Phe Val Ala Pro Asp Ala Phe His
            100                 105                 110
Phe Thr Pro Arg Leu Ser Arg Leu Asn Leu Ser Phe Asn Ala Leu Glu
        115                 120                 125
Ser Leu Ser Trp Lys Thr Val Gln Gly Leu Ser Leu Gln Glu Leu Val
    130                 135                 140
Leu Ser Gly Asn Pro Leu His Cys Ser Cys Ala Leu Arg Trp Leu Gln
145                 150                 155                 160
Arg Trp Glu Glu Glu Gly Leu Gly Gly Val Pro Glu Gln Lys Leu Gln
                165                 170                 175
Cys His Gly Gln Gly Pro Leu Ala His Met Pro Asn Ala Ser Cys Gly
            180                 185                 190
Val Pro Thr Leu Lys Val Gln Val Pro Asn Ala Ser Val Asp Val Gly
        195                 200                 205
Asp Asp Val Leu Leu Arg Cys Gln Val Glu Gly Arg Gly Leu Glu Gln
    210                 215                 220
Ala Gly Trp Ile Leu Thr Glu Leu Glu Gln Ser Ala Thr Val Met Lys
225                 230                 235                 240
Ser Gly Gly Leu Pro Ser Leu Gly Leu Thr Leu Ala Asn Val Thr Ser
                245                 250                 255
Asp Leu Asn Arg Lys Asn Leu Thr Cys Trp Ala Glu Asn Asp Val Gly
            260                 265                 270
Arg Ala Glu Val Ser Val Gln Val Asn Val Ser Phe Pro Ala Ser Val
        275                 280                 285
Gln Leu His Thr Ala Val Glu Met His His Trp Cys Ile Pro Phe Ser
    290                 295                 300
Val Asp Gly Gln Pro Ala Pro Ser Leu Arg Trp Leu Phe Asn Gly Ser
305                 310                 315                 320
Val Leu Asn Glu Thr Ser Phe Ile Phe Thr Glu Phe Leu Glu Pro Ala
                325                 330                 335
Ala Asn Glu Thr Val Arg His Gly Cys Leu Arg Leu Asn Gln Pro Thr
            340                 345                 350
His Val Asn Asn Gly Asn Val Thr Leu Leu Ala Ala Asn Pro Phe Gly
        355                 360                 365
Gln Ala Ser Ala Ser Ile Met Ala Ala Phe Met Asp Asn Pro Phe Glu
    370                 375                 380
Phe Asn Pro Glu Asp Pro Ile Pro Asp Thr Asn Ser Thr Ser Gly Asp
385                 390                 395                 400
Pro Val Glu Lys Lys Asp Glu Thr Pro Phe Gly Val Ser Val Ala Val
                405                 410                 415
Gly Leu Ala Val Phe Ala Cys Leu Phe Leu Ser Thr Leu Leu Leu Val
            420                 425                 430
Leu Asn Lys Cys Gly Arg Arg Asn Lys Phe Gly Ile Asn Arg Pro Ala
        435                 440                 445
```

```
Val Leu Ala Pro Glu Asp Gly Leu Ala Met Ser Leu His Phe Met Thr
    450                 455                 460

Leu Gly Gly Ser Ser Leu Ser Pro Thr Glu Gly Lys Gly Ser Gly Leu
465                 470                 475                 480

Gln Gly His Ile Ile Glu Asn Pro Gln Tyr Arg Ser Asp Ala Cys Val
                485                 490                 495

His His Ile Lys Arg Arg Asp Ile Val Leu Lys Trp Glu Leu Gly Glu
            500                 505                 510

Gly Ala Phe Gly Lys Val Phe Leu Ala Glu Cys His Asn Leu Leu Pro
        515                 520                 525

Glu Gln Asp Lys Met Leu Val Ala Val Lys Ala Leu Lys Glu Ala Ser
    530                 535                 540

Glu Ser Ala Arg Gln Asp Phe Gln Arg Glu Ala Glu Leu Leu Thr Met
545                 550                 555                 560

Leu Gln His Gln His Ile Val Arg Phe Phe Gly Val Cys Thr Glu Gly
                565                 570                 575

Arg Pro Leu Leu Met Val Phe Glu Tyr Met Arg His Gly Asp Leu Asn
            580                 585                 590

Arg Phe Leu Arg Ser His Gly Pro Asp Ala Lys Leu Leu Ala Gly Gly
        595                 600                 605

Glu Asp Val Ala Pro Gly Pro Leu Gly Leu Gly Gln Leu Leu Ala Val
    610                 615                 620

Ala Ser Gln Val Ala Ala Gly Met Val Tyr Leu Ala Gly Leu His Phe
625                 630                 635                 640

Val His Arg Asp Leu Ala Thr Arg Asn Cys Leu Val Gly Gln Gly Leu
                645                 650                 655

Val Val Lys Ile Gly Asp Phe Gly Met Ser Arg Asp Ile Tyr Ser Thr
            660                 665                 670

Asp Tyr Tyr Arg Tyr Gly Gly Arg Thr Met Leu Pro Ile Arg Trp Met
        675                 680                 685

Pro Pro Glu Ser Ile Leu Tyr Arg Lys Phe Thr Thr Glu Ser Asp Val
    690                 695                 700

Trp Ser Phe Gly Val Val Leu Trp Glu Ile Phe Thr Tyr Gly Lys Gln
705                 710                 715                 720

Pro Trp Tyr Gln Leu Ser Asn Thr Glu Ala Ile Asp Cys Ile Thr Gln
                725                 730                 735

Gly Arg Glu Leu Glu Arg Pro Arg Ala Cys Pro Pro Glu Val Tyr Ala
            740                 745                 750

Ile Met Arg Gly Cys Trp Gln Arg Glu Pro Gln Gln Arg His Ser Ile
        755                 760                 765

Lys Asp Val His Ala Arg Leu Gln Ala Leu Ala Gln Ala Pro Pro Val
    770                 775                 780

Tyr Leu Asp Val Leu Gly
785                 790

<210> SEQ ID NO 24
<211> LENGTH: 822
<212> TYPE: PRT
<213> ORGANISM: Homo sapiens

<400> SEQUENCE: 24

Met Ser Ser Trp Ile Arg Trp His Gly Pro Ala Met Ala Pro Leu Trp
1               5                   10                  15

Gly Phe Cys Trp Leu Val Val Gly Phe Trp Arg Ala Ala Phe Ala Cys
            20                  25                  30
```

-continued

```
Pro Thr Ser Cys Lys Cys Ser Ala Ser Arg Ile Trp Cys Ser Asp Pro
        35                  40                  45

Ser Pro Gly Ile Val Ala Phe Pro Arg Leu Glu Pro Asn Ser Val Asp
    50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
        115                 120                 125

Ser Leu Ser Arg Lys His Phe Arg His Leu Asp Leu Ser Glu Leu Ile
    130                 135                 140

Leu Val Gly Asn Pro Phe Thr Cys Ser Cys Asp Ile Met Trp Ile Lys
145                 150                 155                 160

Thr Leu Gln Glu Ala Lys Ser Ser Pro Asp Thr Gln Asp Leu Tyr Cys
                165                 170                 175

Leu Asn Glu Ser Ser Lys Asn Ile Pro Leu Ala Asn Leu Gln Ile Pro
            180                 185                 190

Asn Cys Gly Leu Pro Ser Ala Asn Leu Ala Ala Pro Asn Leu Thr Val
        195                 200                 205

Glu Glu Gly Lys Ser Ile Thr Leu Ser Cys Ser Val Ala Gly Asp Pro
    210                 215                 220

Val Pro Asn Met Tyr Trp Asp Val Gly Asn Leu Val Ser Lys His Met
225                 230                 235                 240

Asn Glu Thr Ser His Thr Gln Gly Ser Leu Arg Ile Thr Asn Ile Ser
                245                 250                 255

Ser Asp Asp Ser Gly Lys Gln Ile Ser Cys Val Ala Glu Asn Leu Val
            260                 265                 270

Gly Glu Asp Gln Asp Ser Val Asn Leu Thr Val His Phe Ala Pro Thr
        275                 280                 285

Ile Thr Phe Leu Glu Ser Pro Thr Ser Asp His His Trp Cys Ile Pro
    290                 295                 300

Phe Thr Val Lys Gly Asn Pro Lys Pro Ala Leu Gln Trp Phe Tyr Asn
305                 310                 315                 320

Gly Ala Ile Leu Asn Glu Ser Lys Tyr Ile Cys Thr Lys Ile His Val
                325                 330                 335

Thr Asn His Thr Glu Tyr His Gly Cys Leu Gln Leu Asp Asn Pro Thr
            340                 345                 350

His Met Asn Asn Gly Asp Tyr Thr Leu Ile Ala Lys Asn Glu Tyr Gly
        355                 360                 365

Lys Asp Glu Lys Gln Ile Ser Ala His Phe Met Gly Trp Pro Gly Ile
    370                 375                 380

Asp Asp Gly Ala Asn Pro Asn Tyr Pro Asp Val Ile Tyr Glu Asp Tyr
385                 390                 395                 400

Gly Thr Ala Ala Asn Asp Ile Gly Asp Thr Thr Asn Arg Ser Asn Glu
                405                 410                 415

Ile Pro Ser Thr Asp Val Thr Asp Lys Thr Gly Arg Glu His Leu Ser
            420                 425                 430

Val Tyr Ala Val Val Val Ile Ala Ser Val Val Gly Phe Cys Leu Leu
        435                 440                 445
```

```
Val Met Leu Phe Leu Leu Lys Leu Ala Arg His Ser Lys Phe Gly Met
    450                 455                 460

Lys Gly Pro Ala Ser Val Ile Ser Asn Asp Asp Ser Ala Ser Pro
465                 470                 475                 480

Leu His His Ile Ser Asn Gly Ser Asn Thr Pro Ser Ser Glu Gly
                485                 490                 495

Gly Pro Asp Ala Val Ile Ile Gly Met Thr Lys Ile Pro Val Ile Glu
            500                 505                 510

Asn Pro Gln Tyr Phe Gly Ile Thr Asn Ser Gln Leu Lys Pro Asp Thr
                515                 520                 525

Phe Val Gln His Ile Lys Arg His Asn Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
                580                 585                 590

Thr Asn Leu Gln His Glu His Ile Val Lys Phe Tyr Gly Val Cys Val
                595                 600                 605

Glu Gly Asp Pro Leu Ile Met Val Phe Glu Tyr Met Lys His Gly Asp
610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
                660                 665                 670

Val His Arg Asp Leu Ala Thr Arg Asn Cys Leu Val Gly Glu Asn Leu
    675                 680                 685

Leu Val Lys Ile Gly Asp Phe Gly Met Ser Arg Asp Val Tyr Ser Thr
690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
                740                 745                 750

Pro Trp Tyr Gln Leu Ser Asn Asn Glu Val Ile Glu Cys Ile Thr Gln
                755                 760                 765

Gly Arg Val Leu Gln Arg Pro Arg Thr Cys Pro Gln Glu Val Tyr Glu
                770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 25
<211> LENGTH: 839
<212> TYPE: PRT
<213> ORGANISM: Homo sapiens
```

<400> SEQUENCE: 25

```
Met Asp Val Ser Leu Cys Pro Ala Lys Cys Ser Phe Trp Arg Ile Phe
1               5                   10                  15
Leu Leu Gly Ser Val Trp Leu Asp Tyr Val Gly Ser Val Leu Ala Cys
            20                  25                  30
Pro Ala Asn Cys Val Cys Ser Lys Thr Glu Ile Asn Cys Arg Arg Pro
        35                  40                  45
Asp Asp Gly Asn Leu Phe Pro Leu Leu Glu Gly Gln Asp Ser Gly Asn
    50                  55                  60
Ser Asn Gly Asn Ala Asn Ile Asn Ile Thr Asp Ile Ser Arg Asn Ile
65                  70                  75                  80
Thr Ser Ile His Ile Glu Asn Trp Arg Ser Leu His Thr Leu Asn Ala
                85                  90                  95
Val Asp Met Glu Leu Tyr Thr Gly Leu Gln Lys Leu Thr Ile Lys Asn
            100                 105                 110
Ser Gly Leu Arg Ser Ile Gln Pro Arg Ala Phe Ala Lys Asn Pro His
        115                 120                 125
Leu Arg Tyr Ile Asn Leu Ser Ser Asn Arg Leu Thr Thr Leu Ser Trp
    130                 135                 140
Gln Leu Phe Gln Thr Leu Ser Leu Arg Glu Leu Gln Leu Glu Gln Asn
145                 150                 155                 160
Phe Phe Asn Cys Ser Cys Asp Ile Arg Trp Met Gln Leu Trp Gln Glu
                165                 170                 175
Gln Gly Glu Ala Lys Leu Asn Ser Gln Asn Leu Tyr Cys Ile Asn Ala
            180                 185                 190
Asp Gly Ser Gln Leu Pro Leu Phe Arg Met Asn Ile Ser Gln Cys Asp
        195                 200                 205
Leu Pro Glu Ile Ser Val Ser His Val Asn Leu Thr Val Arg Glu Gly
    210                 215                 220
Asp Asn Ala Val Ile Thr Cys Asn Gly Ser Gly Ser Pro Leu Pro Asp
225                 230                 235                 240
Val Asp Trp Ile Val Thr Gly Leu Gln Ser Ile Asn Thr His Gln Thr
                245                 250                 255
Asn Leu Asn Trp Thr Asn Val His Ala Ile Asn Leu Thr Leu Val Asn
            260                 265                 270
Val Thr Ser Glu Asp Asn Gly Phe Thr Leu Thr Cys Ile Ala Glu Asn
        275                 280                 285
Val Val Gly Met Ser Asn Ala Ser Val Ala Leu Thr Val Tyr Tyr Pro
    290                 295                 300
Pro Arg Val Val Ser Leu Glu Glu Pro Glu Leu Arg Leu Glu His Cys
305                 310                 315                 320
Ile Glu Phe Val Val Arg Gly Asn Pro Pro Thr Leu His Trp Leu
                325                 330                 335
His Asn Gly Gln Pro Leu Arg Glu Ser Lys Ile Ile His Val Glu Tyr
            340                 345                 350
Tyr Gln Glu Gly Glu Ile Ser Glu Gly Cys Leu Leu Phe Asn Lys Pro
        355                 360                 365
Thr His Tyr Asn Asn Gly Asn Tyr Arg Leu Ile Ala Lys Asn Pro Leu
    370                 375                 380
Gly Thr Ala Asn Gln Thr Ile Asn Gly His Phe Leu Lys Glu Pro Phe
385                 390                 395                 400
Pro Glu Ser Thr Asp Asn Phe Ile Leu Phe Asp Glu Val Ser Pro Thr
                405                 410                 415
```

-continued

```
Pro Pro Ile Thr Val Thr His Lys Pro Glu Glu Asp Thr Phe Gly Val
        420                 425                 430

Ser Ile Ala Val Gly Leu Ala Ala Phe Ala Cys Val Leu Leu Val Val
        435                 440                 445

Leu Phe Val Met Ile Asn Lys Tyr Gly Arg Arg Ser Lys Phe Gly Met
    450                 455                 460

Lys Gly Pro Val Ala Val Ile Ser Gly Glu Asp Ser Ala Ser Pro
465                 470                 475                 480

Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
            515                 520                 525

Tyr Val Gln His Ile Lys Arg Arg Asp Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
            595                 600                 605

Asp Gly Asp Pro Leu Ile Met Val Phe Glu Tyr Met Lys His Gly Asp
            610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
            675                 680                 685

Ala Asn Leu Leu Val Lys Ile Gly Asp Phe Gly Met Ser Arg Asp Val
690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
                725                 730                 735

Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
            755                 760                 765

Gln Pro Trp Phe Gln Leu Ser Asn Thr Glu Val Ile Glu Cys Ile Thr
            770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
                805                 810                 815
```

Ile Lys Glu Ile Tyr Lys Ile Leu His Ala Leu Gly Lys Ala Thr Pro
            820                 825                 830

Ile Tyr Leu Asp Ile Leu Gly
        835

<210> SEQ ID NO 26
<211> LENGTH: 7
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (7)..(7)
<223> OTHER INFORMATION: Xaa is C-NH2

<400> SEQUENCE: 26

Xaa Ser Arg Arg Gly Glu Xaa
1               5

<210> SEQ ID NO 27
<211> LENGTH: 7
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-S
<220> FEATURE:
<221> NAME/KEY: MISC_FEATURE
<222> LOCATION: (7)..(7)
<223> OTHER INFORMATION: Xaa is A-NH2

<400> SEQUENCE: 27

Xaa Arg Arg Gly Glu Leu Xaa
1               5

<210> SEQ ID NO 28
<211> LENGTH: 7
<212> TYPE: PRT
<213> ORGANISM: artificial
<220> FEATURE:
<223> OTHER INFORMATION: synthetic peptide

<400> SEQUENCE: 28

Ala Ser Arg Arg Gly Glu Leu
1               5

<210> SEQ ID NO 29
<211> LENGTH: 7
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (7)..(7)
<223> OTHER INFORMATION: Xaa is C-NH2

```
<400> SEQUENCE: 29

Xaa Ser Ser Arg Gly Glu Xaa
1               5

<210> SEQ ID NO 30
<211> LENGTH: 16
<212> TYPE: PRT
<213> ORGANISM: artificial
<220> FEATURE:
<223> OTHER INFORMATION: synthetic peptide

<400> SEQUENCE: 30

Cys Phe His Arg Gly Glu Phe Ser Ile Phe His Arg Gly Glu Phe Cys
1               5                   10                  15

<210> SEQ ID NO 31
<211> LENGTH: 15
<212> TYPE: PRT
<213> ORGANISM: artificial
<220> FEATURE:
<223> OTHER INFORMATION: synthetic peptide

<400> SEQUENCE: 31

Cys Ala Arg Arg Gly Glu Leu Ser Ala Arg Arg Gly Glu Leu Cys
1               5                   10                  15

<210> SEQ ID NO 32
<211> LENGTH: 16
<212> TYPE: PRT
<213> ORGANISM: artificial
<220> FEATURE:
<223> OTHER INFORMATION: synthetic peptide

<400> SEQUENCE: 32

Cys Ser His Arg Gly Glu Tyr Ser Lys Ser His Arg Gly Glu Tyr Cys
1               5                   10                  15

<210> SEQ ID NO 33
<211> LENGTH: 5
<212> TYPE: PRT
<213> ORGANISM: artificial
<220> FEATURE:
<223> OTHER INFORMATION: synthetic peptide

<400> SEQUENCE: 33

Ser Arg Arg Gly Glu
1               5

<210> SEQ ID NO 34
<211> LENGTH: 5
<212> TYPE: PRT
<213> ORGANISM: artificial
<220> FEATURE:
<223> OTHER INFORMATION: synthetic peptide

<400> SEQUENCE: 34

Ala Arg Arg Gly Glu
1               5

<210> SEQ ID NO 35
<211> LENGTH: 5
<212> TYPE: PRT
<213> ORGANISM: artificial
<220> FEATURE:
<223> OTHER INFORMATION: synthetic peptide
```

```
<400> SEQUENCE: 35

Phe His Arg Gly Glu
1               5

<210> SEQ ID NO 36
<211> LENGTH: 5
<212> TYPE: PRT
<213> ORGANISM: artificial
<220> FEATURE:
<223> OTHER INFORMATION: synthetic peptide

<400> SEQUENCE: 36

Ser His Arg Gly Glu
1               5

<210> SEQ ID NO 37
<211> LENGTH: 5
<212> TYPE: PRT
<213> ORGANISM: artificial
<220> FEATURE:
<223> OTHER INFORMATION: synthetic peptide

<400> SEQUENCE: 37

Lys Arg Gly Glu Asp
1               5

<210> SEQ ID NO 38
<211> LENGTH: 7
<212> TYPE: PRT
<213> ORGANISM: artificial
<220> FEATURE:
<223> OTHER INFORMATION: synthetic peptide

<400> SEQUENCE: 38

Lys Ser Arg Arg Gly Glu Asp
1               5

<210> SEQ ID NO 39
<211> LENGTH: 12
<212> TYPE: PRT
<213> ORGANISM: artificial
<220> FEATURE:
<223> OTHER INFORMATION: synthetic

<400> SEQUENCE: 39

Ser Arg Arg Gly Glu Leu Ser Arg Arg Gly Glu Leu
1               5                   10

<210> SEQ ID NO 40
<211> LENGTH: 12
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is dL
<220> FEATURE:
<221> NAME/KEY: MISC_FEATURE
<222> LOCATION: (2)..(2)
<223> OTHER INFORMATION: Xaa is dE
<220> FEATURE:
<221> NAME/KEY: MISC_FEATURE
<222> LOCATION: (4)..(4)
<223> OTHER INFORMATION: Xaa is dR
```

-continued

```
<220> FEATURE:
<221> NAME/KEY: MISC_FEATURE
<222> LOCATION: (5)..(5)
<223> OTHER INFORMATION: Xaa is dR
<220> FEATURE:
<221> NAME/KEY: MISC_FEATURE
<222> LOCATION: (6)..(6)
<223> OTHER INFORMATION: Xaa is dS
<220> FEATURE:
<221> NAME/KEY: MISC_FEATURE
<222> LOCATION: (7)..(7)
<223> OTHER INFORMATION: Xaa is dL
<220> FEATURE:
<221> NAME/KEY: MISC_FEATURE
<222> LOCATION: (8)..(8)
<223> OTHER INFORMATION: Xaa is dE
<220> FEATURE:
<221> NAME/KEY: MISC_FEATURE
<222> LOCATION: (10)..(10)
<223> OTHER INFORMATION: Xaa is dR
<220> FEATURE:
<221> NAME/KEY: MISC_FEATURE
<222> LOCATION: (11)..(11)
<223> OTHER INFORMATION: Xaa is dR
<220> FEATURE:
<221> NAME/KEY: MISC_FEATURE
<222> LOCATION: (12)..(12)
<223> OTHER INFORMATION: Xaa is dS

<400> SEQUENCE: 40

Xaa Xaa Gly Xaa Xaa Xaa Xaa Xaa Gly Xaa Xaa Xaa
1               5                   10

<210> SEQ ID NO 41
<211> LENGTH: 16
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is Ac-dC
<220> FEATURE:
<221> NAME/KEY: MISC_FEATURE
<222> LOCATION: (2)..(2)
<223> OTHER INFORMATION: Xaa is dL
<220> FEATURE:
<221> NAME/KEY: MISC_FEATURE
<222> LOCATION: (3)..(3)
<223> OTHER INFORMATION: Xaa is dE
<220> FEATURE:
<221> NAME/KEY: MISC_FEATURE
<222> LOCATION: (5)..(5)
<223> OTHER INFORMATION: Xaa is dR
<220> FEATURE:
<221> NAME/KEY: MISC_FEATURE
<222> LOCATION: (6)..(6)
<223> OTHER INFORMATION: Xaa is dR
<220> FEATURE:
<221> NAME/KEY: MISC_FEATURE
<222> LOCATION: (7)..(7)
<223> OTHER INFORMATION: Xaa is dS
<220> FEATURE:
<221> NAME/KEY: MISC_FEATURE
<222> LOCATION: (8)..(8)
<223> OTHER INFORMATION: Xaa is dA
<220> FEATURE:
<221> NAME/KEY: MISC_FEATURE
<222> LOCATION: (9)..(9)
<223> OTHER INFORMATION: Xaa is dA
<220> FEATURE:
<221> NAME/KEY: MISC_FEATURE
<222> LOCATION: (10)..(10)
<223> OTHER INFORMATION: Xaa is dE
```

```
-continued

<220> FEATURE:
<221> NAME/KEY: MISC_FEATURE
<222> LOCATION: (11)..(11)
<223> OTHER INFORMATION: Xaa is dE
<220> FEATURE:
<221> NAME/KEY: MISC_FEATURE
<222> LOCATION: (13)..(13)
<223> OTHER INFORMATION: Xaa is dR
<220> FEATURE:
<221> NAME/KEY: MISC_FEATURE
<222> LOCATION: (14)..(14)
<223> OTHER INFORMATION: Xaa is dR
<220> FEATURE:
<221> NAME/KEY: MISC_FEATURE
<222> LOCATION: (15)..(15)
<223> OTHER INFORMATION: Xaa is dS
<220> FEATURE:
<221> NAME/KEY: MISC_FEATURE
<222> LOCATION: (16)..(16)
<223> OTHER INFORMATION: Xaa is C-NH2

<400> SEQUENCE: 41

Xaa Xaa Xaa Gly Xaa Xaa Xaa Xaa Xaa Xaa Xaa Gly Xaa Xaa Xaa Xaa
1               5                   10                  15

<210> SEQ ID NO 42
<211> LENGTH: 7
<212> TYPE: PRT
<213> ORGANISM: artificial
<220> FEATURE:
<223> OTHER INFORMATION: synthetic peptide

<400> SEQUENCE: 42

Thr Asp Ile Lys Gly Lys Glu
1               5

<210> SEQ ID NO 43
<211> LENGTH: 9
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-Ac-C
<220> FEATURE:
<221> NAME/KEY: MISC_FEATURE
<222> LOCATION: (9)..(9)
<223> OTHER INFORMATION: Xaa is C-NH2

<400> SEQUENCE: 43

Xaa Thr Asp Ile Lys Gly Lys Glu Xaa
1               5
```